United States Patent
Nazarenko et al.

(10) Patent No.: US 8,901,287 B2
(45) Date of Patent: *Dec. 2, 2014

(54) DETECTION OF NUCLEIC ACIDS BY TARGET-SPECIFIC HYBRID CAPTURE METHOD

(75) Inventors: Irina Nazarenko, Gaithersburg, MD (US); Attila Lorincz, North Potomac, MD (US); Paul Eder, Bethesda, MD (US); Brian Lowe, Olney, MD (US); Richard Mallonee, Baltimore, MD (US); Ha Thai, Chevy Chase, MD (US)

(73) Assignee: Qiagen Gaithersburg, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/576,425

(22) Filed: Oct. 9, 2009

(65) Prior Publication Data

US 2010/0036104 A1 Feb. 11, 2010

Related U.S. Application Data

(60) Division of application No. 11/269,003, filed on Nov. 7, 2005, now Pat. No. 7,601,497, which is a continuation-in-part of application No. 11/005,617, filed on Dec. 6, 2004, now abandoned, which is a continuation-in-part of application No. 10/971,251, filed on Oct. 20, 2004, now abandoned.

(51) Int. Cl.
*C12Q 1/70* (2006.01)
*C12Q 1/68* (2006.01)

(52) U.S. Cl.
CPC .............. *C12Q 1/708* (2013.01); *C12Q 1/6834* (2013.01); *C12Q 1/6804* (2013.01)
USPC ...................... 536/24.32; 435/6.12; 536/24.33

(58) Field of Classification Search
USPC .................................. 536/24.31, 24.32; 435/6
See application file for complete search history.

(56) References Cited

U.S. PATENT DOCUMENTS

| | | |
|---|---|---|
| 4,486,536 A | 12/1984 | Baker et al. |
| 4,486,539 A | 12/1984 | Ranki et al. |
| 4,563,417 A | 1/1986 | Alabrella et al. |
| 4,563,419 A | 1/1986 | Ranki et al. |
| 4,731,325 A | 3/1988 | Palva et al. |
| 4,732,847 A | 3/1988 | Stuart et al. |
| 4,743,535 A | 5/1988 | Carrico |
| 4,751,177 A | 6/1988 | Stabinsky |
| 4,775,619 A | 10/1988 | Urdea |
| 4,833,084 A | 5/1989 | Carrico |
| 4,851,330 A | 7/1989 | Kohne |
| 4,865,980 A | 9/1989 | Stuart et al. |
| 4,868,105 A | 9/1989 | Urdea et al. |
| 4,889,798 A | 12/1989 | Rabbani |
| 4,894,325 A | 1/1990 | Englehardt et al. |
| 5,082,830 A | 1/1992 | Brakel et al. |
| 5,106,727 A | 4/1992 | Hartley et al. |
| 5,116,734 A | 5/1992 | Higgs et al. |
| 5,200,313 A | 4/1993 | Carrico |
| 5,288,611 A | 2/1994 | Kohne |
| 5,374,524 A | 12/1994 | Miller |
| 5,424,413 A | 6/1995 | Hogan et al. |
| 5,437,977 A | 8/1995 | Segev |
| 5,474,895 A | 12/1995 | Ishii et al. |
| 5,484,699 A | 1/1996 | Bouma et al. |
| 5,556,748 A | 9/1996 | Douglas |
| 5,614,362 A | 3/1997 | Urdea et al. |
| 5,623,049 A | 4/1997 | Lobberding et al. |
| 5,627,030 A | 5/1997 | Pandian et al. |
| 5,629,153 A | 5/1997 | Urdea |
| 5,629,156 A | 5/1997 | Shah et al. |
| 5,641,630 A | 6/1997 | Snitman |
| 5,656,731 A | 8/1997 | Urdea |
| 5,681,697 A | 10/1997 | Urdea et al. |
| 5,681,897 A | 10/1997 | Silvis et al. |
| 5,695,926 A | 12/1997 | Cros et al. |
| 5,702,893 A | 12/1997 | Urdea et al. |
| 5,728,531 A | 3/1998 | Yamada et al. |
| 5,731,153 A | 3/1998 | Lucas et al. |
| 5,736,316 A | 4/1998 | Irvine et al. |
| 5,747,244 A | 5/1998 | Sheridan et al. |
| 5,747,248 A | 5/1998 | Collins |
| 5,750,338 A | 5/1998 | Collins et al. |
| 5,759,773 A | 6/1998 | Tyagi et al. |
| 5,786,183 A | 7/1998 | Ryder et al. |

(Continued)

FOREIGN PATENT DOCUMENTS

| | | |
|---|---|---|
| EP | 0163220 | 12/1985 |
| EP | 0167366 | 1/1986 |

(Continued)

OTHER PUBLICATIONS

Cole, S.T. et al. Human papillomavirus type 18 E6, E7, E1, E2, E4, E5, L1 and L2 genes. J. Mol. Biol., vol. 193 (4), pp. 599-608, 1987.*

Wicks et al., "A Sandwich Hybridization Assay Employing Enzyme Amplification for Determination of Sepcific Ribosomal RNA from Unpurified Cell Lysates", Analytical Biochemistry 259, pp. 258-264, 1998.

Mazzulli et al., "Multicenter Comparison of the Digene Hybride Capture CMV DNA Assay (version 2.0) the pp65 Antignenemia Assay, and Cell Culture for Detection of Cytomegalovirus Viremia", J. Clin. Microbiol., vol. 37, No. 4, pp. 958-963, 1999.

Murakami et al., "Fluorescent-Labeled Oligonucleotide Probes: Detection of Hybride Formation in Solution by Fluorscence Polarization Spectroscopy", Nucleic Acids Res., vol. 19(15), pp. 4097-4102, 1991.

Broker et al., "A Molecular Portrait of Human Papillomavirus Carcinogenesis", Cancer Cells, vol. 7, pp. 197-208, 1989 (Roche EU Opposition).

(Continued)

*Primary Examiner* — Prabha Chunduru

(74) *Attorney, Agent, or Firm* — Miles & Stockbridge, PC

(57) ABSTRACT

Target-specific hybrid capture (TSHC) provides a nucleic acid detection method that is not only rapid and sensitive, but is also highly specific and capable of discriminating highly homologous nucleic acid target sequences. The method produces DNA:RNA hybrids which can be detected by a variety of methods.

11 Claims, No Drawings

(56) References Cited

U.S. PATENT DOCUMENTS

| | | | |
|---|---|---|---|
| 5,792,606 A | 8/1998 | Deger et al. | |
| 5,800,994 A | 9/1998 | Martinelli et al. | |
| 5,821,339 A | 10/1998 | Schaffer et al. | |
| 5,827,661 A | 10/1998 | Blais | |
| 5,853,993 A | 12/1998 | Dellinger et al. | |
| 5,888,724 A | 3/1999 | Silverstein et al. | |
| 5,981,179 A | 11/1999 | Lorincz et al. | |
| 5,994,079 A | 11/1999 | De La Rosa et al. | |
| 6,010,895 A | 1/2000 | Deacon et al. | |
| 6,043,038 A | 3/2000 | Sivaraja et al. | |
| 6,057,099 A | 5/2000 | Nathan et al. | |
| 6,083,925 A | 7/2000 | Li et al. | |
| 6,110,676 A | 8/2000 | Coull et al. | |
| 6,110,682 A | 8/2000 | Dellinger et al. | |
| 6,221,581 B1 | 4/2001 | Engelhardt et al. | |
| 6,228,578 B1 | 5/2001 | Impraim et al. | |
| 6,232,462 B1 | 5/2001 | Collins et al. | |
| 6,268,128 B1 | 7/2001 | Collins et al. | |
| 6,277,579 B1 | 8/2001 | Lazar et al. | |
| 6,326,136 B1 | 12/2001 | Lazar et al. | |
| 6,355,424 B1 | 3/2002 | Lorincz et al. | |
| 6,436,662 B1 | 8/2002 | Mielzynska et al. | |
| 6,521,190 B1 | 2/2003 | Edens et al. | |
| 6,544,732 B1 | 4/2003 | Chee et al. | |
| 6,583,278 B1 | 6/2003 | Carter | |
| 6,686,151 B1 * | 2/2004 | Lazar et al. | 435/6.11 |
| 6,828,098 B2 | 12/2004 | Langmore et al. | |
| 6,890,729 B2 | 5/2005 | Mietzynska et al. | |
| 6,969,585 B2 | 11/2005 | Lorincz et al. | |
| 6,977,148 B2 | 12/2005 | Dean et al. | |
| 7,001,776 B2 | 2/2006 | Botacini das Dores et al. | |
| 7,371,518 B2 | 5/2008 | Lorincz et al. | |
| 7,812,144 B2 | 10/2010 | Karlsen | |
| 7,829,691 B2 * | 11/2010 | Anthony et al. | 536/24.32 |
| 8,012,944 B2 | 9/2011 | Lacasse et al. | |
| 2001/0055766 A1 | 12/2001 | Aristarkhov et al. | |
| 2002/0012936 A1 | 1/2002 | Lorincz et al. | |
| 2003/0096232 A1 | 5/2003 | Kris et al. | |
| 2003/0108897 A1 | 6/2003 | Drmanac | |
| 2003/0113781 A1 * | 6/2003 | Bortolin et al. | 435/6 |
| 2003/0175765 A1 | 9/2003 | Kessler et al. | |
| 2003/0175789 A1 | 9/2003 | Weininger et al. | |
| 2004/0180362 A1 | 9/2004 | Lazar et al. | |
| 2004/0214302 A1 | 10/2004 | Anthony et al. | |
| 2005/0026976 A1 | 2/2005 | Curtin et al. | |
| 2005/0032038 A1 | 2/2005 | Fisher et al. | |
| 2005/0032105 A1 | 2/2005 | Bair et al. | |
| 2005/0119217 A1 | 6/2005 | Lacasse et al. | |
| 2005/0147996 A1 | 7/2005 | Sorge | |
| 2006/0051809 A1 | 3/2006 | Nazarenko et al. | |
| 2006/0160188 A1 | 7/2006 | Kurnit et al. | |
| 2006/0240449 A1 | 10/2006 | McGlennen et al. | |
| 2007/0109898 A1 | 5/2007 | Kasai | |
| 2007/0154884 A1 | 7/2007 | Lorincz | |
| 2007/0292899 A1 | 12/2007 | Lovell et al. | |
| 2008/0200344 A1 | 8/2008 | Cheng | |
| 2008/0247914 A1 | 10/2008 | Edens et al. | |
| 2009/0032445 A1 | 2/2009 | Doak et al. | |
| 2009/0263819 A1 | 10/2009 | Muraca | |
| 2009/0286687 A1 | 11/2009 | Dressman et al. | |
| 2009/0298187 A1 | 12/2009 | Nazarenko et al. | |
| 2010/0081124 A1 | 4/2010 | Abravaya et al. | |
| 2010/0311039 A1 | 12/2010 | Lowe et al. | |
| 2011/0009277 A1 | 1/2011 | Devos et al. | |
| 2014/0087449 A1 | 3/2014 | Ballhause et al. | |

FOREIGN PATENT DOCUMENTS

| | | |
|---|---|---|
| EP | 0184017 | 6/1986 |
| EP | 0079139 | 1/1988 |
| EP | 0281927 | 9/1988 |
| EP | 0288737 | 11/1988 |
| EP | 0333465 | 9/1989 |
| EP | 0336454 | 11/1992 |
| EP | 0144914 | 6/1995 |
| EP | 0415978 | 3/1996 |
| EP | 0703296 | 3/1996 |
| EP | 1 806 410 A2 | 7/2007 |
| EP | 2 184 368 A1 | 5/2010 |
| JP | T H-07-505759 A | 6/1995 |
| JP | 200400508019 A | 3/2004 |
| JP | T-2007-509861 A | 4/2007 |
| JP | 2009 106220 | 5/2009 |
| WO | 8607387 | 12/1986 |
| WO | 8839957 | 6/1988 |
| WO | 91/08312 A1 | 6/1991 |
| WO | 9310263 | 5/1993 |
| WO | 8402721 | 7/1994 |
| WO | 9416108 | 7/1994 |
| WO | 9516055 | 6/1995 |
| WO | 9517430 | 6/1995 |
| WO | 9640992 | 5/1996 |
| WO | 9640992 | 12/1996 |
| WO | 9705277 | 2/1997 |
| WO | 9710364 | 3/1997 |
| WO | 9731256 | 8/1997 |
| WO | 9818488 | 5/1998 |
| WO | 9822620 | 5/1998 |
| WO | 9859044 | 12/1998 |
| WO | 99/02488 | 1/1999 |
| WO | 9929909 | 6/1999 |
| WO | 9932654 | 7/1999 |
| WO | 9936571 | 7/1999 |
| WO | 9939001 | 8/1999 |
| WO | 9940224 | 8/1999 |
| WO | 9949224 | 9/1999 |
| WO | 9950459 | 10/1999 |
| WO | 0060116 | 10/2000 |
| WO | 0136681 | 5/2001 |
| WO | 0196608 | 12/2001 |
| WO | WO 0196608 A1 * | 12/2001 |
| WO | 02066993 A1 | 8/2002 |
| WO | 2004/087950 | 10/2004 |
| WO | 2005042030 A1 | 5/2005 |
| WO | 2005/088311 A1 | 9/2005 |
| WO | 2005080602 | 9/2005 |
| WO | 2006039563 A2 | 4/2006 |
| WO | 2006/124771 A2 | 11/2006 |
| WO | 2007/056723 | 5/2007 |
| WO | 2007/130519 A2 | 11/2007 |
| WO | 2007134252 A1 | 11/2007 |
| WO | 2008/036061 | 3/2008 |
| WO | 2008/139938 A1 | 11/2008 |
| WO | 2008149237 A2 | 12/2008 |
| WO | 2009/057993 A1 | 5/2009 |
| WO | 2009/123996 | 10/2009 |
| WO | 2010/004251 A1 | 1/2010 |
| WO | 2010/028382 | 3/2010 |
| WO | 2010/127228 A1 | 11/2010 |

OTHER PUBLICATIONS

Higgins et al., "Transcription Patterns of Human Papillomavirus Type 16 in Genital Intraepithelial Neoplasia: Evidence for Promoter Usage with the E7 Open Reading Frame during Epithelial Differentiation", Journal of General Virology, vol. 73, pp. 2047-2057, 1992 (Roche EU Opposition).

Karlsen et al., "Use of Multiple PCR Primer Sets for Optimal Detection of Human Papillomavirus", Journal of Clinical Microbiology, pp. 2095-2100, Sep. 1996 (Roche EU Opposition).

Park et al., "Physical Status and Expression of HPV Genes in Cervical Cancers", Gynecologic Oncology, vol. 65, pp. 121-129, 1997 (Roche EU Opposition).

Stoler et al., "Human Papillomavirus Type 16 and 18 Gene Expression in Cervical Neoplasias", Human Pathology, vol. 23, No. 2, pp. 117-128, Feb. 1992 (Roche EU Opposition).

Devilliers et al., "Classification of Papillomaviruses", Virology, vol. 324, pp. 17-27, 2004.

Howley et al., "A Rapid Method for Detecting and Mapping Homology between Heterologous DNAs", Journal of Bilogical Chemistry, vol. 254, No. 11, pp. 4879-4883.

Law et al., "Conserved Polynucleotide Sequences Among the Genomics of Paillomaviruses", Journal of Virology, vol. 32, No. 1, pp. 199-207, Oct. 1979.

(56) References Cited

OTHER PUBLICATIONS

Heilman et al., "Cloning of Human Papilloma Virus Genomic DNAs and Analysis of Homologous Polynucleotide Sequences", Journal of Virology, vol. 36, No. 2, pp. 395-407, Nov. 1980.
Howard et al., "Optimizing the Hybrid Capture II Human Papillomavirus Test to Detect Cervical Intraepithelial Neoplasia", Obstetrics and Gynecology, vol. 100, No. 5, Part 1, pp. 972-980, Nov. 2002.
Lorincz, A.T., "Molecular Methods for the Detection of Human Papillomavirus Infection", Obstetrics and Gynecology Clinics of North America, vol. 23, No. 3, pp. 707-730, Sep. 1996.
Hames et al., "Nucleic Acid Hybridization. A practical Approach", 1985.
Hermanson, et al., "Immobilized Affinity Ligand Techniques", 1992.
Taylor, "Protein Immobilization. Fundamentals and Applications", 1991.
Partial International Search Report for PCT/US2009/062061, mail date Jan. 5, 2010.
Partial International Search Report for PCT/US2009/062041, mail date Jan. 5, 2010.
Bhan P, et al., "2', 5'-linked oligo-3'-deoxyribonucleoside phosphorothioate chimeras: thermal stability and antisense inhibition of gene expression," Nucleic Acids Research Aug. 15, 1997, vol. 25, No. 16, pp. 3310-3317, XP002560367, ISSN: 0305-1048, p. 3313.
Genetech Diagnostics Pvt. Ltd., "Digene HBV Test Hybrid Capture II," Jun. 6, 2008, XP-00256068, retrieved from internet: URL:http://www.gentechin.com/hbvdnatestkit.htm>, the whole document.
Hantz S, et al., "[Evalutation of accuracy of three assays for human papillomavirus detection and typing: Hybrid Capture 2, HPV Consensus kit and Amplicor HPB.]," Pathologie-Biologie, Feb. 2008, vol. 56, No. 1, Feb. 2008, pp. 29-35, XP 002560369, ISSN: 0369-8114, the whole document.
Sandri et al., "Comparison of the Digene HC2 Assay and the Roche AMPLICOR Human Papillomavirus (HPV) Test for Detection of High-Risk HPV Genotypes in Cervical Samples," Journal of Clinical Microbiology, Jun. 2006, vol. 44, No. 6, pp. 2141-2146, XP002560370, ISSN: 0095-1137, the whole document.
Boston Bioproducts Inc., "Protein Extraction buffers," Sep. 2, 2007, XP002560371, Retrieved from the Internet: URL: http://www.bostonbioproducts.com/product_disply1.php?page=20&limit=10&id=4>, the whole document.
Bart "General Principles of Immunoprecipitation," Jul. 31, 2008, XP002560372, URL:http://pingu.salk.edu/{sefton/Hyper_protocols/immunoprecip.html>, the whole document.
Thai et al., "An HPV 16, 18, and 45 genotyping test based on Hybrid Capture technology," Journal of Clinical Virology 45, S1 (2009) pp. 593-597.
Kitagawa et al., "Comparison of Poly(A) Poly(dT) and Poly(I) Poly(dC) As Immunogens for the Induction of Antibodies to RNA-DNA Hybrids," Molecular Immunology, vol. 19, No. 3, pp. 413-420, 1982.
Ishikawa et al., "Enzyme-Labeling of Antiboldies and Their Fragments for Enzyme Immunoassay and Immunohistochemical Staining," Journal of Immunoassay and Immunochemistry, 4: 3, 209-327.
Means et al., "Chemical Modifications of Proteins: History and Applications," Bioconjugate Chem. 1990, 1, 2-12.
Jakobovits et al., "Analysis of homozygous mutant chimeric mice: Deletion of the immunoglobulin heavy-chain joining region blocks B-cell development and antibody production," Proc. Natl. Acad. Sci. USA, vol. 90, pp. 2551-2555, Mar. 1993 Genetics.
Jakobovits et al., "Germ-line transmission and expression of a human-derived yeast artificial chromosome," pp. 255-258, Nature, vol. 362, Mar. 18, 1993.
U.S. Appl. No. 12/588,304, titled "Automated Assay and System," filed Oct. 9, 2009 (not yet published).
U.S. Appl. No. 12/588,306, titled "Open Platform Automated Sample Processing System," filed Oct. 9, 2009 (not yet published).
U.S. Appl. No. 12/622,131, titled "Multiple-Input Analytical System," filed Nov. 19, 2009 (not yet published).
U.S. Appl. No. 12/605,540, titled "Fast Results Hybrid Capture Assay and System," filed Oct. 26, 2009 (not yet published).
U.S. Appl. No. 12/605,605, titled "Fast Results Hybrid Capture Assay on an Automated Platform," filed Oct. 26, 2009 (not yet published).
International Search Report for PCT/US2009/041033, dated Dec. 22, 2009.
Sigurdsson et al., "Human papillomavirus (HPV) in an icelandic population: the role of HPV DNA testing based on hybrid capture and PCR assays among women with screen-dtected abnormal PAP smears," In: International Journal of Cancer, Jul. 1997, vol. 72(3), pp. 446-452.
Michele De Villiers et al., "Classification of papillomarviruses," In: Virology, Jun. 2004, vol. 324(1), pp. 17-27—see table 3.
GenBank Accession No. K02718, "Human papillomavirus type 16 (HPV16), complete genome.", Mar. 18, 1994. See http://www.ncbi.nlm.nihgov/nuccore/333031.
GenBank Accession No. X74479, "human papillomavirus type 45 genomic DNA.", Apr. 18, 2005. See http://www.ncbi.nlm.nih.gov/nuccore/397022.
GenBank Accession No. X05015, "Human papillomavirus type 18 E6, E7, E1, E2, E4, E5, L1 & L2 genes.", Apr. 18, 2005. See http://www.ncbi.nlm.nih.gov/nuccore 60975.
GenBank Accession No. J04353, "Human papillomavirus type 31 (HPV-31), complete genome.", Mar. 18, 1994. See http://www.ncbi.nlm.nih.gov/nuccore/333048.
GenBank Accession No. M12732, "Human papillomavirus type 33, complete genome.", Mar. 21, 1994. See http://www.ncbi.nlm.nih.gov/nuccore/333049.
GenBank Accession No. M74117, "Human papillomavirus type 35, complete genome.", May 10, 2002. See http://www.ncbi.nlm.nih.gov/nuccore/333050.
GenBank Accession No. M62849, "Human papillomavirus ORFs.", Jan. 26, 2001. See http://www.ncbi.nlm.nih.gov/nuccore/333245.
GenBank Accession No. M62877, "Human papillomavirus type 51 genomic DNA, partial sequence.", Oct. 29, 1999. See http://www.ncbi.nlm.nih.gov/nuccore/333087.
GenBank Accession No. X74481, "Human papillomavirus type 52 genomic DNA.", Apr. 18, 2005. See http://www.ncbi.nlm.nih.gov/nuccore/397038.
GenBank Accession No. X74483, "Human papillomavirus type 56 genomic DNA.", Apr. 18, 2005. See http://www.ncbi.nlm.nih.gov/nuccore/397053.
GenBank Accession No. D90400, "Human papillomavirus type 58, complete genome.", Dec. 7, 2007. See http://www.ncbi.nlm.nih.gov/nuccore/222386.
GenBank Accession No. X77858, "Human papillomavirus type 59, complete viral genome.", Apr. 18, 2005. See http://www.ncbi.nlm.nih.gov/nuccore/557236.
GenBank Accession No. U31794, "Human papillomavirus type 66, complete genome.", Oct. 18, 1995. See http://www.ncbi.nlm.nih.gov/nuccore/1020290.
GenBank Accession No. X67161, "Human papillomavirus type L1 gene for major capsid protein.", Apr. 18, 2005. See http://www.ncbi.nlm.nih.gov/nuccore/1197494.
GenBank Accession No. AB027021, "Human papillomavirus type 82 DNA, complete genome.", Jun. 22, 2000. See http://www.ncbi.nlm.nih.gov/nuccore/6970427.
Kleter et al., "Development and clinical evaluation of a highly sensitive PCT-reverse hybridization line probe assay for detection and identification of anogenital human papillomafirus," In: Journal of clinical Micorbiology, Aug. 1999, vol. 37(8), pp. 2508-2517, see the whole document.
Lowe, et al., "A computer program for selection of oligonucleotide primers for polymerase chain reactions", Nucleic Acid Res., vol. 18, No. 7, pp. 1757-1761 (1990).
Mittendorf T, et al., "HPV-DNA-Diagnostik zur Zervixkarzinomfrüherkennung; Deutsche Agentur für HTA des Deutschen Instituts für Medizinische Dokumentation und Information," 1. Auflage 2007.

(56) References Cited

OTHER PUBLICATIONS

Nanda K, et al., "Accuracy of the Papanicolaou Test in Screening for and Follow-up of Cervical Cytologic Abnormalities: A Systematic Review, Annals of Internal Medicine," 132(10):810-819, May 16, 2000.

Davey DD, et al., "Introduction and Commentary, Strategic Science Symposium, Human Papillomavirus Testing—Are you ready for a new era in cervical cancer screening?," Arch Pathol Lab Med, 127: 927-929, Aug. 2003.

Malloy C, et al., "HPV DNA Testing: Technical and Programmatic Issues for Cervical Cancer Prevention in Low-Resource Settings," Path, Dec. 2000.

Stacey SN, et al., "Translation of the Human Papillomavirus Type 16 E7 Oncoprotein from Bicistronic mRNA is independent of Splicing Events within the E6 Open Reading Frame," Journal of Virology, 69(11):7023-7031. Nov. 1995.

Hsu E, et al., Quantification of HPV-16 E6-E7 Transcription in Cervical Intraepithelial Neoplasia by Reverse Transcriptase Polymerase Chain Reaction, Int. J. Cancer: 55, 397-401 (1993).

Bohm S, et al., "The Predominant mRNA Class in HPV16-Infected Genital Neoplasias does not Encode the E6 or the E7 Protein," Int. J. Cancer: 55, 791-798 (1993).

Middleton, K, et al. "Organization of Human Papillomavirus Productive Cycle during Neoplastic Progression Provides a Basis for Selection of Diagnostic markes," Journal of Virology, Oct. 2003, pp. 10186-10201.

Stoler, M, et al., "Human Papillomavirus Type 16 and 18 Gene Expression in Cervical Neoplasias," Human Pathol. 23 (1992), pp. 117-128.

Higgins, G, et al., "Transcription patterns of human papillomavirus type 16 in genital intraepithelial neoplasia: evidence for promoter usage within the E7 open reading frame during epithelial differentiation," J. Gen. Virol. 73(1992), pp. 2047-2057.

Karlsen, F, et al., "Use of Multiple PCR Primer Sets for Optimal Detection of Human Papillomavirus," J. Clin. Microbiol. 34 (1996), pp. 2095-2100.

Park, JS, et al., "Physical Status and Expression of HPV Genes in Cervical Cancers," Gynec. Oncol. 95 (1997), pp. 121-129.

Broker, TR, et al., "A Molecular Portrait of Human Papillomavirus Carcinogenesis," Cancer Cells 7 (1989), pp. 197-207.

Letter dated Jan. 6, 2010 to EPO re EP 1 038 022 (46 pages).
Letter to EPO dated Mar. 2, 2009 re EP 1 038 022 (15 pages).
Letter to EPO dated Oct. 6, 2008 re EP 1 038 022 (27 pages).
Letter to EPO dated Aug. 8, 2008 re EP 1 038 022 (11 pages).
EPO decision dated May 27, 2008 re Opposition of EP 1 038 022 (19 pages).
Letter to EPO dated Jan. 25, 2008 re EP 1 038 022 (10 pages).
Letter to EPO dated Jan. 23, 2008 re EP 1 038 022 (6 pages).
Communication from EPO dated May 14, 2007 re EP 1 038 022 (8 pages).
Letter to EPO dated Oct. 4, 2006 re EP 1 038 022 (11 pages).
Letter to EPO dated Apr. 18, 2006 re EP 1 038 022 (10 pages).

Dunn and Hassell; "A Novel Method to Map Transcripts: Evidence for Homology between an Adenovirus mRNA and Discrete Multiple Regions of the Viral Genome", Cell, 12, pp. 23-36, Sep. 1977.

Coutlee et al., Nonisotopic Detection of RNA in an Enzyme Immunoassay using a Monocloanal Antibody Against DNA-RNA Hybrids Analytical Biochemistry 181; pp. 13-162, 1989.

Chen et al., DNA Optical Sensor: A Rapid Method for the Detection of DNA Hybridization: Biosensors & Bioelectronics 13; pp. 451-458, 1998.

Chevrier et al., "Isolation of a Specific DNA fragment and Development of a PCR Based Method for the Detection of *Mycobacterium genavense*", FEMS Immunology and Medical Microbiology 23; pp. 243-452, 1999.

Hakala et al., "Simultaneous Detection of Several Oligonucleotides by time-Resolved Fluorometry: The Use of a Mixture of Categorized Microparticles in a Sandwich Type Mixed-Phase Hybridization Assay", Nucleic Acid Research, 26: pp. 5581-5588, 1998.

Gelmetti et al., "Detection of Rabbit Haemorrhagic Disease Virus )RHDV) by In Situ Hybridization With a Digoxigenin Labelled RNA Probe", Journal of Virological Methods 72: pp. 219-226, 1998.

Radtkey et al., "Rapid, High Fidelity Analysis of Simple Sequence Repeats on an Electronically Active DNA Microchip", Nucleic Acids Research 28: i-vi, 2000.

Namimatsu et al., "Detection of *Salmonella* by Using the Colorimetric DNA/rRNA Sandwich Hybridization in Microtiter Wells", J. Vet. Med. Sci. 62: pp. 615-619, 2000.

Lazar et al., "Hybrid Capture®: a Sensitive Signal Amplification-based Chemiluminescent Test for the Detection and Quantitation of Human viral and Bacterial pathogens", J. Clin. Ligand Assay 22: pp. 139-151, 1999.

Newman et al., "Solution Hybridization and Enzyme Immunoassay for Biotiylated DNA:RNA Hybrids to Detect Enteroviral RNA in Cell Culture", Mol. Cell Probes 3: pp. 375-382, 1989.

Lamoureux et al., "Detection of *Campylobacter jejuni* in Food and Poultry Viscera Using Immunomagnetic Separation and Microtitre Hybridization", J. Appl. Microbiol. 83: pp. 651-651, 1997.

Coutlee et al., "Quantitative Detection of Messenger RNA by Solution Hybridization and Enzyme Immunoassay", J. biol. chem. 265: pp. 11601-11604, 1990.

Stollar et al., "Immunochemical Approaches to Gene Probe Assays", Anal. Biochem. 161: pp. 387-394, 1987.

Blais, B. W., "Transcriptional Enhancement of the *Listeria monocytogenes* PCR and Simple Immunoenzymatic Assay of the Product Using Anti-RNA:DNA Antibodies", Appl. Enviorn. Microbiol. 60: pp. 348-352, 1994.

Coutlee et al., "Detection of Transcript of Human Papillomaviruses 16 and 18 in Cancer-derived Cell Lines and Cervical Biopsies by Enzyme Immunoassay for DNA-RNA Hybrids Following Solution Hybridization", J. Clin. Microbiol. 29: pp. 968-974, 1991.

Viscidi et al., "Monoclonal Antibody Solution Hybridization Assay for Detection of Human Immunodeficiency Virus Nucleic Acids", J. Clin. Microbiol. 27: pp. 120-125, 1989.

Boguslawski et al., "Characterization of Monoclonal Antibody to DNA:RNA and Its Application to Immunodetection of Hybrids", J. Immunol. Methods 89; pp. 123-130, 1986.

Coutlee et al., "Immunodetection of DNA with Biotinylated RNA Probes: A Study of Reactivity of a Monoclonal Antibody to DNA-RNA Hybrids", Anal. Biochem. 181: pp. 96-105, 1989.

Coutlee et al., "Immunodetection of DNA with Biotinylated RNA Probes: A Study of Reactivity of a Monoclonal Antibody to DNA-RNA Hybrids", Anal. Biochem. 198: pp. 217 (Published erratum) 1991.

Coutlee et al., "Comparison of Colorimetric Fluorescent, and Enzymatic Amplification Substrate Systems in an Enzyme Immunoassay for Detection of DNA-RNA Hybrids", J. Clin. Microbiol. 27: pp. 1002-1007, 1989.

Dalrymple et al., "DNA sequence of the herpes simplex virus type 1 gene whose product is responsible for transcriptional activiation of immediate early promoters", Nucleic Acids Research, vol. 13, No. 21, pp. 7865-7879, 1985.

McLauchlan et al., "DNA sequence homology between two co-linear loci on the HSV genome which have different transforming abilities", The EMBO Journal, vol. 2, No. 11, pp. 1953-1961, 1983.

Goldsborough et al., "Nucleotide Sequence of Human Papillomavirus Type 31: A Cervical Neoplasia—Associated Virus", Virology, vol. 171, pp. 306-311, 1989.

Duncan et al., "DNA Sequence and Genetic content of the Hindlll 1 Region in the Short Unique Component of the Herpes Simplex Virus Type 2 Genome; Identification of the Gene Encoding Glycoprotein G, and Evolutionary Comparisons", J. Gen. Virol., vol. 63, pp. 19-38, 1987.

McGeoch et al., "DNA Sequence and Genetic content of the Hindlll 1 Region in the Short Unique Component of the Herpes Simplex Virus Type 2 Genome; Identification of the Gene Encoding Glycoprotein G, and Evolutionary Comparisons", J. Gen. Virol., vol. 63, pp. 19-38, 1987.

Yamada et al., "Human Papillomavirus Type 16 Variant Lineages in United States Populations characterized by Nucleotide Sequence Analysis of the E6, L2, and L1 Coding Segments", J. Virol., vol. 69, No. 12, pp. 7743-7753, Dec. 1995.

(56) References Cited

OTHER PUBLICATIONS

McGeoch et al., "Structures of Herpes Simplex Virus Type 1 Genes Required for Replication of Virus DNA", J. Virol., vol. 62, No. 2, pp. 444-453.
Zientara et al., "Use of reverse transcriptase-polymerase chain reaction (RT-PCR) and dot-blot hybridization for the detection and identification of African horse sickness virus nucleic acids", Arch Virol 14; pp. 317-327, 1998.
Mansy et al., "A PCR Based DNA Hybridization Capture System for the Detection of Human Cytomegalovirus. A Comparative Study with Other Identification Methods", Journal of Virological Methods 80; pp. 113-122, 1999.
Poulsen et al., "Detection of clinical Vacomycin-Resistant *Enterococci* in Denmark by Multiplex PCR and Sandwich Hybridization", APMIS, 107; pp. 404-412, 1999.
Sjoeroos et al., "Time-Resolved Fluorometry Based Sandwich Hybridization Assay for HLA-DQA1 Typing", Disease Markers 14; pp. 9-19, 1998.
Swain et al., "Nucleotide Sequence of the Herpes Simplex Virus Type 2 Thymidine Kinase Gene", J. Virol., vol. 46, No. 3, pp. 1045-1050, Jun. 1983.
Delius et al., "Primer-Directed Sequencing of Human Papillomavirus Types", Current Topics in Microbiology and Immunology, vol. 185, pp. 13-31, 1994.
Blair et al., "Herpes Simplex Virus Viron Stimulatory Protein mRNA Leader Contains Sequence Elements Which Increase Both Virus-Induced Transcription and mRNA Stability", J. Virol., vol. 62, No. 2, pp. 444-453, Aug. 1987.
McGeoch et al., "The Complete DNA Sequence of the Long Unique Region in the Genome of Herpes Simplex Virus Type 1", J. Gen Virol., vol. 69, pp. 1531-1574, 1988.
Larder et al., "Related functional domains in virus DNA polymerases", The EMBO J., vol. 6, No. 1, pp. 169-175, 1987.
Edman et al., "Pathogen Analysis and Genetic Predisposition Testing Using Microelectronic Arrays and Isothermal Amplification", Journal of Investigative medicine, 48, pp. 93-101, 2000.
Monteiro et al., "Evaluation of Performances of Three DNA Enzyme Immunoassays for Detection of *Helicobacter pylori* PCR Products from Biopsy Specimens", Journal of Clinical Microbiology, 35 pp. 2931-2936, 1997.
Chiu et al., "Sandwich-type Deoxyribonucleic Acid Hybridization Assays Based on Enzymen Ampliefied Time-Reseolved Fluorometry", Analyst., 123, pp. 1315-1319, 1998.
White et al., "Signal Amplification System for DNA Hybridization Assays Based on in vitro Expression of a DNA Label Encoding Apoaequorin", Nucleic Acids Research 27, i-viii, 1999.
Hakala et al., "Detection of Oligonucleotide Hybridization on a Single Microparticle by Time-Resolved Fluorometry: Quantitation and Optimization of a Sandwich Type Assay", Bioconjugate Chem. 9, pp. 316-321, 1998.
Zammatteo et al., "Comparison between Microwell and Bead Supports for the Detection of Human Cytomegalovirus Amplicons by Sandwich Hybridization", Analytical Biochemistry 253, pp. 180-189, 1997.
Fisher et al., "A System for the Quantitation of DNA Using a Microtiter Plate-Based Hybridization and Enzyme Amplification Technology", Analytical Biochemistry 251, pp. 280-287, 1997.
Bruckener-Lea et al., "Rotating Rod Renewable Microcolumns for automated, Solid-Phase DNA Hybridizations Studies", Anal. Chem. 72, pp. 4135-4141, 2000.
Allen et al., "High Resolution Genetic Typing of the Class II HLA-DRB1 Locus Using Group-Specific Amplification and SSO-Hybridization in Microplates", Hereditas 129, pp. 161-167, 1998.
Chomvarin et al., "Development of EIA for Detection of *Chlamydia trachomatis* in Genital Specimens", The Southeast Asian Journal of Tropical Medicine and Public Health, 31, pp. 96-103, 2000.
Alexandre et al., "Quantitative Determination of CMV DNA Using a Combination of Competitive PCR Amplification and Sandwich Hybridization", BioTechniques, 25, pp. 676-683, 1998.

Casadémont et al., "Rapid Detection of *Campylobacter fetus* by Polymerase Chain Reaction Combined With Non-Radioactive hybridization Using an Oligonucleotide Covalently Bound to Microwells", Molecular and Cellular Probes 14, pp. 233-240, 2000.
Brendan et al., "Related Functional Domains in Virus DNA Polymerases", The EMBO Journal, vol. 6, No. 1, pp. 160-175, 1987.
Chandler et al., "Detection of Dengue-2 Viral RNA by Reversible Target Capture Hybridization", J. Clin. Microbiol., vol. 31 (10), pp. 2641-2647, 1993.
International Search Report in PCT/US06/60603 mail dated Sep. 11, 2007 (2 pages).
International Search Report and Written Opinion of PCT/US2010/048714, dated Dec. 10, 2010 (14 pages).
International Preliminary Report on Patentability and Written Opinion of PCT/US2009/041033, dated Oct. 19, 2010 (6 pages).
International Search Report and Written Opinion of PCT/US2010/047769, dated Nov. 9, 2010 (11 pages).
Pachowics, et al., "Sequence specific large volume sample prep solution utilizing Hybrid Capture technology," 41st Annual Oak Ridge Conference; Baltimore, MD; Apr. 16, 2009; retrieved from the Internet: http://www.aacc.org/events/meeting_proceeding/2009/Documents/OakRidge09AllPosters.pdf.
Keegan et al., "Comparison of HPV detection technologies: Hybrid capture 2, PreTect HPV-Proofer and analysis of HPV DNA viral load in HPV16, HPV18 and HPV33 E6/E7 mRNA positive specimens," Journal of Virological Methods, Jan. 1, 2009, pp. 61-66, vol. 155, No. 1, Elsevier BV, XP025799776.
Murphy et al., "Isolation of RNA from cell lines and cervical cytology specimens stored in BD SurePath (TM) preservative fluid and downstream detection of housekeeping gene and HPV E6 expression using real time RT-PCR," Journal of Virological Methods, Mar. 1, 2009, pp. 138-144, vol. 156, No. 1-2, Elsevier BV, XP025941323.
Powell et al., "Recovery of human papillomavirus nucleic acids from liquid-based cytology media," Journal of Virological Methods, Oct. 1, 2006, pp. 58-62, vol. 137, No. 1, Elsevier BV, XP005600251.
Nazarenko et al., "A novel method of HPV genotyping using Hybrid Capture sample preparation method combined with GP5+/6+ PCR and multiplex detection on Luminex XMAP," Journal of Virological Methods, Dec. 1, 2008, pp. 76-81, vol. 154, No. 1-2, Elsevier BV, XP025680302.
Taha et al., "Universal Collection Medium (UCM) is as suitable as the Standard Transport Medium (STM) for Hybrid Capture II 6(HC-2) assay," Journal of Virological Methods, May 1, 2006, pp. 32-35, vol. 36, No. 1, Elsevier BV, XP025178639.
Nindl et al., "Human Papillomavirus Distribution in Cervical Tissues of Different Morphology as Determined by Hybrid Capture Assay and PCR," International Journal of Gynecological Pathology, Jan. 1, 1997, pp. 197-204, vol. 16, No. 3, Lippincott-Raven Publishers, XP008011933.
Hernandez-Hernandez et al., "Association between high-risk human papillomavirus DNA load and precursor lesions of cervical cancer in Mexican women," Gynecologic Oncology, Aug. 2003, pp. 310-317, vol. 90, No. 2, Elsevier Science, XP002603500.
Tsai et al., "Association between Quantitative High-Risk Human Papillomavirus DNA Load and Cervical Intraepithelial Neoplasm Risk," Cancer Epidemiology, Biomarkers & Prevention: American Association for Cancer Research, Nov. 2005, pp. 2544-2549, vol. 14, No. 11 pt 1, XP002603501.
Moodley et al., "Human papillomavirus prevalence, viral load and pre-cancerous lesions of the cervix in women initiating highly active antiretroviral therapy in South Africa: a cross-sectional study," BMC Cancer, Aug. 7, 2009, pp. 1-8, vol. 9, No. 275, Biomed Central Ltd, XP002603502.
Ronco et al., "HPV triage for low grade (L-SIL) cytology is appropriate for women over 35 in mass cervical cancer screening using liquid based cytology," European Journal of Cancer, Feb. 1, 2007, pp. 476-480, vol. 43, No. 3, Pergamon Press, Oxford GB, XP005868775.
International Search Report for PCT/US2009/062041, Patent Cooperation Treaty, Mar. 31, 2010 (17 pages).
International Search Report and Written Opinion of PCT/US2010/022264 dated Jun. 7, 2010 (19 pages).
Cohenford et al., "C-195. Rapid Detection of *Chlamydia trachomatis* from Specimens Collected from the ThinPrep Pap Test using Molecu-

(56) References Cited

OTHER PUBLICATIONS lar Beacons and the Roche LightCycler," Abstracts of the General Meeting of the American Society for Microbiology, The Society, Washington, DC. (Jan. 1, 2001), p. 195, vol. 101, XP001098006.
Gentech Diagnostics: "*Chlamydia* DNA Test Kit," (Jun. 6, 2008), XP002578832, Retrieved from the Internet: URL: http://www.gentechin.com/chlamydiatestkit.htm.
Taha et al., "Universal Collection Medium (UCM) is as suitable as the Standard Transport Medium (STM) for Hybrid Capture II (HC-2) assay," Journal of Clinical Virology, (May 1, 2006), pp. 32-35, vol. 36, No. 1, XP005367693.
Darwin et al., "Comparison of Digene Hybrid Capture 2 and Conventional Culture for Detection of *Chlamydia trachomatis* and *Neisseria gonorrhoeae* in Cervical Specimens," Journal of Clinical Microbiology, (Feb. 2002), pp. 641-644, vol. 40, No. 2, XP002578833.
Nazarenko et al., "A novel method of HPV genotyping using Hybrid Capture sample preparation method combined with GP5+/6+ PCR and multiplex detection on Luminex XMAP," Journal of Clinical Virology, (Dec. 1, 2008), pp. 76-81, vol. 154, No. 1-2, XP025680302.
International Search Report and Written Opinion of PCT/US10/33145, dated Aug. 5, 2010 (9 pages).
A Lorincz, "Hybrid Capture," Clin. Chem., (Jun. 1998), pp. 1363, vol. 44, No. 6.
Vernick et al., "The HPV DNA virus hybrid capture assay: What is it—and where do we go from here?" MLO Med. Lab. Obs., (Mar. 2003), pp. 8-10, 13, vol. 35, No. 3.
Supplementary European Search Report of PCT/US2006/060603, dated Jul. 7, 2010 (8 pages).
International Search Report and Written Opinion of PCT/US2011/22887, dated Jun. 1, 2011.
International Preliminary Report on Patentability and Written Opinion of PCT/US2009/062061, dated May 12, 2011.
International Preliminary Report on Patentability and Written Opinion of PCT/US2009/062041, dated May 12, 2011.
GenBank Submission FJ429103. 2009 [Retrieved from the Internet May 20, 2011: <URL:http://www.ncbl.nlm.nih.gov/nuccore/FJ429103.1>]; in entirety.
Ryncarz et al., "Development of a High-Throughput Quantitative Assay for Detecting Herpes Simplex Virus DNA in Clinical Samples," Journal of Clinical Microbiology; Jun. 1999; pp. 1941-1947; vol. 37, No. 6; American Society for Microbiology.
Partial European Search Report of EP10185824; mailed Feb. 16, 2011 (8 pages).
Scott et al., "Detection of herpes simplex virus type 1 shedding in the oral cavity by polymerase chain reaction and enzyme-linked immunosorbent assay at the prodromal stage of recrudescent herpes labialis," Journal of Oral Pathology & Medicine; Aug. 1997; pp. 305-309; vol. 26; No. 7; XP009143938.
International Search Report Based on Application No. PCT/US2012/020684 Mailed Oct. 25, 2012.
Clad et al.; "Performance of the Aptima High-Risk Human Papillomavirus MRNA Assay in a Referral Population in Comparison With Hybrid Capture 2 and Cytology"; Journal of Clinical Microbiology; Mar. 2011; LNKD—PUBMED:21191046; vol. 49; No. 3; Dec. 29, 2010; pp. 1071-1076; Abstract.
Li et al; Detection of Human Papillomavirus Genotypes With Liquid Bead Microarray in Cervical Lesions of Northern Chinese Patients; Cancer Genetics and Cytogenetics, Elsevier Science Publishing, New York, NY, US; vol. 182; No. 1; Mar. 6, 2008; pp. 12-17; Abstract.
Gheit et al.; "Development of a Sensitive and Specific Assay Combining Multiplex PCR and DNA Microarray Primer Extension to Detect High-Risk Mucosal Human Papillomavirus Types"; Journal of Clinical Microbiology, American Society for Microbiology, Washington, DC, US ; vol. 44; No. 6; Jun. 1, 2006; pp. 2025-2031; Abstract.
Han et al.; "Simultaneous Amplification and Identification of 25 Human Papillomavirus Types With Templex Technology"; Journal of Clinical Mircobiology 20061 US LNKD—DOI:10.1128/JCM.-01762-06; vol. 44; No. 11; Nov. 2006; pp. 4157-4162; Abstract.
Database EMBL [Online]; Jul. 19, 2007; "Sequence 25 From Patent EP1806410"; XP002675256; Retrieved From EBI Accession No. EMBL:CS42417; Database Accession No. CS642417; The Whole Document.
Database EMBL [Online]; Dec. 14, 2010; "Sequence 26 From Patent US 7812144"; XP00267527; Retrieved From EBI Accession No. EMBL:GX640151; Database Accession No. GX640151; The Whole Document.
Database Geneseq [Online]; Jan. 22, 2009; "HPV-16 E7/E6 Gene Target Sequence, Bases 752-774", XP002675258, Retrieved From EBI Accession No. GSN:ATS82292; Database Accession No. ATS82292; The Whole Document.
Database Geneseq [Online]; Jan. 22, 2009; "HPV-16 E7/E6 Gene Target Sequence, Bases 698-720"; XP002675259 Retrieved From EBI Accession No. GSN:ATS82290; Database Accession No. ATS82290; The Whole Document.
Database Geneseq [Online]; Apr. 1, 2010; "HPV16 E7 Gene Forward RT-PCR Primer SEQ ID 49"; XP002675260; Retrieved From EBI Accession No. GSN:AXU96631; Database Accession No. AXU96631; The Whole Document.
Database Geneseq [Online]; Apr. 21, 2005; "E7 Coding Region (1-87) Amplifying Sense PCR Primer, SEQ ID No: 37"; XP002675261; Retrieved From EBI Accession No. GSN:ADX15568; Database Accession No. ADX15568; Sequence.
Lowe et al; "A Hybrid-Capture Assay to Detect HPV MRNA Ratios in Cervical Specimens"; Journal of Virological Methods; vol. 179; No. 1; Jan. 2012; pp. 142-147.
International Search Report Based on Application No. PCT/US2012/026380 Mailed Oct. 15, 2012.
Yevgeniy S Belousov et al.: "Single nucleotide polymorphism genotyping by two colour melting curve analysis using the MGB elicpse TM probe system in challenging sequence environment" Human Genomics, Henry Stewart Publications, London, GB, vol. 1, No. 3, Jan. 1, 2004, pp. 209-217; XP001538494.
International Search Report and Written Opinion based on PCT/US2001/037012 mailed Apr. 17, 2012.
Luo et al., "Adiponectin stimulates human osteoblasts proliferation and differentiation via the MAPK signaling pathway," Experimental Cell Research, Academic Press, US, 309: 1, (Sep. 10, 2005) 99-109, XP005037411.
Ouitas N. et al., "A Novel ex vivo skin model for the assessment of the potential transcutaneous anti-inflammatory effect of topically applied Harpagophytum procumbens extract," International Journal of Pharmaceutics, Elsevier BV, NL, 376: 1-2, (Jul. 6, 2009), 63-68, XP026185227.
Scholz et al., "Analysis of human immunodeficieny virus matrix domain replacements," Virology, Elsevier, Amsterdam, NL. 371: 2, (Nov. 8, 2007) 322-335, XP022439785.
Xie H. et al., "Apelin in and its receptor are expressed in human obsteoblasts," Regulatory Peptides, Elsevier Science B.V., NL, 134: 2-3, (May 15, 2006), 118-125, XP27895144.
Zhang W. et al., "Bone-Targeted Overespression of Bcl-2 Increases Osteoblast Adhesion and Differentiation and Inhibits of Mineralization In Vitro," Calcified Tissue International, Springer-Verlag, NE, 80: 2, (Feb. 2, 2007), 111-122.
European Office Action dated Jul. 14, 2014, issued in Application No. 10 755 291.1-1406.
Japanese Notice of Reasons for Rejection dated Aug. 28, 2014, issued in Application No. 2012-508768.
Coutlee et al., "Nonisotopic Detection of RNA in an Enzyme Immunoassay Using a Monoclonal Antibody against DNA-RNA Hybrids." Analytical Biochemistry 181, 153-162 (1989).
European Office Action dated Jul. 4, 2014, issued in Application No. 09 752 940.8-1403.
Japanese Office Action dated Jun. 30, 2014, issued in Application No. 2011-548258.
Chinese Office Action dated May 4, 2014, issued in Application No. 200980143682.9, English translation.

\* cited by examiner

SEQUENCE LISTING

<160> NUMBER OF SEQ ID NOS: 129

<210> SEQ ID NO 1
<211> LENGTH: 33
<212> TYPE: DNA
<213> ORGANISM: HPV

<400> SEQUENCE: 1
gtacagatgg taccgggggtt gtagaagtat ctg      33

```
<210> SEQ ID NO 2
<211> LENGTH: 31
<212> TYPE: DNA
<213> ORGANISM: HPV

<400> SEQUENCE: 2
ctgcaacaag acatacatcg accggtccac c                              31

<210> SEQ ID NO 3
<211> LENGTH: 31
<212> TYPE: DNA
<213> ORGANISM: HPV

<400> SEQUENCE: 3
gaagtaggtg aggctgcatg tgaagtggta g                              31

<210> SEQ ID NO 4
<211> LENGTH: 33
<212> TYPE: DNA
<213> ORGANISM: HPV

<400> SEQUENCE: 4
cagctctgtg cataactgtg gtaactttct ggg                            33

<210> SEQ ID NO 5
<211> LENGTH: 33
<212> TYPE: DNA
<213> ORGANISM: HPV

<400> SEQUENCE: 5
gaggtcttct ccaacatgct atgcaacgtc ctg                            33

<210> SEQ ID NO 6
<211> LENGTH: 33
<212> TYPE: DNA
<213> ORGANISM: HPV

<400> SEQUENCE: 6
gtgtaggtgc atgctctata ggtacatcag gcc                            33

<210> SEQ ID NO 7
<211> LENGTH: 33
<212> TYPE: DNA
<213> ORGANISM: HPV

<400> SEQUENCE: 7
caatgccgag cttagttcat gcaatttccg agg                            33

<210> SEQ ID NO 8
<211> LENGTH: 33
<212> TYPE: DNA
<213> ORGANISM: HPV

<400> SEQUENCE: 8
gaagtagtag ttgcagacgc ccctaaaggt tgc                            33

<210> SEQ ID NO 9
<211> LENGTH: 30
<212> TYPE: DNA
<213> ORGANISM: HPV

<400> SEQUENCE: 9
gaacgcgatg gtacaggcac tgcagggtcc                                30
```

<210> SEQ ID NO 10
<211> LENGTH: 24
<212> TYPE: DNA
<213> ORGANISM: HPV

<400> SEQUENCE: 10
gaacgcgatg gtacaggcac tgca                                          24

<210> SEQ ID NO 11
<211> LENGTH: 24
<212> TYPE: DNA
<213> ORGANISM: HPV

<400> SEQUENCE: 11
acgcccaccc aatggaatgt accc                                          24

<210> SEQ ID NO 12
<211> LENGTH: 32
<212> TYPE: DNA
<213> ORGANISM: HPV

<400> SEQUENCE: 12
tctgcgtcgt tggagtcgtt cctgtcgtgc tc                                 32

<210> SEQ ID NO 13
<211> LENGTH: 36
<212> TYPE: DNA
<213> ORGANISM: HPV

<400> SEQUENCE: 13
ttattattac tacatacatt gccgccatgt tcgcca                             36

<210> SEQ ID NO 14
<211> LENGTH: 46
<212> TYPE: DNA
<213> ORGANISM: HPV

<400> SEQUENCE: 14
ttattattat gttgccctct gtgcccccgt tgtctatagc ctccgt                  46

<210> SEQ ID NO 15
<211> LENGTH: 38
<212> TYPE: DNA
<213> ORGANISM: HPV

<400> SEQUENCE: 15
ttattattag gagcagtgcc caaaagatta aagtttgc                           38

<210> SEQ ID NO 16
<211> LENGTH: 37
<212> TYPE: DNA
<213> ORGANISM: HPV

<400> SEQUENCE: 16
ttattattac acggtgctgg aatacggtga gggggtg                            37

<210> SEQ ID NO 17
<211> LENGTH: 33
<212> TYPE: DNA
<213> ORGANISM: HPV

<400> SEQUENCE: 17
ttattattaa cgcccaccca atggaatgta ccc                                33

<210> SEQ ID NO 18
<211> LENGTH: 35
<212> TYPE: DNA
<213> ORGANISM: HPV

<400> SEQUENCE: 18
ttattattaa tagtattgtg gtgtgtttct cacat                              35

<210> SEQ ID NO 19
<211> LENGTH: 30
<212> TYPE: DNA
<213> ORGANISM: HPV

<400> SEQUENCE: 19
ttattattag ttggagtcgt tcctgtcgtg                                    30

<210> SEQ ID NO 20
<211> LENGTH: 31
<212> TYPE: DNA
<213> ORGANISM: HPV

<400> SEQUENCE: 20
ttattattac ggaatttcat tttggggctc t                                  31

<210> SEQ ID NO 21
<211> LENGTH: 33
<212> TYPE: DNA
<213> ORGANISM: HPV

<400> SEQUENCE: 21
gctcgaaggt cgtctgctga gctttctact act                                33

<210> SEQ ID NO 22
<211> LENGTH: 32
<212> TYPE: DNA
<213> ORGANISM: HPV

<400> SEQUENCE: 22
gcgccatcct gtaatgcact tttccacaaa gc                                 32

<210> SEQ ID NO 23
<211> LENGTH: 31
<212> TYPE: DNA
<213> ORGANISM: HPV

<400> SEQUENCE: 23
tagtgctagg tgtagtggac gcaggaggtg g                                  31

<210> SEQ ID NO 24
<211> LENGTH: 32
<212> TYPE: DNA
<213> ORGANISM: HPV

<400> SEQUENCE: 24
ggtcacaaca tgtattacac tgccctcggt ac                                 32

<210> SEQ ID NO 25
<211> LENGTH: 31
<212> TYPE: DNA
<213> ORGANISM: HPV

<400> SEQUENCE: 25

```
cctacgtctg cgaagtcttt cttgccgtgc c                                31
```

<210> SEQ ID NO 26
<211> LENGTH: 34
<212> TYPE: DNA
<213> ORGANISM: HPV

<400> SEQUENCE: 26

```
ctgcattgtc actactatcc ccaccactac tttg                             34
```

<210> SEQ ID NO 27
<211> LENGTH: 32
<212> TYPE: DNA
<213> ORGANISM: HPV

<400> SEQUENCE: 27

```
ccacaaggca cattcataca tacacgcacg ca                               32
```

<210> SEQ ID NO 28
<211> LENGTH: 33
<212> TYPE: DNA
<213> ORGANISM: HPV

<400> SEQUENCE: 28

```
gttctaaggt cctctgccga gctctctact gta                              33
```

<210> SEQ ID NO 29
<211> LENGTH: 36
<212> TYPE: DNA
<213> ORGANISM: HPV

<400> SEQUENCE: 29

```
ttattattat gcggttttgg gggtcgacgt ggaggc                           36
```

<210> SEQ ID NO 30
<211> LENGTH: 36
<212> TYPE: DNA
<213> ORGANISM: HPV

<400> SEQUENCE: 30

```
ttattattaa gacctgcccc ctaagggtac atagcc                           36
```

<210> SEQ ID NO 31
<211> LENGTH: 49
<212> TYPE: DNA
<213> ORGANISM: HPV

<400> SEQUENCE: 31

```
ttattattac agcattgcag cctttttgtt acttgcttgt aatagctcc             49
```

<210> SEQ ID NO 32
<211> LENGTH: 34
<212> TYPE: DNA
<213> ORGANISM: HPV

<400> SEQUENCE: 32

```
ttattattaa tcctgtaatg cactttttcca caaa                            34
```

<210> SEQ ID NO 33
<211> LENGTH: 31
<212> TYPE: DNA
<213> ORGANISM: HPV

<400> SEQUENCE: 33

```
ttattattag cctggtcaca acatgtatta c                              31

<210> SEQ ID NO 34
<211> LENGTH: 33
<212> TYPE: DNA
<213> ORGANISM: HPV

<400> SEQUENCE: 34
ttattattac aggatctaat tcattctgag gtt                            33

<210> SEQ ID NO 35
<211> LENGTH: 27
<212> TYPE: DNA
<213> ORGANISM: HPV

<400> SEQUENCE: 35
tgcggttttg ggggtcgacg tggaggc                                   27

<210> SEQ ID NO 36
<211> LENGTH: 33
<212> TYPE: DNA
<213> ORGANISM: HPV

<400> SEQUENCE: 36
ggcgcaacca cataacacac agaaccacaa aac                            33

<210> SEQ ID NO 37
<211> LENGTH: 33
<212> TYPE: DNA
<213> ORGANISM: HPV

<400> SEQUENCE: 37
gttctacacg ggtttgcagc acgatcaaca acg                            33

<210> SEQ ID NO 38
<211> LENGTH: 32
<212> TYPE: DNA
<213> ORGANISM: HPV

<400> SEQUENCE: 38
cgctgcttgt ggtggtcggt tatcgttgtc tg                             32

<210> SEQ ID NO 39
<211> LENGTH: 32
<212> TYPE: DNA
<213> ORGANISM: HPV

<400> SEQUENCE: 39
gacgtagtgt cgcctcacat ttacaacagg ac                             32

<210> SEQ ID NO 40
<211> LENGTH: 30
<212> TYPE: DNA
<213> ORGANISM: HPV

<400> SEQUENCE: 40
ctcgcttggt ggggttgtag gggagctcgg                                30

<210> SEQ ID NO 41
<211> LENGTH: 30
<212> TYPE: DNA
<213> ORGANISM: HPV
```

```
<400> SEQUENCE: 41
gctgtagttg tcgcagagta tcccgtgagg                                    30

<210> SEQ ID NO 42
<211> LENGTH: 33
<212> TYPE: DNA
<213> ORGANISM: HPV

<400> SEQUENCE: 42
gtgagcctgt gttatatgta gtgcccgaat ccc                                33

<210> SEQ ID NO 43
<211> LENGTH: 31
<212> TYPE: DNA
<213> ORGANISM: HPV

<400> SEQUENCE: 43
ccacctcctg cgtccactac acctagcact a                                  31

<210> SEQ ID NO 44
<211> LENGTH: 32
<212> TYPE: DNA
<213> ORGANISM: HPV

<400> SEQUENCE: 44
tgcgtgcgtg tatgtatgaa tgtgccttgt gg                                 32

<210> SEQ ID NO 45
<211> LENGTH: 30
<212> TYPE: DNA
<213> ORGANISM: HPV

<400> SEQUENCE: 45
aattagcgca ttgccccgtc caacgtcccg                                    30

<210> SEQ ID NO 46
<211> LENGTH: 33
<212> TYPE: DNA
<213> ORGANISM: HPV

<400> SEQUENCE: 46
cgccgtgcac gtgtagccac catatttaat cac                                33

<210> SEQ ID NO 47
<211> LENGTH: 32
<212> TYPE: DNA
<213> ORGANISM: HPV

<400> SEQUENCE: 47
cgaattgtgt gaggtgctgg aagaatcggt gc                                 32

<210> SEQ ID NO 48
<211> LENGTH: 32
<212> TYPE: DNA
<213> ORGANISM: HPV

<400> SEQUENCE: 48
gatcgttcac aacttttacc tgcaccggat cc                                 32

<210> SEQ ID NO 49
<211> LENGTH: 33
<212> TYPE: DNA
<213> ORGANISM: HPV
```

```
<400> SEQUENCE: 49
ctaggttctc tagatgtttg tctccagcac ccc                              33

<210> SEQ ID NO 50
<211> LENGTH: 31
<212> TYPE: DNA
<213> ORGANISM: HPV

<400> SEQUENCE: 50
ctgtcggtat tgtctgtgtc gctgatgtgt g                                31

<210> SEQ ID NO 51
<211> LENGTH: 32
<212> TYPE: DNA
<213> ORGANISM: HPV

<400> SEQUENCE: 51
gatacacaca catttgcagc ccggtccaca ca                               32

<210> SEQ ID NO 52
<211> LENGTH: 32
<212> TYPE: DNA
<213> ORGANISM: HPV

<400> SEQUENCE: 52
ggtggcaaag gacgtatgtg agtgcagagg ac                               32

<210> SEQ ID NO 53
<211> LENGTH: 33
<212> TYPE: DNA
<213> ORGANISM: HPV

<400> SEQUENCE: 53
gcgttgcgga ggggtatgat agttgctcag aag                              33

<210> SEQ ID NO 54
<211> LENGTH: 31
<212> TYPE: DNA
<213> ORGANISM: HPV

<400> SEQUENCE: 54
gtctaggcgt gtaggaggaa acaagatggg g                                31

<210> SEQ ID NO 55
<211> LENGTH: 38
<212> TYPE: DNA
<213> ORGANISM: HPV

<400> SEQUENCE: 55
ctgaacacag cagttctcta taccaatggc gctatttc                         38

<210> SEQ ID NO 56
<211> LENGTH: 34
<212> TYPE: DNA
<213> ORGANISM: HPV

<400> SEQUENCE: 56
ttggttgccc ctgagcagtc ggaccctatg gata                             34

<210> SEQ ID NO 57
<211> LENGTH: 42
<212> TYPE: DNA
```

```
<213> ORGANISM: HPV

<400> SEQUENCE: 57
gcgccgcatt gctgcacctc gtttatatag cagggcattt tc                42

<210> SEQ ID NO 58
<211> LENGTH: 31
<212> TYPE: DNA
<213> ORGANISM: HPV

<400> SEQUENCE: 58
cctggcgcat gtcatacaca ccacattact c                            31

<210> SEQ ID NO 59
<211> LENGTH: 30
<212> TYPE: DNA
<213> ORGANISM: HPV

<400> SEQUENCE: 59
cacgaagtgt cagtgcacag tatgccttgc                              30

<210> SEQ ID NO 60
<211> LENGTH: 40
<212> TYPE: DNA
<213> ORGANISM: HPV

<400> SEQUENCE: 60
gccatgtact tcacaaactg ttaatactgg tgattgtccc                   40

<210> SEQ ID NO 61
<211> LENGTH: 31
<212> TYPE: DNA
<213> ORGANISM: HPV

<400> SEQUENCE: 61
cctacacagt acaagtggag gccatcaccc g                            31

<210> SEQ ID NO 62
<211> LENGTH: 39
<212> TYPE: DNA
<213> ORGANISM: HPV

<400> SEQUENCE: 62
gtctgacaca tactgttgta acccatagtt aaacacagg                    39

<210> SEQ ID NO 63
<211> LENGTH: 41
<212> TYPE: DNA
<213> ORGANISM: HPV

<400> SEQUENCE: 63
gctgtctccc tgtcttcctg tgtattgttt ataagtgtat t                 41

<210> SEQ ID NO 64
<211> LENGTH: 44
<212> TYPE: DNA
<213> ORGANISM: HPV

<400> SEQUENCE: 64
gtacagcact aaaatggagt ttggtgtgtt actatagtgc atac              44

<210> SEQ ID NO 65
<211> LENGTH: 16
```

<212> TYPE: DNA
<213> ORGANISM: HPV

<400> SEQUENCE: 65
actccaacga cgcaga                                        16

<210> SEQ ID NO 66
<211> LENGTH: 17
<212> TYPE: DNA
<213> ORGANISM: HPV

<400> SEQUENCE: 66
ttttgtggtt ctgtgtg                                       17

<210> SEQ ID NO 67
<211> LENGTH: 14
<212> TYPE: DNA
<213> ORGANISM: HPV

<400> SEQUENCE: 67
ttatgtggtt gcgc                                          14

<210> SEQ ID NO 68
<211> LENGTH: 15
<212> TYPE: DNA
<213> ORGANISM: HPV

<400> SEQUENCE: 68
cgttgttgat cgtgc                                         15

<210> SEQ ID NO 69
<211> LENGTH: 15
<212> TYPE: DNA
<213> ORGANISM: HPV

<400> SEQUENCE: 69
tgcaaacccg tgtag                                         15

<210> SEQ ID NO 70
<211> LENGTH: 16
<212> TYPE: DNA
<213> ORGANISM: HPV

<400> SEQUENCE: 70
cagacaacga taaccg                                        16

<210> SEQ ID NO 71
<211> LENGTH: 15
<212> TYPE: DNA
<213> ORGANISM: HPV

<400> SEQUENCE: 71
accaccacaa gcagc                                         15

<210> SEQ ID NO 72
<211> LENGTH: 17
<212> TYPE: DNA
<213> ORGANISM: HPV

<400> SEQUENCE: 72
gtcctgttgt aaatgtg                                       17

<210> SEQ ID NO 73

```
<211> LENGTH: 15
<212> TYPE: DNA
<213> ORGANISM: HPV

<400> SEQUENCE: 73
aggcgacact acgtc                                                     15

<210> SEQ ID NO 74
<211> LENGTH: 15
<212> TYPE: DNA
<213> ORGANISM: HPV

<400> SEQUENCE: 74
cgagctcccc tacaa                                                     15

<210> SEQ ID NO 75
<211> LENGTH: 13
<212> TYPE: DNA
<213> ORGANISM: HPV

<400> SEQUENCE: 75
ccccaccaag cga                                                       13

<210> SEQ ID NO 76
<211> LENGTH: 15
<212> TYPE: DNA
<213> ORGANISM: HPV

<400> SEQUENCE: 76
cctcacggga tactc                                                     15

<210> SEQ ID NO 77
<211> LENGTH: 15
<212> TYPE: DNA
<213> ORGANISM: HPV

<400> SEQUENCE: 77
tgcgacaact acagc                                                     15

<210> SEQ ID NO 78
<211> LENGTH: 14
<212> TYPE: DNA
<213> ORGANISM: HPV

<400> SEQUENCE: 78
ggattcgggc acta                                                      14

<210> SEQ ID NO 79
<211> LENGTH: 18
<212> TYPE: DNA
<213> ORGANISM: HPV

<400> SEQUENCE: 79
catataacac aggctcac                                                  18

<210> SEQ ID NO 80
<211> LENGTH: 18
<212> TYPE: DNA
<213> ORGANISM: HPV

<400> SEQUENCE: 80
tagtgctagg tgtagtgg                                                  18
```

```
<210> SEQ ID NO 81
<211> LENGTH: 13
<212> TYPE: DNA
<213> ORGANISM: HPV

<400> SEQUENCE: 81
acgcaggagg tgg                                                        13

<210> SEQ ID NO 82
<211> LENGTH: 16
<212> TYPE: DNA
<213> ORGANISM: HPV

<400> SEQUENCE: 82
tacatacacg cacgca                                                     16

<210> SEQ ID NO 83
<211> LENGTH: 16
<212> TYPE: DNA
<213> ORGANISM: HPV

<400> SEQUENCE: 83
ccacaaggca cattca                                                     16

<210> SEQ ID NO 84
<211> LENGTH: 17
<212> TYPE: DNA
<213> ORGANISM: HPV

<400> SEQUENCE: 84
gctacacgtg cacggcg                                                    17

<210> SEQ ID NO 85
<211> LENGTH: 17
<212> TYPE: DNA
<213> ORGANISM: HPV

<400> SEQUENCE: 85
gtgattaaat atggtgg                                                    17

<210> SEQ ID NO 86
<211> LENGTH: 13
<212> TYPE: DNA
<213> ORGANISM: HPV

<400> SEQUENCE: 86
gggacgttgg acg                                                        13

<210> SEQ ID NO 87
<211> LENGTH: 14
<212> TYPE: DNA
<213> ORGANISM: HPV

<400> SEQUENCE: 87
ggcaatgcgc taat                                                       14

<210> SEQ ID NO 88
<211> LENGTH: 15
<212> TYPE: DNA
<213> ORGANISM: HPV

<400> SEQUENCE: 88
caccgattct tccag                                                      15
```

```
<210> SEQ ID NO 89
<211> LENGTH: 16
<212> TYPE: DNA
<213> ORGANISM: HPV

<400> SEQUENCE: 89
cacctcacac aattcg                                                     16

<210> SEQ ID NO 90
<211> LENGTH: 13
<212> TYPE: DNA
<213> ORGANISM: HPV

<400> SEQUENCE: 90
ggatccggtg cag                                                        13

<210> SEQ ID NO 91
<211> LENGTH: 19
<212> TYPE: DNA
<213> ORGANISM: HPV

<400> SEQUENCE: 91
gtaaaagttg tgaacgatc                                                  19

<210> SEQ ID NO 92
<211> LENGTH: 14
<212> TYPE: DNA
<213> ORGANISM: HPV

<400> SEQUENCE: 92
ggtgctggag acaa                                                       14

<210> SEQ ID NO 93
<211> LENGTH: 17
<212> TYPE: DNA
<213> ORGANISM: HPV

<400> SEQUENCE: 93
acatctagag aacctag                                                    17

<210> SEQ ID NO 94
<211> LENGTH: 15
<212> TYPE: DNA
<213> ORGANISM: HPV

<400> SEQUENCE: 94
cacacatcag cgaca                                                      15

<210> SEQ ID NO 95
<211> LENGTH: 16
<212> TYPE: DNA
<213> ORGANISM: HPV

<400> SEQUENCE: 95
cagacaatac cgacag                                                     16

<210> SEQ ID NO 96
<211> LENGTH: 13
<212> TYPE: DNA
<213> ORGANISM: HPV

<400> SEQUENCE: 96
tgtgtggacc ggg                                                        13
```

```
<210> SEQ ID NO 97
<211> LENGTH: 18
<212> TYPE: DNA
<213> ORGANISM: HPV

<400> SEQUENCE: 97
ctgcaaatgt gtgtgtat                                              18

<210> SEQ ID NO 98
<211> LENGTH: 17
<212> TYPE: DNA
<213> ORGANISM: HPV

<400> SEQUENCE: 98
gtcctctgca ctcacat                                               17

<210> SEQ ID NO 99
<211> LENGTH: 14
<212> TYPE: DNA
<213> ORGANISM: HPV

<400> SEQUENCE: 99
acgtcctttg ccac                                                  14

<210> SEQ ID NO 100
<211> LENGTH: 19
<212> TYPE: DNA
<213> ORGANISM: HPV

<400> SEQUENCE: 100
ttctgagcaa ctatcatac                                             19

<210> SEQ ID NO 101
<211> LENGTH: 12
<212> TYPE: DNA
<213> ORGANISM: HPV

<400> SEQUENCE: 101
ccctccgcaa cg                                                    12

<210> SEQ ID NO 102
<211> LENGTH: 15
<212> TYPE: DNA
<213> ORGANISM: HPV

<400> SEQUENCE: 102
ccccatcttg tttcc                                                 15

<210> SEQ ID NO 103
<211> LENGTH: 16
<212> TYPE: DNA
<213> ORGANISM: HPV

<400> SEQUENCE: 103
tcctacacgc ctagac                                                16

<210> SEQ ID NO 104
<211> LENGTH: 20
<212> TYPE: DNA
<213> ORGANISM: HPV

<400> SEQUENCE: 104
```
tatagagaac tgctgtgttc                                                    20

<210> SEQ ID NO 105
<211> LENGTH: 15
<212> TYPE: DNA
<213> ORGANISM: HPV

<400> SEQUENCE: 105
gaaatagcgc cattg                                                         15

<210> SEQ ID NO 106
<211> LENGTH: 14
<212> TYPE: DNA
<213> ORGANISM: HPV

<400> SEQUENCE: 106
ctcaggggca acca                                                          14

<210> SEQ ID NO 107
<211> LENGTH: 16
<212> TYPE: DNA
<213> ORGANISM: HPV

<400> SEQUENCE: 107
atccataggg tccgac                                                        16

<210> SEQ ID NO 108
<211> LENGTH: 11
<212> TYPE: DNA
<213> ORGANISM: HPV

<400> SEQUENCE: 108
caatgcggcg c                                                             11

<210> SEQ ID NO 109
<211> LENGTH: 16
<212> TYPE: DNA
<213> ORGANISM: HPV

<400> SEQUENCE: 109
tataaacgag gtgcag                                                        16

<210> SEQ ID NO 110
<211> LENGTH: 15
<212> TYPE: DNA
<213> ORGANISM: HPV

<400> SEQUENCE: 110
gaaaatgccc tgcta                                                         15

<210> SEQ ID NO 111
<211> LENGTH: 12
<212> TYPE: DNA
<213> ORGANISM: HPV

<400> SEQUENCE: 111
acatgcgcca gg                                                            12

<210> SEQ ID NO 112
<211> LENGTH: 19
<212> TYPE: DNA
<213> ORGANISM: HPV

<400> SEQUENCE: 112

```
gagtaatgtg gtgtgtatg                                           19

<210> SEQ ID NO 113
<211> LENGTH: 15
<212> TYPE: DNA
<213> ORGANISM: HPV

<400> SEQUENCE: 113
gcaaggcata ctgtg                                               15

<210> SEQ ID NO 114
<211> LENGTH: 15
<212> TYPE: DNA
<213> ORGANISM: HPV

<400> SEQUENCE: 114
cactgacact tcgtg                                               15

<210> SEQ ID NO 115
<211> LENGTH: 18
<212> TYPE: DNA
<213> ORGANISM: HPV

<400> SEQUENCE: 115
ggacaatcac cagtatta                                            18

<210> SEQ ID NO 116
<211> LENGTH: 18
<212> TYPE: DNA
<213> ORGANISM: HPV

<400> SEQUENCE: 116
agtttgtgaa gtacatgg                                            18

<210> SEQ ID NO 117
<211> LENGTH: 12
<212> TYPE: DNA
<213> ORGANISM: HPV

<400> SEQUENCE: 117
cgggtgatgg cc                                                  12

<210> SEQ ID NO 118
<211> LENGTH: 18
<212> TYPE: DNA
<213> ORGANISM: HPV

<400> SEQUENCE: 118
ccacttgtac tgtgtagg                                            18

<210> SEQ ID NO 119
<211> LENGTH: 18
<212> TYPE: DNA
<213> ORGANISM: HPV

<400> SEQUENCE: 119
ctgtgtttaa ctatgggt                                            18

<210> SEQ ID NO 120
<211> LENGTH: 20
<212> TYPE: DNA
<213> ORGANISM: HPV
```

```
<400> SEQUENCE: 120
tacaacagta tgtgtcagac                                          20

<210> SEQ ID NO 121
<211> LENGTH: 16
<212> TYPE: DNA
<213> ORGANISM: HPV

<400> SEQUENCE: 121
aagacaggga gacagc                                              16

<210> SEQ ID NO 122
<211> LENGTH: 19
<212> TYPE: DNA
<213> ORGANISM: HPV

<400> SEQUENCE: 122
cttataaaca atacacagg                                           19

<210> SEQ ID NO 123
<211> LENGTH: 20
<212> TYPE: DNA
<213> ORGANISM: HPV

<400> SEQUENCE: 123
atgcactata gtaacacacc                                          20

<210> SEQ ID NO 124
<211> LENGTH: 19
<212> TYPE: DNA
<213> ORGANISM: HPV

<400> SEQUENCE: 124
actccatttt agtgctgta                                           19

<210> SEQ ID NO 125
<211> LENGTH: 24
<212> TYPE: DNA
<213> ORGANISM: HPV

<400> SEQUENCE: 125
tcaggaccca caggagcgac ccag                                     24

<210> SEQ ID NO 126
<211> LENGTH: 23
<212> TYPE: DNA
<213> ORGANISM: Artificial
<220> FEATURE:
<223> OTHER INFORMATION: Synthetic primer

<400> SEQUENCE: 126
gcaccaaaag agaactgcaa tgt                                      23

<210> SEQ ID NO 127
<211> LENGTH: 24
<212> TYPE: DNA
<213> ORGANISM: Artificial
<220> FEATURE:
<223> OTHER INFORMATION: Synthetic primer

<400> SEQUENCE: 127
catatacctc acgtcgcagt aact                                     24
```

```
<210> SEQ ID NO 128
<211> LENGTH: 20
<212> TYPE: DNA
<213> ORGANISM: HPV

<400> SEQUENCE: 128
tattttatat gacacaatgt                                              20

<210> SEQ ID NO 129
<211> LENGTH: 30
<212> TYPE: DNA
<213> ORGANISM: HPV

<400> SEQUENCE: 129
ggtttgtgct aacaataaat gtatccatag                                   30
```

DETECTION OF NUCLEIC ACIDS BY TARGET-SPECIFIC HYBRID CAPTURE METHOD

This application is a divisional of U.S. patent application Ser. No. 11/269,003, filed Nov. 7, 2005, which in turn is a continuation-in-part of U.S. patent application Ser. No. 11/005,617, filed Dec. 6, 2004, now abandoned, which is a continuation-in-part of U.S. patent application Ser. No. 10/971,251, filed Oct. 20, 2004, now abandoned. The contents of all applications are herein incorporated by reference in their entirety.

FIELD OF INVENTION

This invention relates to the field of nucleic acid detection methods in general and more particularly relates to the detection of nucleic acids by target-specific hybrid capture method.

BACKGROUND OF THE INVENTION

The detection of specific nucleic acid sequences present in a biological sample is important for identifying and classifying microorganisms, diagnosing infectious diseases, detecting and characterizing genetic abnormalities, identifying genetic changes associated with cancer, studying genetic susceptibility to disease, and measuring response to various types of treatment. Common techniques for detecting and quantitating specific nucleic acid sequences are nucleic acid hybridization and target amplification.

Various hybridization methods are available for the detection and study of nucleic acids. In a traditional hybridization method, the nucleic acids to be identified are either in a solution or affixed to a solid carrier. The nucleic acids are detected using labeled nucleic acid probes which are capable of hybridizing to the nucleic acids. Recently, new hybridization methods have been developed to increase the sensitivity and specificity of detection. One example is the Hybrid Capture® method described in U.S. application Ser. No. 07/792,585 and U.S. Pat. No. 6,228,578. Although these new hybridization methods offer significant improvements over the traditional methods, they still lack the ability to fully discriminate between highly homologous nucleic acid sequences.

The polymerase chain reaction (PCR) is the most commonly used target nucleic acid amplification method. However, PCR is limited to some extent when a large number of different targets are to be amplified simultaneously, i.e., multiplex reactions, which may cause not only PCR artifacts such as primer-dimers, but also spurious target amplification. In an attempt to overcome this limitation, consensus primers may be used when a number of targets have homologous regions. However, homology between species is never 100%, and as a result, the primers will have several mismatches with different targets, causing non-uniform amplification. When different amounts of targets are present in a sample, the amplification efficiency of different PCRs also varies, leading to non-uniform and non-specific amplification of different targets.

It is therefore an object of the present invention to provide a method for detecting target nucleic acid sequences which not only provides increased rapidity and sensitivity, but which is also highly specific and capable of discriminating between multiple highly homologous nucleic acid target sequences

SUMMARY OF THE INVENTION

The present invention provides a novel nucleic acid detection method, referred to herein as target-specific HYBRID CAPTURE ("TSHC"). TSHC is a rapid, highly specific, and sensitive method capable of discriminating between and detecting highly homologous nucleic acid target sequences.

One embodiment of the invention relates to a method of detecting and/or quantifying one or more target nucleic acids, comprising the steps of target enrichment, amplification, and detection for the rapid and sensitive detection of the target nucleic acid sequences.

In one embodiment of the claimed method, one or more target nucleic acids are detected by: capturing the target nucleic acids to a solid support by mixing the target nucleic acids, nucleic acid probes complementary to the target nucleic acids, wherein one is RNA and the other is DNA, and a solid support; removing unbound target nucleic acids and nucleic acid probes; amplifying the captured target nucleic acids or nucleic acid probes, forming a plurality of amplicons, where the presence of the amplicons is indicative of the presence of the target nucleic acids; and detecting the target nucleic acids by mixing the target nucleic acids with selectable and distinguishable oligonucleotides which hybridize to a portion of the target nucleic acids, (i.e., capture sequence probes; CSPs) and nucleic acid probes complementary to a different portion of the target nucleic acids (i.e., signal sequence probes; SSPs), wherein either the probe or target is an RNA and the other is DNA, where DNA:RNA hybrids are detected by DNA:RNA hybrid-specific binding agents, which are directly or indirectly labeled, thereby detecting the target nucleic acids. The SSPs are not limited to serving as only a means for producing a signal for detection; but may be used in the target enrichment step by hybridizing to the target nucleic acid, enabling capture with a DNA:RNA hybrid-specific binding agent.

In yet another embodiment, a plurality of target nucleic acids are detected by: hybridizing a plurality of target nucleic acids to nucleic acid probes which are complementary to the target nucleic acids, forming DNA:RNA hybrids; capturing the DNA:RNA hybrids with DNA:RNA hybrid-specific antibodies conjugated to solid supports; removing unbound target nucleic acids and nucleic acid probes; amplifying the captured target nucleic acids or nucleic acid probes, forming a plurality of amplicons, using random primers and DNA polymerase, where the presence of the plurality of amplicons is indicative of the presence of the target nucleic acids; hybridizing nucleic acid probes complementary to a portion of the target nucleic acid sequences, forming DNA:RNA hybrids between targets and probes; hybridizing oligonucleotides conjugated to a solid support to a different portion of the target nucleic acids, wherein the solid support is selectable; selecting the oligonucleotide complexes; and detecting the plurality of target nucleic acids by binding DNA:RNA hybrid-specific binding agents to the DNA:RNA hybrids.

In a further embodiment, one or more target DNAs are detected by a multiplex method having the steps of: hybridizing a plurality of target DNAs to RNA probes which are complementary to the target DNAs, forming DNA:RNA hybrids; capturing the DNA:RNA hybrids with DNA:RNA hybrid-specific antibodies which are conjugated to beads; removing unbound nucleic acids and nucleic acid probes by washing excess nucleic acids and probes; isothermally amplifying the target DNAs using random primers and DNA polymerase, forming a plurality of amplicons; hybridizing RNA probes complementary to a portion of the target DNAs (i.e., SSPs), forming DNA:RNA hybrids; hybridizing specific DNA oligonucleotides to a different portion of the target DNAs, wherein the DNA oligonucleotides are conjugated to selectable beads; and detecting the plurality of target DNAs by binding detectably labeled DNA:RNA hybrid-specific antibodies to the DNA:RNA hybrids and selecting target DNA using selectable oligonucleotide-conjugated beads (i.e., CSPs), wherein the DNA:RNA hybrid-specific antibodies are detectably and distinguishably labeled. The presence of each target is detected by the labeled DNA:RNA antibody through SSPs which form DNA:RNA hybrids with the target, while the various targets are separated or selected based on the oligonucleotide-conjugated bead (i.e., CSP). The presence of amplicon and DNA:RNA hybrids is indicative of the presence of the target DNAs.

DETAILED DESCRIPTION OF THE INVENTION

The invention provides a method for enriching, amplifying, and detecting the presence of a nucleic acid or a plurality of nucleic acids in test samples. More specifically, the invention provides a highly specific and sensitive method which is capable of discriminating between and detecting highly homologous nucleic acid sequences.

One embodiment of the invention is directed to rapid, sensitive methods for multiplex detection of target nucleic acid sequences, where a plurality of different target nucleic acid sequences may be detected simultaneously. This method may be automated. The method essentially comprises three steps: target enrichment; target amplification; and target detection, which presents a semiquantitative or qualitative approach for nucleic acid diagnostics. This embodiment of the invention may be performed in multiplex format detecting target nucleic acid sequences in purified or unpurified samples, where a concentration of target may be as low as about 50 copies or fewer per milliliter of sample to about 100 copies of target, to as great as $10^8$ copies per milliliter. Detection of individual pathogens or targets in biological samples, such as but not limited to HSV and HPV types, may be performed in multiplex, preferably but not limited to, 50-plexes.

As is beneficial, this multiplex method of detecting a plurality of target nucleic acid sequences is a relatively rapid, sensitive, and accurate method having two levels of specificity which is an advantageous feature for clinical assays. The two levels of specificity are achieved in the target enrichment and detection steps by using sequences specific for the target.

Target enrichment is the first step which prepares the sample for amplification by separating non-specific nucleic acids and contaminants from the specific target. The presence of non-specific or undesirable nucleic acid sequences decreases the sensitivity of target amplification by interfering with amplification and detection. The target enrichment step purifies the sample from possible inhibitors and eliminates non-specific nucleic acids thereby providing the first level of specificity. Eliminating non-specific nucleic acids allows efficient amplification in the isothermal amplification step and thereby minimizes the competition between homologous targets. Target enrichment also denatures double-stranded targets, creating single-stranded DNA for efficient amplification. Various reagents may be used in the target enrichment step in order to improve target capture. For example, subtilisins may be used to improve target capture, especially in clinical samples that are bloody. Subtilisins, or carbonyl hydrolases, are alkaline proteases that are secreted by members of the genus *Bacillus*. When target nucleic acids are captured by beads, the presence of subtilisin causes the beads to form tight pellets, thereby enhancing the ease of washing away unbound or undesirable materials. Furthermore, the target enrichment step also concentrates target nucleic acid in a small volume.

Enrichment of the target is achieved by mixing a target nucleic acid, a DNA:RNA hybrid-specific binding agent, such as a nucleic acid probe which is complementary to the target nucleic acid, for example, a signal sequence probe, and a solid support, where the target nucleic acid and the DNA:RNA hybrid-specific binding agent hybridize to form a DNA:RNA hybrid on a solid support, and removing any nucleic acids which do not form a DNA:RNA hybrid or are not captured to a solid support.

In particular, separation of the desired target nucleic acid and the non-specific nucleic acid is accomplished by the formation of DNA:RNA hybrids that are captured on a solid phase or solid support, such as for example, paramagnetic beads modified with DNA:RNA hybrid-specific binding agents such as, but not limited to, antibodies specific for DNA:RNA hybrids (e.g., HYBRID CAPTURE antibody, HC-Ab), monoclonal or polyclonal antibodies, or fragments thereof, proteins, catalytically inactive RNase H, nucleic acids, nucleic acid aptamers, or oligonucleotides having the ability to bind and form a triplex structure. The binding affinity of RNase H for DNA:RNA hybrids in the absence of $Mg^{2+}$ and catalysis via surface plasmon resonance is reported by Haruki, et al. ["Kinetic and stoichiometric analysis for the binding of *Escherichia coli* ribonuclease HI to RNA-DNA hybrids using surface plasmon resonance" *J. Biol. Chem.* 272:22015-22022, 1997, incorporated by reference]. This target enrichment step may be carried out on any solid support, such as on microtiter plates, microchips, beads, paramagnetic/non-paramagnetic beads or any of the previously mentioned solid phases. For example, target DNA, RNA probe, or set of different RNA probes (if in a multiplex reaction), and beads bound with conjugated DNA:RNA HC-antibodies are mixed. The target DNAs and RNA probes form DNA:RNA hybrids. The DNA:RNA HC-antibodies are conjugated to solid supports, such as paramagnetic beads. Once the DNA:RNA hybrids are captured onto solid supports, all unbound nucleic acid sequences and contaminants are washed away, preferably by repeated washes using buffers which do not degrade or affect the hybrids.

As an alternative or in addition to using the DNA:RNA hybrid-specific antibodies, oligonucleotides or polynucleotides of any length that are complementary to the targets conjugated to a solid phase may be used for capturing target nucleic acid sequences. For example, oligonucleotides or probes which recognize a specific HPV type may be conjugated to a solid phase, such as a plate, chip, or bead. Several beads conjugated to specific and known probes form a bead set. For example, each bead set is specific for one HPV type. In a multiplex format, multiple bead sets which identify various HPV types, one HPV type per bead set, may be used. Oligonucleotides useful in the capturing the target nucleic acid may be partial or complete, locked nucleic acids (LNA), peptide nucleic acids (PNA), or have other modifications [*Current Protocols in Nucleic Acid Chemistry*, Eds. Serge L. Beaucage, et al., John Wiley & Sons© 2004]. The nucleic acid probe may have a length up to about 100% of the target nucleic acid length, and range from about 50 bases to about 10 kilobases in length. The target nucleic acid may be either DNA or RNA. If the target nucleic acid is RNA, then cDNA may be generated from the RNA target by any of the commonly known methods, or the target RNA may be captured by a DNA probe, where hybridized DNA probe will be amplified and detected.

The target enrichment step is not limited by the embodiments described herein. One skilled in the art will understand how to purify a target nucleic acid in a sample such that contaminants, inhibitors and other non-specific nucleic acids are removed or eliminated from the sample based upon the principles described herein. Sample preparations are known and understood in the art through commercially available methods and kits, such as plasmid mini- or maxi-preparation kits, gel extraction kits, and DNA and RNA purification kits. These may be used to facilitate the target enrichment step in certain circumstances where lower sensitivity is acceptable.

After target enrichment, the sample undergoes nucleic acid amplification. Isothermal target amplification of nucleic acids using oligonucleotide primers of random sequences and a DNA polymerase with strand-displacing activity addresses many of the limitations such as, but not inclusive, of limited multiplex capabilities and non-uniform amplification of multiplex PCR. The amplified sequences, or amplicons, are identified through hybridization to the sequence specific oligonucleotides. Amplification may also be performed with the individual targets rather than in multiplex format and amplicons may be combined for the hybridization assay.

DNA polymerase may be used to extend the primers and activate strand displacement. Alternatively, if a DNA probe is used to capture the target RNA, then the hybridized DNA probe is amplified and detected. Another embodiment entails reverse transcribing target RNA to produce cDNA, as the DNA target, which may be captured as described above. This second step preferably uses isothermal amplification of a target nucleic acid. Specifically, oligonucleotide primers of random sequence and a DNA polymerase having strand-displacing activity may be useful in isothermal amplification. In one embodiment, a solid phase or support such as, but not limited to magnetic beads, which has a captured target nucleic acid may be used directly in an amplification mixture. DNA targets may be amplified using any DNA polymerases, (including but not limited to, phi29 DNA polymerase, Bst DNA polymerase, T4 DNA polymerase, T7 DNA polymerase, and DNA Polymerase I), that are primed with random primers.

Random primers may have a specific ratio of dG, dC, dT and dA monomers for optimal efficiency. One or two nucleotide bases could be completely omitted for optimal performance. The random primer pool does not need to include all of the possible sequences. Sequences included in the pool also do not need to be at equimolar concentrations. In fact, random primer pools may include a subset of primer sequences selective for particular diseases. The length may vary from about 4 to about 20 nucleotides, and preferably from about 5 to about 8 nucleotides. Length may depend on the ratio of monomer within the primer. An optimal amplification temperature varies between about 25° C. and about 70° C., preferably about 28° C. to about 40° C., depending on the length of the primers which may be determined by one skilled in the art and without undue experimentation. The optimal temperature could be estimated by using commercially available software that predicts the annealing temperature of the oligonucleotides. One example of such commercially available software is OLIGO™ sVersion 6.0 or 6.41 (Molecular Biology Insights; Cascade, Colo.). For example, the target DNA may be amplified for 2 hours with pentamer primers in combination with phi29 DNA polymerase.

Pentamer primers, for example, are protected from exonuclease degradation by modifications. Phosphorothioate bonds or 2'-O-methyl groups may be included into the structure of the primers. The amplification reaction preferably occurs over 1-3 hours depending on the required sensitivity, which is substantially shorter than the duration of published protocols for phi29 DNA polymerase reactions [Gary J. Vora, et al., *Applied and Environmental Microbiology*, 70 (5): 3047-3054, 2004, incorporated by reference]. A unique formula of reagents combined with the chosen target enrichment step and the target detection step enables the relatively short amplification time.

The target amplification step of the invention preferably utilizes isothermal amplification which enables: amplification of an unlimited number of targets with uniform efficiency; amplification of the entire sequence, not a fragment as is the case in the polymerase chain reaction (PCR); and allows target detection even if a part of the target sequence in the biological sample is removed. For example, the L1 region is often deleted in HPV; however, by using a hybridization probe for the L1 and E regions [M H Einstein and G N Goldberg, *Cancer Invest.* 20:1080-1085, 2002], the deleted sequences may still be detected with the same level of sensitivity, thus allowing detection of the target even though part of the sequence is absent. Multiplex isothermal amplification may be performed at a temperature ranging from about 25° C. to about 40° C. with a reaction time ranging from 1 to 3 hours. Non-limiting examples of isothermal amplification include rolling circle amplification [Lizardi P., Huang X., Zhu Z., Bray-Ward P., Thomas D., Ward D. "Mutation detection and single molecule counting using isothermal rolling circle amplification" *Nat. Genet.* 1998, 19:225-232]; multiple displacement amplification [Little M., et al. "Strand displacement amplification and homogenous real-time detection incorporated in a second generation probe system" *Clin. Chem.* 1999, 45:777-784]; and protein-primed DNA amplification [Blanco M., Lazaro J., de Vega M., Bonnin A., Salas M "Terminal protein-primed DNA amplification" *Proc. Natl. Acad. Sci. USA*, 1994, 91:12198-12202]. Other target amplification embodiments include those where the target is released from the solid support before adding it to the amplification mixture. Non-limiting ways for releasing the target nucleic acid include, alkali treatment, high temperature incubation, and RNaseH treatment. A unique formula of reagents combined with the chosen target enrichment step and the target detection step permits use of the relatively short amplification time. The reagents for isothermal amplification may be performed simultaneously with target amplification, optionally including RNase H, which would increase the number of priming sites on the target DNA. These methods allow denaturation as well as solid support release enabling more efficient target amplification.

The next step involves the detection of individual target nucleic acid sequences within the amplified nucleic acid. The sensitivity and specificity of this step usually depends on the amplification efficiency. The detection and elucidation of the target nucleic acid is performed by hybridizing different portions of the amplified target product, or amplicons, to individual capture sequence probes which are conjugated to a solid support and specific probes complementary to the target sequence forming a target complex. Hybridization of different portions of the target nucleic acid sequence with two probes provides two levels of specificity, ensuring the detection and identification of a specific target in a sample.

Oligonucleotides or capture sequence probes conjugated to a solid support, preferably beads which are selectable, are useful in obtaining one level of specificity. Hybridization of the CSPs to the amplified target nucleic acids followed by subsequent selection of the beads, enables the separation of the target complex from the unbound or partially bound entities. The CSPs are generally added in excessive amounts in order to ensure binding. Preferably, the CSPs and SSPs do not have overlapping sequences; however, it is possible to perform the method in one embodiment where the CSPs and SSPs have overlapping sequences complementary to the target nucleic acid sequence.

Capture sequence probes (CSP) or oligonucleotides may be conjugated or attached to a solid phase, solid support, or solid matrix which includes, for example, polystyrene, polyethylene, polypropylene, polycarbonate or any solid plastic material in the shape of plates, slides, dishes, beads, particles, cups, strands, chips, strips, microplates, and microarrays. A solid phase also includes glass beads, glass test tubes and any other appropriate glass product. A functionalized solid phase such as plastic or glass that has been modified so that the surface contains carboxyl, amino, hydrazide, aldehyde groups, nucleic acid or nucleotide derivatives can also be used. Any solid phase such as plastic, metal, magnetic or glass microparticles, beads, strips, test tubes, slides, strands, chips, microchip or microtiter plates can be used.

Capture sequence probes or oligonucleotides are nucleic acid probes which comprise at least 8 bases, preferably 15 to 100 bases, and more preferably 20 to 40 bases. The capture sequence probes are preferably identifiable, either by their known locations on a solid support, such as a sub-well plate, or when, for example, conjugated to beads, by a distinguishable colored dye. The means for identifying the capture sequence probes are known in the art, and are exemplified in the instant specification.

Hybridization to the sequence specific probes which may be attached to the solid support not only allows for identification of the specific targets, but also provides a second level of specificity to the assay, making it a more reliable clinical assay. If lower sensitivity is required, signal amplification is not necessary and detection using (signal) oligonucleotides or polynucleotides attached to the reporter (biotin, fluorophore, enzyme, etc.) may be used. There may be more than one detection oligonucleotide per target. Both capture and detection oligonucleotides may be additionally modified, e.g., PNA, LNA, etc. Oligonucleotides or nucleic acid probes may have a length ranging from about 15 bases to about 10 kilobases, or up to 100% of the target length.

A signal sequence probe (SSP) may be an unlabeled RNA that is used to form an DNA:RNA hybrid recognized by, for example, a labeled hybrid-specific binding agent during the detection step. Since the SSP is unlabeled, it does not create background noise when unbound to the target, thereby resulting in more specificity. A signal amplified by approximately 400 fold may be achieved if, for example, the size of the RNA signal probe is 8 kilobases (kb) and each antibody binds to 20 bases. As previously described, generally, the signal sequence probe comprise at least 15 bases, but may be up to or greater than about 1000 bases, preferably between about 15 to 100 bases. Other non-limiting examples of a signal sequence probe include labeled RNA probe and labeled DNA probe. Hybridization is not limited to non-overlapping regions, but may in fact include overlapping regions. The detection of the RNA:DNA hybrid complex bound to a solid support may be performed in a multiplex format using, for example, a PE-labeled antibody, carboxylated distinguishable beads, and detected by flow-cytometry.

One embodiment for target (or amplicon) detection utilizes a liquid-based array. Bead arrays are commercially available and in this embodiment, carboxylated polystyrene bead arrays are preferable. Each well of a 96-well plate, for example, has a mixture of bead sets. A 13-plex has 13 bead sets where each bead set has a specific "signature" and the signature is provided by dyes that are inside each bead. The ratio of these dyes is specific for each bead set, and enables differentiation between each of the bead sets. Capture sequence probes (CSPs) or oligonucleotides specific for one target nucleic acid are applied or conjugated to one particular bead set. When the target is hybridized to the bead conjugated CSPs or oligonucleotides, selection of a particular bead set and then detection occurs using the complementary nucleic acid probe and labeled DNA:RNA hybrid-specific binding agent. The selection or separation may be carried out in a flow-cytometer, where the beads proceed one-by-one through two lasers: one of which selects the signature on the bead, while the other detects the target as identified by the labeled DNA:RNA hybrid-specific binding agents. In this way, multiple targets may be differentiated and detected. Additionally, the labeled DNA:RNA reagent allows enhanced signal detection, thereby increasing both the specificity and sensitivity of the assay.

A further embodiment to the liquid-based bead array of the instant invention utilizes sub-well plates. A sub-well plate is a microtiter plate, having, for example, 96 primary wells, where each individual primary well is subdivided into a number of sub-wells. The sub-well plate as a platform for multiplex has been previously described [A. Roda, et al. *Clin. Chem* 46: 1654-1660, 2002, incorporated by reference]. However, the subwell platform, as previously used and described, has limited use because of the "cross-talk" problem between different sub-wells. Whereas, the modified sub-well platform described here essentially eliminates the problem of cross-talk between different subwells by the use of masks. Each sub-well preferably has a known target-specific capture sequence probe attached to the well. Target nucleic acids may be added to the primary well where the target nucleic acid hybridizes to its complementary nucleic acid probe, i.e., signal sequence probe. DNA:RNA hybrids are formed between a portion of the target nucleic acid and the signal sequence probe. The capture sequence probe binds a different portion of the target nucleic acid, thereby capturing the DNA:RNA hybrid to the solid phase. Detection of the target nucleic acid occurs as previously described using complementary nucleic acid probes which hybridizes to the target nucleic acid, and labeled DNA:RNA hybrid-specific antibodies, for example, and by the known capture sequence probe. Signal amplification and the use of a mask which acts as a lid to eliminate the cross-talk between the sub-wells both enable the specific and sensitive detection of target nucleic acids with minimal background noise.

A wide variety of methods are available that may be used for detecting and identifying the target sequence including, but not limited to dot blot hybridization, reverse blot hybridization on nylon membrane, hybridization of slide arrays, chip arrays, bead arrays, arrays on the bottom of a multi-well plates, or the like. Non-limiting examples of solid supports for hybridization include bead arrays (for example, bead array products from commercially available sources), slide arrays, plate arrays (e.g., arrays on the bottom of each well of a microtiter plate), sub-well plates (microtiter plate that has 16-64 small sub-wells within each well), and arrays of electrodes such as the GenOHM system (GeneOhm Sciences, Inc.). Drummond, et al., *Nature Biotech,* 21: 1192-1199 (2003). Different types of reporters may be implemented to generate signals for detection through, for example, fluorescence, chemiluminescence, and gold nanoparticles. As previously discussed, the detector means may include fluorescence, any enzyme-based signal, chemiluminescent or calorimetric signals, light scattering with gold particles, or the like.

In one embodiment, a reporter may be attached to a hybrid-specific binding agent, such as but not limited to, antibodies specific for RNA:DNA hybrids (HC-Ab), proteins, catalytically inactive RNase H, nucleic acids, nucleic acid aptamers, or oligonucleotides having the ability to bind and form a triplex structure. Each labeled binding agent binds a nucleotide segment of the DNA:RNA hybrid, for example, at least 20 nucleotides in length, providing signal amplification.

A further embodiment of the invention for the multiplex detection of a plurality of target DNA in an unpurified sample comprises the following steps: 1) denaturing target DNA to create a single-stranded target sequence; 2) adding RNA probes and magnetic beads, where the beads have been previously conjugated to antibodies that are specific for hybrids; 3) removing any unbound targets and contaminants by washing; 4) performing the isothermal amplification of the captured targets for a relatively short period of time, such as for example 1-3 hours, in the presence of DNA polymerase and other reagents to initiate amplification and formation of amplicons; 4) denaturing the amplicons to create single-stranded sequences; 5) hybridizing the amplified target to oligonucleotides conjugated to a solid support (capture probes), such as beads or a microtiter plate, and to a signal sequence probe; and 6) detecting the presence or absence of each target DNA by differentiating the targets based on the capture probe features and detecting the signal sequence probe complex.

In one embodiment of the invention, the hybridization of a target and probe may occur simultaneously with the capture step by a hybrid-binding agent while in the same mixture and at an elevated temperature. The elevated temperature during the entire process may allow an increase in specificity of target capture, while decreasing the reaction time. It is to be understood that the low, moderate and high stringency hybridization/washing conditions may be varied using a variety of ingredients, buffers and temperatures well known to and practiced by the skilled artisan. For additional stringency conditions, see T. Maniatis et al., *Molecular Cloning: A Laboratory Manual*, Cold Spring Harbor Laboratory, Cold Spring Harbor, N.Y. (1982). The one step hybridization and capture may also be more efficient than performing hybridization and capture sequentially, depending on the overall assay conditions.

A method of detecting target nucleic acids of interest in the presence of other nucleic acids, by target enrichment; target amplification; and target detection, provides for a rapid, sensitive method of simultaneously detecting multiple targets in the same reaction sample. This method is useful in clinical diagnostic applications for identifying, many disease states for example, whether a patient is infected with the Human Papillomavirus (HPV) and determining which specific HPV type or types the patient has, in order to better diagnose and treat the patient. Other diseases related to specific nucleic acids are readily known in the art and would be identifiable using the detection method described in the invention.

Any source of nucleic acid, in purified or non-purified form, can be utilized as the test sample. For example, the test sample may be a food or agricultural product, or a human or veterinary clinical specimen. Typically, the test sample is a biological fluid such as urine, blood, plasma, serum, sputum or the like. Alternatively the test sample may be a tissue specimen suspected of carrying a nucleic acid of interest. The target nucleic acid in the test sample may be present initially as a discrete molecule so that the sequence to be detected constitutes the entire nucleic acid, or may only be a component of a larger molecule. It is not necessary that the nucleic acid sequence to be detected be present initially in a pure form. The test sample may contain a complex mixture of nucleic acids, of which the target nucleic acid may correspond to a gene of interest contained in total human genomic DNA or RNA or a portion of the nucleic acid sequence of a pathogenic organism which organism is a minor component of a clinical sample.

The target nucleic acid in a test sample can be DNA or RNA, such as messenger RNA, from any source, including bacteria, yeast, viruses, and the cells or tissues of higher organisms such as plants or animals. Target could also be a cDNA synthesized from the RNA by reverse transcription. Methods for the extraction and/or purification of such nucleic acids are well known in the art. Target nucleic acids may be double-stranded or single-stranded. In one embodiment of the present method, the target nucleic acids are single-stranded or made single-stranded by conventional denaturation techniques prior to the hybridization and amplification steps of the method. In one embodiment, a base denaturation technique or high temperatures are used to denature the double-stranded target DNA.

The term "oligonucleotide" as the term is used herein refers to a nucleic acid molecule comprised of two or more deoxyribonucleotides or ribonucleotides. A desired oligonucleotide may be prepared by any suitable method, such as purification from a naturally occurring nucleic acid, by molecular biological means, or by de novo synthesis. Non-limiting examples of oligonucleotides and nucleic acid probes are described herein.

Nucleic acid probes are nucleic acid sequences that hybridize to complementary RNA or DNA sequences in a test sample. Detection of the probe indicates the presence of a particular nucleic acid sequence in the test sample. The nucleic acid probes may be directly or indirectly detected. In one embodiment, the target-specific HYBRID CAPTURE method employs two types of nucleic acid sequence probes: capture sequence probe (CSP) and signal sequence probe (SSP).

A capture sequence probe or oligonucleotide comprises a nucleic acid sequence which is capable of hybridizing to unique region(s) of a target nucleic acid and being captured onto a solid phase or which enables the capture of the target nucleic acid sequence. The CSP used in the detection method can be DNA, RNA, peptide nucleic acids (PNAs) or other nucleic acid analogues. PNAs are oligonucleotides in which the sugar-phosphate backbone is replaced with a polyamide or "pseudopeptide" backbone. In a preferred embodiment, the CSP is DNA. The CSP has a minimum length of at least 8 bases, preferably between 15 and 100 bases, and more preferably between 20 and 40 bases. The CSP is substantially complementary to a target nucleic acid sequence to which the CSP hybridizes. The sequence of a CSP is preferably at least 75% complementary to the target hybridization region, more preferably, 100% complementary to this sequence. It is also preferred that the CSP contains less than or equal to 75% sequence identity, more preferably less than 50% sequence identity, to undesirable non-target sequences believed to be present in a test sample. The sequence within a target nucleic acid to which a CSP binds is preferably at least about 12 bases, more preferably 20-40 bases. The target nucleic acid sequences to which the CSP hybridizes are preferably unique sequences or group-specific sequences. Group-specific sequences are multiple related sequences that form discrete groups. For example, the CSPs may contain sequences which recognize specific human papillomavirus types, such as but not limited to, HPV-16, HPV-18, and HPV-31.

In one embodiment, the CSP used in the detection method may contain one or more modifications in the nucleic acid which allows specific capture of the probe onto a solid phase. For example, the CSP may be modified by tagging it with at least one ligand by methods well-known to those skilled in the art including, for example, nick-translation, chemical or photochemical incorporation. In addition, the CSP may be tagged at multiple positions with one or multiple types of labels. For example, the CSP may be tagged with biotin, which binds to streptavidin; or digoxigenin, which binds to anti-digoxigenin; or 2,4-dinitrophenol (DNP), which binds to anti-DNP. Fluorogens can also be used to modify the probes. Examples of fluorogens include fluorescein and derivatives, phycoerythrin, allo-phycocyanin, phycocyanin, rhodamine, Texas Red or other proprietary fluorogens. The fluorogens are generally attached by chemical modification and bind to a fluorogen-specific antibody, such as anti-fluorescein. It will be understood by those skilled in the art that the CSP can also be tagged by incorporation of a modified base containing any chemical group recognizable by specific antibodies. Other tags and methods of tagging nucleotide sequences for capture onto a solid phase coated with substrate are well known to those skilled in the art. A review of nucleic acid labels can be found in the article by Landegren, et al., "DNA Diagnostics-Molecular Techniques and Automation", Science, 242:229-237 (1988), which is incorporated herein by reference. In a further embodiment, the CSP is tagged with biotin on both the 5' and the 3' ends of the nucleotide sequence. In another embodiment, the CSP is not modified, but is captured on a solid matrix by virtue of sequences contained in the CSP capable of hybridization to the matrix.

The SSP used in the detection method may be a DNA or RNA. A signal sequence probe comprises a nucleic acid sequence which is capable of hybridizing to regions of a target nucleic acid that are adjacent to the unique regions recognized by the CSP. In one particular embodiment of the invention, the SSP and target nucleic acid form a DNA:RNA hybrid. Therefore, in this embodiment, if the target nucleic acid is a DNA, then the preferred SSP is an RNA. Similarly, if the target nucleic acid is RNA, then the preferred SSP is a DNA. The SSP is generally at least 15 bases long. However, the SSP may be up to or greater than 1000 bases long. Longer SSPs are preferred. The SSP may comprise a single nucleic acid fragment, or multiple smaller nucleic acid fragments each of which is preferably between 15 to 100 bases in length.

The sequences of CSP and SSP are selected so that they do not hybridize to the same region of a target nucleic acid or to each other. The SSP sequence and CSP sequence which correspond to regions of a target nucleic acid sequence, may be modified in order to eliminate competition between the CSP and SSP. For example, the SSP may have deletions that the CSP does not include. In addition, the CSPs and the SSPs are selected to hybridize to regions of the target within, for example, 50,000 bases of each other. The distance between the sequence to which the CSP hybridizes within the target nucleic acid and the sequence to which the SSP hybridizes is preferably between about 1 and 50,000 bases. More preferably, the distance between the CSP and SSP on a target nucleic acid is less than 3,000 bases, and most preferably, the distance is less than 1,000 bases.

In another embodiment, a portion of the SSP used in the detection method forms a DNA:RNA hybrid with a single-stranded target nucleic acid sequence, which is detected by DNA:RNA hybrid-specific binding agents, and another portion of the SSP is capable of hybridizing to the target nucleic acid. The SSP may be prepared by first cloning a single-stranded DNA sequence complementary to sequences within the target nucleic acid into a single-stranded DNA vector, then hybridizing RNA complementary to the DNA vector sequence to generate a DNA:RNA hybrid. For example, if M13 is used as the DNA vector, M13 RNA is hybridized to the M13 DNA sequence in the vector to generate a DNA:RNA hybrid. The resulting SSP forms a DNA:RNA hybrid portion as well as a single-stranded portion capable of hybridizing to sequences within the target nucleic acid. The single-stranded DNA should be at least 10 bases long, and may be up to or greater than 1000 bases long. Alternatively, the DNA:RNA hybrid portion of the SSP may be formed during or after the reaction in which the single-stranded portion of the SSP is hybridized to the target nucleic acid. The SSP can be linear, circular, or a combination of two or more forms. The DNA:RNA hybrid portion of the SSP provides amplified signals for the detection of captured hybrids using, for example, DNA:RNA hybrid specific antibodies, which are labeled or are recognized by a labeled entity, as described herein.

In yet another embodiment, the SSP used in the detection method is a molecule which does not contain sequences that are capable of hybridizing to the target nucleic acid. In this embodiment, bridge probes comprising sequences capable of hybridizing to the target nucleic acid as well as sequences capable of hybridizing to the SSP are used. The bridge probes can be DNA, RNA, peptide nucleic acids (PNAs) or other nucleic acid analogues.

In a further embodiment, a portion of the SSP and a complementary nucleic acid probe form a DNA:RNA hybrid and a single-stranded portion of the SSP contains sequences complementary to sequences within a bridge probe. The bridge probe, which is capable of hybridizing to both the target nucleic acid and the SSP, serves as an intermediate for connecting the SSP to the target nucleic acid. The DNA:RNA hybrid is detected by a DNA:RNA hybrid-specific binding agent which may be labeled or is detected by a labeled entity. The CSP hybridizes to a different portion of the target nucleic acid sequence, thereby capturing the target, bridge probe, and DNA:RNA hybrid complex to a solid phase or support. The SSP may be prepared as described above.

In another embodiment, the SSP used in one target nucleic acid detection method comprises multiple sets of repeat sequences which are complementary to a single-stranded RNA sequence capable of hybridizing to a bridge probe. A DNA oligonucleotide probe containing sequences complementary to the repeat sequences may be used to hybridize to the SSP to generate the DNA:RNA duplex needed for signal amplification.

In yet another embodiment, the bridge probe contains a poly(A) tail in addition to sequences which are capable of hybridizing to the target nucleic acid. The SSP used in this example comprises poly (dT) DNA sequences. The bridge probe is therefore capable of hybridizing to the SSP via its poly(A) tail. A RNA probe comprising poly(A) sequences may be used to hybridize to the remaining poly (dT) DNA sequences within SSP to form a DNA:RNA hybrid. The SSP comprising poly (dT) sequences and the RNA probe comprising poly (A) sequences are preferably 100 to 5,000 bases long.

The SSP used in the methods of detecting target nucleic acid sequences of the instant invention may be unmodified or modified as with the CSP using methods described above and/or known in the art. In a preferred embodiment, the SSP is a covalently unmodified probe.

It is understood that multiple CSPs and/or SSPs can be employed in the detection method of the invention.

In another embodiment, an oligonucleotide probe comprising complementary sequences of two or more distinct regions of the target nucleic acid are fused together and used as the capture sequence probe in the method of the invention. Alternatively a single probe can be designed and produced which contains sequences complementary to single or multiple target nucleic acids. This type of probe is also referred to herein as a "fused" CSP. The fused capture sequence probe works as effectively as the combination of two unfused CSPs when used at the same concentration.

The nucleic acid probes of the invention may be produced by any suitable method known in the art, including for example, by chemical synthesis, isolation from a naturally-occurring source, recombinant production and asymmetric PCR (McCabe, 1990 In: *PCR Protocols: A guide to methods and applications*. San Diego, Calif., Academic Press, 76-83). It may be preferred to chemically synthesize the probes in one or more segments and subsequently link the segments, as may be the case for preparing an oligonucleotide microarray on a microchip. Several chemical synthesis methods are described by Narang et al. (1979 *Meth. Enzymol.* 68:90), Brown et al. (1979 *Meth. Enzymol.* 68:109) and Caruthers et al. (1985 *Meth. Enzymol.* 154:287), all of which are incorporated herein by reference. Alternatively, cloning methods may provide a convenient nucleic acid fragment which can be isolated for use as a promoter primer. A double-stranded DNA probe is first rendered single-stranded using, for example, conventional denaturation methods prior to hybridization to the target nucleic acids.

Hybridization is conducted under standard hybridization conditions well-known to those skilled in the art. Reaction conditions for hybridization of a probe to a nucleic acid sequence vary from probe to probe, depending on factors such as probe length, the number of G and C nucleotides in the sequence, and the composition of the buffer utilized in the hybridization reaction. Moderately stringent hybridization conditions are generally understood by those skilled in the art as conditions approximately 25° C. below the melting temperature of a perfectly base-paired double stranded DNA. Higher specificity is generally achieved by employing incubation conditions having higher temperatures, in other words more stringent conditions. Chapter 11 of the well-known laboratory manual of Sambrook et al., MOLECULAR CLONING: A LABORATORY MANUAL, second edition, Cold Spring Harbor Laboratory Press, New York (1990) (which is incorporated by reference herein), describes hybridization conditions for oligonucleotide probes in great detail, including a description of the factors involved and the level of stringency necessary to guarantee hybridization with specificity. Hybridization is typically performed in a buffered aqueous solution, for which conditions such as temperature, salt concentration, and pH are selected to provide sufficient stringency such that the probes hybridize specifically to their respective target nucleic acid sequences but not any other sequence.

Generally, the efficiency of hybridization between probe and target improve under conditions where the amount of probe added is in molar excess to the template, preferably a 2 to $10^6$ molar excess, more preferably $10^3$ to $10^6$ molar excess. The concentration of each CSP provided for efficient capture is at least 25 fmoles/ml (25 pM) in the final hybridization solution, preferably between 25 fmoles to $10^4$ fmoles/ml (10 nM). The concentration of each SSP is at least 15 ng/ml in the final hybridization solution, preferably 150 ng/ml. Table A shows the conversion of SSP concentrations expressed in ng/ml to molar basis.

TABLE A

Conversion of SSP Concentration From ng/ml to fmoles/ml

| SSP Concentration | SSP Concentration in fmoles/ml (pM) | |
| --- | --- | --- |
| in ng/ml | SSP is a 3 kb RNA | SSP is a 5 kb RNA |
| 15 ng/ml | 15.1 | 9 |
| 150 ng/ml | 151 | 90 |
| 600 ng/ml | 606 | 364 |

Hybridization of the CSP and the SSP to the target nucleic acid in the detection step may be performed simultaneously or sequentially and in either order. In one embodiment, hybridization of the CSP and hybridization of the SSP to the target nucleic acid are performed simultaneously. In one embodiment, the DNA:RNA hybrid formed may then be captured onto a solid phase. The solid phase may be coated with a substrate to which ligand attached to the CSP binds with specificity. A portion of the target nucleic acid sequence and the SSP form a DNA:RNA hybrid, while another portion of the target nucleic acid sequence hybridizes to a CSP which is attached to a solid phase. In another embodiment, hybridization of the SSP to the target nucleic acid is performed after the hybridization of the CSP to the target nucleic acid. In this case, the CSP may be immobilized on a solid phase before or after hybridization. Both the CSP and the target nucleic acid sequence may be bound to the solid phase during the SSP hybridization reaction.

It will be understood by those skilled in the art that a solid phase, solid support, or solid matrix, may be used interchangeably and includes, for example, glass, silicon, metal, nitrocellulose, polystyrene, polyethylene, polypropylene, polycarbonate or any solid plastic material in the shape of plates, slides, dishes, beads, microbeads, particles, microparticles, cups, test tubes, slides, strands, chips, microchips, strips, membranes, microplates, microtiter plates with subwells, and microarrays. A solid phase also includes glass beads, glass test tubes and any other appropriate glass product. A functionalized solid phase such as plastic or glass that has been modified so that the surface contains carboxyl, amino, hydrazide, aldehyde groups, nucleic acid or nucleotide derivatives can also be used.

In one embodiment, the CSP is labeled with biotin, and streptavidin-coated or avidin-coated solid phase is employed to capture the hybrid. In another embodiment, streptavidin-coated microtiter plates or microplates are used. These plates may be coated passively or covalently. A further embodiment utilizes microtiter plates where each individual well has several sub-wells, where a CSP is individually attached in each sub-well. Another embodiment employs CSPs bound to beads by any of the known and commonly used methods of binding, such as using spacers and linkers. When the CSP is conjugated to a solid support, the CSP may be used for capturing and/or selecting for the target nucleic acid to which it is complementary.

The captured DNA:RNA hybrid may be detected by conventional means well-known in the art. The DNA:RNA hybrid may be detected directly or indirectly using a labeled or distinguishable DNA:RNA hybrid-specific binding agent, such as a labeled polyclonal or monoclonal antibody, or fragment thereof, specific for the DNA:RNA hybrid, an antibody specific for one or more ligands attached to the SSP, a labeled antibody, or a detectable modification on the SSP itself.

One preferred method detects the captured hybrid by using a DNA:RNA hybrid-specific antibody. In this embodiment, the DNA:RNA hybrid-specific antibody is preferably labeled with an enzyme, a fluorescent molecule or a biotin-avidin conjugate, and is preferably non-radioactive. The label can be detected directly or indirectly by conventional means known in the art such as a calorimeter, a luminometer, or a fluorescence detector. One preferred label is, for example, alkaline phosphatase. Other labels known to one skilled in the art can also be employed as a means of detecting the bound double-stranded hybrid. Detection is performed by methods conventionally used in the art, for example, colorimetry or chemiluminescence as described at Coutlee, et al., *J. Clin. Microbiol.* 27:1002-1007 (1989), incorporated by reference. Preferably, bound alkaline phosphatase conjugate is detected by chemiluminescence by adding a substrate which can be activated by alkaline phosphatase. Chemiluminescent substrates that are activated by alkaline phosphatase are well known in the art.

Detection of captured DNA:RNA hybrids is preferably achieved by binding the conjugated DNA:RNA hybrid-specific binding agent, such as but not limited to a DNA:RNA hybrid-specific antibody, to the DNA:RNA hybrid during an incubation step. In one embodiment, the DNA:RNA hybrid-specific antibody is conjugated to a solid phase, for example, a paramagnetic bead. By placing the paramagnetic beads conjugated to the DNA:RNA hybrid-specific antibodies under a magnetic force, thereby capturing the DNA:RNA hybrids, surfaces may then be washed to remove any excess antibodies and other non-hybridized materials. This step enriches or purifies the target nucleic acid sequence. These target enrichment techniques are known in the art. For example, manual washes may be performed using either an repeat pipettors or syringes, a simple pump regulated by a variostat, or by gravity flow from a reservoir with attached tubing. Commercially available tube washing systems available can also be used.

Non-limiting examples of capture sequence probes useful in the invention include those having sequences for HSV-1; sequences for HSV-2. CSPs for HPV include those having SEQ ID NOs: 1-64. The HPV types that are encompassed by these sequences include: HPV16, HPV18, HPV26, HPV31, HPV33, HPV35, HPV39, HPV45, HPV51, HPV52, HPV56, HPV58, HPV59, HPV66, HPV68, HPV73, and HPV82, several of which are high risk HPVs.

In yet another embodiment, the method employs blocker probes in addition to the CSP and SSP. A blocker probe comprises sequences that are substantially complementary to the sequences of the CSP. The sequence of a blocker probe is preferably at least about 75% complementary to the sequence of the CSP, more preferably, 100% complementary to the CSP. The addition of the blocker probes to the hybridization reaction mixture prevents non-hybridized CSP from hybridizing to cross-reactive nucleic acid sequences present in the target and therefore increases the specificity of the detection. The blocker probe is generally at least about 5 bases to about 12 bases. In one embodiment of the invention, the concentration of the blocker probe in the hybridization reaction is preferably in excess to that of the CSP and SSP. Preferably, the blocker probe is present in about a 2-fold molar excess, although, it may be present in an up to 10,000-fold molar excess. The blocker probes can be DNA, RNA, peptide, non-specific nucleic acids (PNAs) or other nucleic acid analogues.

In one embodiment, blocker probes complementary to the full-length or near full-length of the CSP are used. Following the reaction in which the hybrid between CSP, SSP and the target nucleic acid is formed, one or more blocker probes may be added to the reaction and the hybridization is continued for a desired time. The hybridization products are then detected as described above.

In another embodiment, blocker probes complementary to only a portion of the CSP and shorter than the CSP are used. These blocker probes have lower melting temperatures than the CSPs. Preferably, the melting temperature of the blocker probe is 10 degrees lower than that of the CSP. In this embodiment the blocker probe is preferably added to the target nucleic acids simultaneously with the CSP and the SSP. Since the blocker probe has a lower melting temperature than the CSP, the initial temperature for hybridization is chosen such that the blocker probe does not interfere with the hybridization of the CSP to its target sequences. However, when the temperature of the hybridization mixtures is adjusted below the temperature used for target hybridization, the blocker probe hybridizes to the CSP and effectively blocks the CSP from hybridizing to cross-reactive nucleic acid sequences. For example, when the hybridization products are incubated at room temperature on a streptavidin-coated microtiter plate during hybrid capture, the blocker probes may be added. Non-limiting examples of blocker probes are found in Table 2.

The following examples illustrate use of the present amplification method and detection assay and kit. These examples are offered by way of illustration, and are not intended to limit the scope of the invention in any manner. All references described herein are expressly incorporated in toto by reference.

EXAMPLE 1

Target-Specific Hybrid Capture (TSHC) Assay Protocol

Herpes Simplex Virus 1 (HSV-1) and Herpes Simplex Virus 2 (HSV-2) viral particles of known concentration (Advanced Biotechnologies, Inc., Columbia, Md.) or clinical samples were diluted using either Negative Control Media (Digene Corp., Gaithersburg, Md.) or Negative Cervical Specimens (Digene Corp). Various dilutions were made and aliquoted into individual microfuge tubes. A half volume of the Denaturation Reagent 5100-0431 (Digene Corp.) was added. Test samples were incubated at 65° C. for 45 minutes to allow denaturation of nucleic acids in the samples.

Following denaturation, a hybridization solution containing signal sequence probes (SSPs) (600 ng/ml each) and capture sequence probes (CSPs) (2.5 pmoles/ml each) was added to the sample, and incubated at 74° C. for 1 hour. Blocker probes in a solution containing one volume of 4× Probe Diluent (Digene Corp.), one volume of Denaturation Reagent and two volumes of the Negative Control Media were then added to the hybridization mixture and incubated at 74° C. for 15 minutes.

In a second series of experiments, following the denaturation of nucleic acids, a hybridization mixture containing SSPs (600 ng/ml each), CSPs (2.5 pmoles/ml each), and blocker probes (250 pmoles/ml each) was added to the samples and incubated at 74° C. for 1 hour.

Tubes containing reaction mixtures were cooled at room temperature for 5 minutes, and aliquots were taken from each tube and transferred to individual wells of a 96-well streptavidin capture plate (Digene Corp.). The plates were shaken at 1100 rpms at room temperature for 1 hour. The supernatants were then decanted and the plates were washed twice with SNM wash buffer (Digene Corp.) and inverted briefly to remove residual wash buffer. The alkaline-phosphatase anti-RNA/DNA antibody DR-1 Reagent (Digene Corp.) was then added to each well and incubated at room temperature for 30 minutes. The wells were then subjected to multiple wash steps which include: 1) three washes with Sharp wash buffer (Digene Corp.) at room temperature; 2) incubation of the plate with the Sharp wash buffer at 60° C. for 10 minutes on a heat block; 3) two washes with the Sharp wash buffer at room temperature; and 4) one wash with the SNM wash buffer (Digene Corp.) at room temperature. Following removal of the residual liquid, luminescent substrate 5100-0350 (Digene Corp.) was added to each well and incubated at room temperature for 15 minutes. The individual wells were then read on a plate luminometer to obtain the relative light unit (RLU) signal.

Solutions containing Negative Control Media or known HSV Negative Cervical Specimens were used as negative controls for the test samples. The signal to noise ratio (S/N) was calculated as the ratio of the average RLU obtained from a test sample to the average RLU of the negative control. The signal to noise ratio was used as the basis for determining capture efficiency and the detection of target nucleic acids. A S/N value of 2 or greater was arbitrarily assigned as a positive signal while a S/N values less than 2 was considered negative. The coefficient of variation (CV) which is a determination of the variability of the experiment within one sample set was calculated by taking the standard deviation of the replicates, dividing them by the average and multiplying that value by 100 to give a percent value.

The capture sequence probes and the blocker probes used in the experiments were synthesized using the method described by Cook et al. (1988 *Nucl. Acid. Res.*, 16: 4077-95). Unless otherwise noted, the capture sequence probes used in the experiments described herein were labeled with biotins at their 5' and 3' ends.

The signal sequence probes used in the experiments are RNA probes. These probes were prepared using the method described by Yisraeli et al. (1989, *Methods in Enzymol.*, 180: 42-50).

All of the CSPs were assayed for their type specific abilities in Type Specific HYBRID CAPTURE assays described herein. The following CSPs, i.e., SEQ ID NOs: 36-56, did not show cross-reactive properties with other types and were accepted for use in the assay.

TABLE 1

Capture Sequence Probes For HPV

| Probe | Sequence | Size (bp) | HPV Type and Sequence Location |
|---|---|---|---|
| ZL-1 | GTACAGATGGTACCGGGGTTGTAGAAG TATCTG [SEQ ID NO: 1] | 33 | HPV16 5360-5392 |
| ZL-4 | CTGCAACAAGACATACATCGACCGGTC CACC [SEQ ID NO: 2] | 31 | HPV16 495-525 |
| DP-1 | GAAGTAGGTGAGGCTGCATGTGAAGTG GTAG [SEQ ID NO: 3] | 31 | HPV16 5285-5315 |
| DP-4 | CAGCTCTGTGCATAACTGTGGTAACTT TCTGGG [SEQ ID NO: 4] | 33 | HPV16 128-160 |
| SH-1 | GAGGTCTTCTCCAACATGCTATGCAAC GTCCTG [SEQ ID NO: 5] | 33 | HPV31 505-537 |
| SH-4 | GTGTAGGTGCATGCTCTATAGGTACAT CAGGCC [SEQ ID NO: 6] | 33 | HPV31 5387-5419 |
| VS-1 | CAATGCCGAGCTTAGTTCATGCAATTT CCGAGG [SEQ ID NO: 7] | 33 | HPV31 132-164 |
| VS-4 | GAAGTAGTAGTTGCAGACGCCCCTAAA GGTTGC [SEQ ID NO: 8] | 33 | HPV31 5175-5207 |
| AH-1 | GAACGCGATGGTACAGGCACTGCAGGG TCC [SEQ ID NO: 9] | 30 | HPV18 5308-5337 |

TABLE 1-continued

Capture Sequence Probes For HPV

| Probe | Sequence | Size (bp) | HPV Type and Sequence Location |
|---|---|---|---|
| AH-2 | GAACGCGATGGTACAGGCACTGCA [SEQ ID NO: 10] | 24 | HPV18 5314-5337 |
| AL-1 | ACGCCCACCCAATGGAATGTACCC [SEQ ID NO: 11] | 24 | HPV18 4451-4474 |
| PA-4 | TCTGCGTCGTTGGAGTCGTTCCTGTCG TGCTC [SEQ ID NO: 12] | 32 | HPV18 535-566 |
| 18-1AB | *(TTATTATTA)CTACATACATTGCCG CCATGTTCGCCA [SEQ ID NO: 13] | 36 | HPV18 1369-1395 |
| 18-2AB | (TTATTATTA)TGTTGCCCTCTGTGCC CCCGTTGTCTATAGCCTCCGT [SEQ ID NO: 14] | 46 | HPV18 1406-1442 |
| 18-3AB | (TTATTATTA)GGAGCAGTGCCCAAAA GATTAAAGTTTGC [SEQ ID NO: 15] | 38 | HPV18 7524-7552 |
| 18-4AB | (TTATTATTA)CACGGTGCTGGAATAC GGTGAGGGGTG [SEQ ID NO: 16] | 37 | HPV18 3485-3512 |
| 18-5AB | (TTATTATTA)ACGCCCACCCAATGGA ATGTACCC [SEQ ID NO: 17] | 33 | HPV18 4451-4474 |
| 18-6AB | (TTATTATTA)ATAGTATTGTGGTGTG TTTCTCACAT [SEQ ID NO: 18] | 35 | HPV18 81-106 |
| 18-7AB | (TTATTATTA)GTTGGAGTCGTTCCTG TCGTG [SEQ ID NO: 19] | 30 | HPV18 538-558 |
| 18-8AB | (TTATTATTA)CGGAATTTCATTTTGG GGCTCT [SEQ ID NO: 20] | 31 | HPV18 634-655 |
| PE-1 | GCTCGAAGGTCGTCTGCTGAGCTTTCT ACTACT [SEQ ID NO: 21] | 33 | HPV18 811-843 |
| PZ-2 | GCGCCATCCTGTAATGCACTTTTCCAC AAAGC [SEQ ID NO: 22] | 32 | HPV45 77-108 |
| PZ-5 | TAGTGCTAGGTGTAGTGGACGCAGGAG GTGG [SEQ ID NO: 23] | 31 | HPV45 5295-5325 |
| CS-1 | GGTCACAACATGTATTACACTGCCCTC GGTAC [SEQ ID NO: 24] | 32 | HPV45 500-531 |
| CS-4 | CCTACGTCTGCGAAGTCTTTCTTGCCG TGCC [SEQ ID NO: 25] | 31 | HPV45 533-563 |
| PF-1 | CTGCATTGTCACTACTATCCCCACCAC TACTTTG [SEQ ID NO: 26] | 34 | HPV45 1406-1439 |
| PF-4 | CCACAAGGCACATTCATACATACACGC ACGCA [SEQ ID NO: 27] | 32 | HPV45 7243-7274 |

TABLE 1-continued

Capture Sequence Probes For HPV

| Probe | Sequence | Size (bp) | HPV Type and Sequence Location |
|---|---|---|---|
| PA-1 | GTTCTAAGGTCCTCTGCCGAGCTCTCT ACTGTA [SEQ ID NO: 28] | 33 | HPV45 811-843 |
| 45-5AB | (TTATTATTA) TGCGGTTTTGGGGGTC GACGTGGAGGC [SEQ ID NO: 29] | 36 | HPV45 3444-3470 |
| 45-6AB | (TTATTATTA) AGACCTGCCCCCTAAG GGTACATAGCC [SEQ ID NO: 30] | 36 | HPV45 4443-4469 |
| 45-8AB | (TTATTATTA) CAGCATTGCAGCCTTT TTGTTACTTGCTTGTAATAGCTCC [SEQ ID NO: 31] | 49 | HPV45 1477-1516 |
| 45-9AB | (TTATTATTA) ATCCTGTAATGCACTT TTCCACAAA [SEQ ID NO: 32] | 34 | HPV45 79-103 |
| 45-10AB | (TTATTATTA) GCCTGGTCACAACATG TATTAC [SEQ ID NO: 33] | 31 | HPV45 514-535 |
| 45-11AB | (TTATTATTA) CAGGATCTAATTCATT CTGAGGTT [SEQ ID NO: 34] | 33 | HPV45 633-656 |
| ON-1 | TGCGGTTTTGGGGGTCGACGTGGAGGC [SEQ ID NO: 35] | 27 | HPV45 3444-3470 |
| ZZ-1 | GGCGCAACCACATAACACACAGAACCA CAAAAC [SEQ ID NO: 36] | 33 | HPV18 5285-5315 |
| DXA-1 | GTTCTACACGGGTTTGCAGCACGATCA ACAACG [SEQ ID NO: 37] | 33 | HPV33 1175-1207 |
| PRA-1 | CGCTGCTTGTGGTGGTCGGTTATCGTT GTCTG [SEQ ID NO: 38] | 32 | HPV33 3389-3420 |
| TT-1 | GACGTAGTGTCGCCTCACATTTACAAC AGGAC [SEQ ID NO: 39] | 32 | HPV35 732-763 |
| TT-7 | CTCGCTTGGTGGGGTTGTAGGGGAGCT CGG [SEQ ID NO: 40] | 30 | HPV35 3432-3461 |
| NH-1 | GCTGTAGTTGTCGCAGAGTATCCCGTG AGG [SEQ ID NO: 41] | 30 | HPV39 833-862 |
| FT-7 | GTGAGCCTGTGTTATATGTAGTGCCCG AATCCC [SEQ ID NO: 42] | 33 | HPV39 5358-5390 |
| SHA-4 | CCACCTCCTGCGTCCACTACACCTAGC ACTA [SEQ ID NO: 43] | 31 | HPV45 5295-5325 |
| SHA-1 | TGCGTGCGTGTATGTATGAATGTGCCT TGTGG [SEQ ID NO: 44] | 32 | HPV45 7243-7274 |
| OCA-1 | AATTAGCGCATTGCCCCGTCCAACGTC CCG [SEQ ID NO: 45] | 30 | HPV51 482-511 |
| TAA-7 | CGCCGTGCACGTGTAGCCACCATATTT AATCAC [SEQ ID NO: 46] | 33 | HPV51 4124-4156 |
| LFA-1 | CGAATTGTGTGAGGTGCTGGAAGAATC GGTGC [SEQ ID NO: 47] | 32 | HPV52 140-171 |
| PTA-7 | GATCGTTCACAACTTTTACCTGCACCG GATCC [SEQ ID NO: 48] | 32 | HPV52 5066-5097 |
| ZOA-1 | CTAGGTTCTCTAGATGTTTGTCTCCAG CACCCC [SEQ ID NO: 49] | 33 | HPV56 521-553 |
| NAA-4 | CTGTCGGTATTGTCTGTGTCGCTGATG TGTG [SEQ ID NO: 50] | 31 | HPV56 3543-3573 |
| LA-1 | GATACACACACATTTGCAGCCCGGTCC ACACA [SEQ ID NO: 51] | 32 | HPV58 1180-1211 |
| LA-7 | GGTGGCAAAGGACGTATGTGAGTGCAG AGGAC [SEQ ID NO: 52] | 32 | HPV58 5376-5407 |
| ZV-4 | GCGTTGCGGAGGGGTATGATAGTTGCT CAGAAG [SEQ ID NO: 53] | 33 | HPV59 3385-3417 |
| ZV-10 | GTCTAGGCGTGTAGGAGGAAACAAGAT GGGG [SEQ ID NO: 54] | 31 | HPV59 7543-7573 |
| PNA-1 | CTGAACACAGCAGTTCTCTATACCAAT GGCGCTATTTC [SEQ ID NO: 55] | 38 | HPV68 81-118 |
| PNA-4 | TTGGTTGCCCCTGAGCAGTCGGACCCT ATGGATA [SEQ ID NO: 56] | 34 | HPV68 5211-5244 |
| CDA-4 | GCGCCGCATTGCTGCACCTCGTTTATA TAGCAGGGCATTTTC [SEQ ID NO: 57] | 42 | HPV82 4827-4868 |
| CDA-11 | CCTGGCGCATGTCATACACACCACATT ACTC [SEQ ID NO: 58] | 31 | HPV82 7596-7626 |
| CTA-1 | CACGAAGTGTCAGTGCACAGTATGCCT TGC [SEQ ID NO: 59] | 30 | HPV73 6006-6045 |
| CTA-16 | GCCATGTACTTCACAAACTGTTAATAC TGGTGATTGTCCC [SEQ ID NO: 60] | 40 | HPV73 720-749 |
| DLA-14 | CCTACACAGTACAAGTGGAGGCCATCA CCCG [SEQ ID NO: 61] | 31 | HPV26 3566-3596 |
| RBA-16 | GTCTGACACATACTGTTGTAACCCATA GTTAAACACAGG [SEQ ID NO: 62] | 39 | HPV26 7759-7797 |
| BNA-1 | GCTGTCTCCCTGTCTTCCTGTGTATTG TTTATAAGTGTATT [SEQ ID NO: 63] | 41 | HPV66 1051-1092 |

TABLE 1-continued

Capture Sequence Probes For HPV

| Probe | Sequence | Size (bp) | HPV Type and Sequence Location |
|---|---|---|---|
| DLA-32 | GTACAGCACTAAAATGGAGTTTGGTGT GTTACTATAGTGCATAC [SEQ ID NO: 64] | 44 | HPV66 7420-7464 |

*Sequences in parentheses are "tail" sequences not directed at HSV.

TABLE 2

Blocker Probes For HPV

| PROBE | SEQUENCE | SIZE | CSP to which binds |
|---|---|---|---|
| PA-6 | ACTCCAACGACGCAGA [SEQ ID NO: 65] | 16 | PA-4 |
| ZZ-2 | TTTTGTGGTTCTGTGTG [SEQ ID NO: 66] | 17 | ZZ-1 |
| ZZ-3 | TTATGTGGTTGCGC [SEQ ID NO: 67] | 14 | ZZ-1 |
| DXA-2 | CGTTGTTGATCGTGC [SEQ ID NO: 68] | 15 | DXA-1 |
| DXA-3 | TGCAAACCCGTGTAG [SEQ ID NO: 69] | 15 | DXA-1 |
| PRA-2 | CAGACAACGATAACCG [SEQ ID NO: 70] | 16 | PRA-1 |
| PRA-3 | ACCACCACAAGCAGC [SEQ ID NO: 71] | 15 | PRA-1 |
| TT-2 | GTCCTGTTGTAAATGTG [SEQ ID NO: 72] | 17 | TT-1 |
| TT-3 | AGGCGACACTACGTC [SEQ ID NO: 73] | 15 | TT-1 |
| TT-8 | CGAGCTCCCCTACAA [SEQ ID NO: 74] | 15 | TT-7 |
| TT-9 | CCCCACCAAGCGA [SEQ ID NO: 75] | 13 | TT-7 |
| NH-2 | CCTCACGGGATACTC [SEQ ID NO: 76] | 15 | NH-1 |
| NH-3 | TGCGACAACTACAGC [SEQ ID NO: 77] | 15 | NH-1 |
| FT-8 | GGATTCGGGCACTA [SEQ ID NO: 78] | 14 | FT-7 |
| FT-9 | CATATAACACAGGCTCAC [SEQ ID NO: 79] | 18 | FT-7 |
| SHA-5 | TAGTGCTAGGTGTAGTGG [SEQ ID NO: 80] | 18 | SHA-4 |
| SHA-6 | ACGCAGGAGGTGG [SEQ ID NO: 81] | 13 | SHA-4 |
| SHA-2 | TACATACACGCACGCA [SEQ ID NO: 82] | 16 | SHA-1 |
| SHA-3 | CCACAAGGCACATTCA [SEQ ID NO: 83] | 16 | SHA-1 |
| TAA-8 | GCTACACGTGCACGGCG [SEQ ID NO: 84] | 17 | TAA-7 |
| TAA-9 | GTGATTAAATATGGTGG [SEQ ID NO: 85] | 17 | TAA-7 |
| OCA-2 | GGGACGTTGGACG [SEQ ID NO: 86] | 13 | OCA-1 |
| OCA-3 | GGCAATGCGCTAAT [SEQ ID NO: 87] | 14 | OCA-1 |
| LFA-2 | CACCGATTCTTCCAG [SEQ ID NO: 88] | 15 | LFA-1 |
| LFA-3 | CACCTCACACAATTCG [SEQ ID NO: 89] | 16 | LFA-1 |
| PTA-8 | GGATCCGGTGCAG [SEQ ID NO: 90] | 13 | PTA-7 |
| PTA-9 | GTAAAAGTTGTGAACGATC [SEQ ID NO: 91] | 19 | PTA-7 |
| ZOA-2 | GGTGCTGGAGACAA [SEQ ID NO: 92] | 14 | ZOA-1 |
| ZOA-3 | ACATCTAGAGAACCTAG [SEQ ID NO: 93] | 17 | ZOA-1 |
| NAA-5 | CACACATCAGCGACA [SEQ ID NO: 94] | 15 | NAA-4 |
| NAA-6 | CAGACAATACCGACAG [SEQ ID NO: 95] | 16 | NAA-4 |
| LA-2 | TGTGTGGACCGGG [SEQ ID NO: 96] | 13 | LA-1 |
| LA-3 | CTGCAAATGTGTGTGTAT [SEQ ID NO: 97] | 18 | LA-1 |
| LA-8 | GTCCTCTGCACTCACAT [SEQ ID NO: 98] | 17 | LA-7 |
| LA-9 | ACGTCCTTTGCCAC [SEQ ID NO: 99] | 14 | LA-7 |
| ZV-5 | TTCTGAGCAACTATCATAC [SEQ ID NO: 100] | 19 | ZV-4 |
| ZV-6 | CCCTCCGCAACG [SEQ ID NO: 101] | 12 | ZV-4 |
| ZV-11 | CCCCATCTTGTTTCC [SEQ ID NO: 102] | 15 | ZV-10 |
| ZV-12 | TCCTACACGCCTAGAC [SEQ ID NO: 103] | 16 | ZV-10 |
| PNA-2 | TATAGAGAACTGCTGTGTTC [SEQ ID NO: 104] | 20 | PNA-1 |
| PNA-3 | GAAATAGCGCCATTG [SEQ ID NO: 105] | 15 | PNA-1 |
| PNA-5 | CTCAGGGCAACCA [SEQ ID NO: 106] | 14 | PNA-4 |
| PNA-6 | ATCCATAGGGTCCGAC [SEQ ID NO: 107] | 16 | PNA-4 |

TABLE 2-continued

Blocker Probes For HPV

| PROBE | SEQUENCE | SIZE | CSP to which binds |
|---|---|---|---|
| CDA-5 | CAATGCGGCGC [SEQ ID NO: 108] | 11 | CDA-4 |
| CDA-6 | TATAAACGAGGTGCAG [SEQ ID NO: 109] | 16 | CDA-4 |
| CDA-7 | GAAAATGCCCTGCTA [SEQ ID NO: 110] | 15 | CDA-4 |
| CDA-12 | ACATGCGCCAGG [SEQ ID NO: 111] | 12 | CDA-11 |
| CDA-13 | GAGTAATGTGGTGTGTATG [SEQ ID NO: 112] | 19 | CDA-11 |
| CTA-2 | GCAAGGCATACTGTG [SEQ ID NO: 113] | 15 | CTA-1 |
| CTA-3 | CACTGACACTTCGTG [SEQ ID NO: 114] | 15 | CTA-1 |
| CTA-17 | GGACAATCACCAGTATTA [SEQ ID NO: 115] | 18 | CTA-16 |
| CTA-18 | AGTTTGTGAAGTACATGG [SEQ ID NO: 116] | 18 | CTA-16 |
| DLA-15 | CGGGTGATGGCC [SEQ ID NO: 117] | 12 | DLA-14 |
| DLA-16 | CCACTTGTACTGTGTAGG [SEQ ID NO: 118] | 18 | DLA-14 |
| RBA-17 | CTGTGTTTAACTATGGGT [SEQ ID NO: 119] | 18 | RBA-16 |
| RBA-18 | TACAACAGTATGTGTCAGAC [SEQ ID NO: 120] | 20 | RBA-16 |
| BNA-2 | AAGACAGGGAGACAGC [SEQ ID NO: 121] | 16 | BNA-1 |
| BNA-3 | CTTATAAACAATACACAGG [SEQ ID NO: 122] | 19 | BNA-1 |
| DLA-33 | ATGCACTATAGTAACACACC [SEQ ID NO: 123] | 20 | DLA-32 |
| DLA-34 | ACTCCATTTTAGTGCTGTA [SEQ ID NO: 124] | 19 | DLA-32 |

EXAMPLE 2

Effect of the Distance Between the CSP and the SSP Target Sites on Capture Efficiency The effect of the distance between capture sequence probe (CSP) and signal sequence probe (SSP) hybridization sites on a HSV-1 target nucleic acid on capture efficiency was evaluated. CSPs that hybridize to HSV-1 nucleic acid sequences which are located 0.2 kb, 3 kb, 18 kb, 36 kb and 46 kb from the site of SSP hybridization were tested. The general TSHC method described in Example 1 was employed. The capture efficiencies were 100%, 50%, 30%, 19% and 7%, respectively (Table 3). A steady decline in relative capture efficiencies was observed as the distance increased from 0.2 Kb to 46 Kb.

TABLE 3

Effect of Distance between Target Sites on Capture Efficiency

| CSP | SSP | Distance Between Target Site | Relative Capture Efficiency |
|---|---|---|---|
| BRH19 | H19 | 0.2 Kb | 100% |
| F15R | H19 | 3 Kb | 50% |
| F6R | RH5B | 18 Kb | 30% |
| F15R | RH5B | 36 Kb | 19% |
| F6R | H19 | 46 Kb | 7% |

EXAMPLE 3

Capture Efficiency of Various CSPs and SSPs In TSHC Detection of HSV-1

The capture efficiency of capture sequence probes (CSPs) for each of the four HSV-1 specific signal sequence probes (SSPs), H19, RH5B, RH3 and R10, in the detection of HSV-1 by TSHC were evaluated. The criteria used for designing the capture sequence probes were: 1) the CSP hybridization site is within 1 kb either 5' or 3' of the SSP hybridization site on the HSV-1 nucleic acid sequence, preferably within 0.5 kb; and 2) the CSPs contain sequences that are unique to HSV-1, with no stretches of sequence homology to HSV-2 greater than 10 bases. The CSPs were designed to target the 5' and 3' regions adjacent to the SSP hybridization site, preferably with a 5' CSP and a 3' CSP for each SSP. The commercially available OMIGA software (Oxford Molecular Group; Campbell, Calif.) was instrumental in the identification of such sites. The melting temperature (Tm) of the CSPs was designed to be between 70° C. to 85° C. The general TSHC method described in Example 1 was employed. Eleven CSPs (which bind to 6 different sites) for H19, six CSPs (which bind to three unique sites) for RH5B, six CSPs (which bind to six unique sites) for RH3, and two CSPs for R10 were tested. As shown in Table 4, efficient capture sequence probes were found for signal sequence probes H19, RH5B and R10.

TABLE 4

CSPs and SSPs for TSHC Detection of HSV-1

| SSP | CSP | Cap % | SSP | CSP | Cap % | SSP | CSP | Cap % |
|---|---|---|---|---|---|---|---|---|
| R10 | ON-3 | 100% | RH5B | TS-1 | 50% | H19 | HZ-1 | 50% |
| R10 | ON-3 | 80% | RH5B | NC-1 | 75% | H19 | HZ-2 | 20% |
| | | | RH5B | VH-4 | 130% | H19 | ZD-1 | 40% |
| | | | RH5B | TS-2 | 25% | H19 | ZD-2 | 20% |
| | | | RH5B | VH-3 | 50% | H19 | BRH19 | 70% |
| | | | | | | H19 | VH-2 | 70% |
| | | | | | | H19 | F15R | 25% |

EXAMPLE 4

Clinical Specimen Testing

A 64-member clinical specimen panel was tested for HSV-1 and HSV-2 using both TSHC and Hybrid Capture 2 (hc2™; Digene Corp.) methods. The panel included 15 samples containing known quantities of HSV-1 or HSV-2, and 49 samples known to be negative for HSV-1 and HSV-2 by PCR testing. Accordingly, the 15 positive samples were "expected" to test positive in both the HC2 and TSHC assays, and the 49 negative samples were "Expected" to test negative in both the HC2 and TSHC tests.

The general TSHC method described in Example 1 was employed. The results using the HC2 method and the TSHC method are shown in Tables 5 and 6, respectively. Of the 49 samples "Expected" to yield negative result, 5 samples tested positive and 44 samples tested positive using the HC2 method. In comparison, all 49 samples tested negative using the TSHC method. Therefore, the TSHC method is superior in specificity to the HC2 method in the detection of HSV-1 and HSV-2.

TABLE 5

Observed vs. Expected Results for HC2 Detection of HSV1 and HSV2

| HC2 Result | Expected Result | |
|---|---|---|
| | Positive | Negative |
| Positive | 15 | 5 |
| Negative | 0 | 44 |
| Total | 15 | 49 |

TABLE 6

Observed vs. Expected Results for TSHC Detection of HSV1 and HSV2

| TSHC Result | Expected Result | |
|---|---|---|
| | Positive | Negative |
| Positive | 14 | 0 |
| Negative | 1 | 49 |
| Total | 15 | 49 |

EXAMPLE 5

Effect of Combining Probes in TSHC Detection of HSV

The effect of combining HSV-1 specific signal sequence probe and capture sequence probe sets on HSV-1 detection was assessed. TSHC detection of HSV-1 and HSV-2 cross-reactivity was performed separately with two different sets of RNA signal sequence probe/biotinylated capture sequence probe combinations (Set #1: H19 plus HZ-1; and Set #2: RH5b plus the TS-1 and TS-2). TSHC was also performed with both RNA signal sequence probe/biotinylated capture sequence probe sets combined to assess the effect of combining the two probe sets on sensitivity and cross-reactivity. The general TSHC method described in Example 1 was employed. The results shown in Table 7 clearly demonstrate an additive effect of combining the two probe sets for HSV-1 detection with no apparent increase in HSV-2 cross-reactivity.

TABLE 7

Sensitivity is Improved by Combining HSV-1 Specific CSPs and SSPs

| Capture Sequence Probes | Signal Sequence Probes | VP/ml | RLU | CV | S/N |
|---|---|---|---|---|---|
| HZ-1 | H19 | 0 | 60 | 3% | 1.0 |
| HZ-1 | H19 | $10^5$ HSV-1 | 267 | 4% | 4.5 |
| HZ-1 | H19 | $10^6$ HSV-1 | 2316 | 6% | 38.9 |

TABLE 7-continued

Sensitivity is Improved by Combining HSV-1 Specific CSPs and SSPs

| Capture Sequence Probes | Signal Sequence Probes | VP/ml | RLU | CV | S/N |
|---|---|---|---|---|---|
| HZ-1 | H19 | $10^7$ HSV2 | 49 | 2% | 0.8 |
| TS-1, TS-2 | RH5B | 0 | 78 | 6% | 1.0 |
| TS-1, TS-2 | RH5B | $10^5$ HSV-1 | 291 | 6% | 3.8 |
| TS-1, TS-2 | RH5B | $10^6$ HSV-1 | 2368 | 11% | 30.6 |
| TS-1, TS-2 | RH5B | $10^7$ HSV2 | 75 | 11% | 1.0 |
| HZ-1, TS-1, TS-2 | H19, RH5B | 0 | 70 | 12% | 1.0 |
| HZ-1, TS-1, TS-2 | H19, RH5B | $10^5$ HSV-1 | 457 | 10% | 6.5 |
| HZ-1, TS-1, TS-2 | H19, RH5B | $10^6$ HSV-1 | 4263 | 1% | 60.9 |
| HZ-1, TS-1, TS-2 | H19, RH5B | $10^7$ HSV2 | 67 | 6% | 1.0 |

EXAMPLE 6

Detection of HPV Types in Multiplex Format

Rapid, sensitive and specific detection of 13 sequences representing different types of Human Papillomavirus (HPV) in a single biological sample was performed in a multiplex format. This assay can analyze up to 96 samples in a 96 well microplate format within a 5 hour period of time. At least 500 copies of one type of virus may be detected within 5 hours after beginning the assay.

Protein G-paramagnetic beads (Dynal Corp.; Brown Deer, Wis.) and Luminex® 100™ carboxylated beads (Luminex Corp., Austin, Tex.) were used as solid supports. HPV RNA was prepared by in vitro transcription of HPV plasmids as commonly understood in the art and described by Ausubel, et al. [*Current Protocols in Molecular Biology, New York, Wiley Publishing*, 1993, incorporated by reference]. The novel assay has three steps including 1) target enrichment; 2) target amplification; and 3) target detection.

Target Enrichment:

A sample was prepared for amplification by separating unwanted or non-specific DNA and contaminants from pre-selected specific targets. This step removes unwanted DNA, the presence of which substantially decreases the sensitivity of target amplification. Target enrichment was performed by capturing sequence specific RNA:DNA hybrids onto paramagnetic beads. The beads were initially modified with antibodies specific for RNA:DNA hybrids or HYBRID CAPTURE antibodies (Digene, Corp.). More specifically, the HC-Ab paramagnetic beads were prepared by mixing 1 mL of Protein G Magnetic Beads (2.7×10$^9$ beads/mL; Dynal, Corp.) with 375 µg of HC-Ab and incubating at room temperature in PBS for 40 minutes forming bead-antibody (bead-Ab) complexes. The bead-Ab complexes were accumulated at the bottom of the well by placing the plate upon a magnetic grid (Dynal, Corp.) and washed once with 0.2 M Triethanolamine, pH 8.2. Antibodies were cross-linked to the Protein G in a reagent of 20 mM DMP/0.2M Triethanolamine, pH 8.2 for 30 minutes. The bead-Ab complexes were washed 3× with 1 mL PBS-0.05% Tween20. Beads were then resuspended in 1 mL of PBS-Tween and stored at 4° C.

The sample was serial diluted with various HPV plasmids (10 kb) prepared in a solution composed of 100 µg/ml Herring Sperm DNA, 1 M Guanidine-HCl, 10 mM Tris-HCl (pH 8.0), 10 mM EDTA, 0.05% Sodium Azide in deionized water. Each of the diluted samples (50 µl) was mixed in a 96-well microplate containing 25 µl of 1.75M NaOH per well and incubated at 50° C. for 15 minutes to denature the sample. A cocktail of 13 types of HPV RNA selected from Table 1 (15 ng each per assay) was added to the denatured samples in neutralizing solution: 25 µL of 0.125 M sodium citrate, 0.125 M sodium phosphate, 0.6 M triethanolamine, 0.6 BES, 0.83 M glacial acetic acid, 3% polyacrylic acid, 5 mM EDTA, 0.05% sodium azide, and 0.4% Tween-20 (pH 3.6-4.1). The HYBRID CAPTURE antibody (HC-Ab)-conjugated paramagnetic beads ($5.4 \times 10^6$ beads per assay) were then immediately added to the neutralized sample. The HPV RNA and paramagnetic bead-antibody conjugates were hybridized to the sample target sequences for 30 min at 65° C. with shaking at 1100 rpm. The magnetic bead-target complexes were accumulated at the bottom of the well by placing the plate upon a magnetic grid (Dynal, Corp.). The supernatant was aspirated by pipette and the beads were washed three times using a wash buffer (40 mM Tris pH 8.2, 100 mM sodium chloride, 0.05% sodium azide and 0.05% Tween-20), thereby removing any contaminants.

Target Amplification:

Isothermal amplification of the sample target DNA was performed using random primers and a DNA polymerase having strand displacement activity. The DNA targets were amplified using phi29 DNA polymerase primed with random pentamers. The pentamer primers were synthesized with two phosphorothioate bonds at the 3'-end to prevent degradation by the nuclease. Other modifications may include, but are not limited to, 2'O-methyl groups which are incorporated into the structure of the primers. The target DNA was amplified for 2 hours. Paramagnetic beads with captured target nucleic acid obtained in the target enrichment step were resuspended in 20 µl reaction composed of 50 mM Tris-HCl, pH 7.5, 10 mM $MgCl_2$, 10 mM $(NH_4)_2SO_4$, 4 mM DTT, 200 µg/ml acetylated BSA, 400 µM each dNTP, 125 µM random pentamers and 1 U of phi29 DNA polymerase (New England Biolabs, Inc) and incubated for 2 hours at 30° C.

Primers which may be useful in the amplification step are listed below.

```
Probe
                                      (SEQ ID NO: 125)
HPV16 5'-\FAM\TCAGGACCCACAGGAGCGACCCAG-3'\BHQ Forward primer
                                      (SEQ ID NO: 126)
5'-GCACCAAAAGAGAACTGCAATGT-3'

Reverse primer
                                      (SEQ ID NO: 127)
5'-CATATACCTCACGTCGCAGTAACT-3'
* duel-labeled probe and primers (Integrated DNA
Technologies, Inc.; Salt Lake City, UT)
* FAM-fluorescent reporter; BHQ-black hole quencher
```

Target Detection:

Amplified sequences were detected using a liquid-based bead array system that integrates optics, fluidics, and signal processing enabling multiplex capabilities (Luminex technology). The Luminex technology uses a highly sensitive assay system based on fluorescent microbeads and reporter molecules that can detect multiple targets in the same assay well (see, U.S. Pat. Nos. 5,981,180; 6,524,793; 5,736,330; 6,449,562; 6,592,822; 6,632,526; 6,514,295; 6,599,331; 6,046,807?; and 6,366,354). The Luminex detection instrument uses two lasers: one for the detection of the fluorescent bead itself and the other for the fluorescent reporter. The bi-colored fluorescent beads enabled multiplex detection of up to about 100 different targets. Luminex technology was applied to HPV typing in this example. This method increased the sensitivity and robustness of the platform.

Two oligonucleotide sequences complementary to the late (L)- and early (E)-regions [M H Einstein and G N Goldberg, Cancer Invest. 20: 1080-1085, 2002, incorporated by reference] on the specific HPV type were conjugated to the commercially available differently colored Luminex carboxylated beads using the manufacturer's protocol. Sequences of capture oligonucleotides were presented in Table 1. Two oligonucleotides of one specific HPV type were attached to the same bead set, thereby eliminating false negative results caused by the deletion of the HPV L-region which may occur in cancer cells. An amplicon purification step was not required before the detection step since hybridization had been performed in the same tube which held the paramagnetic beads introduced during the first target enrichment step.

The detection step of the assay began with amplicon denaturation in 75 µl of 438 mM NaOH at 70° C. for 15 minutes. A cocktail of 13 different types of HPV RNA (15 ng each per assay) was added to the denatured sample in 25 ul of 0.125 M sodium citrate, 0.125 M sodium phosphate, 0.6 M triethanolamine, 0.6 BES, 0.83 M glacial acetic acid, 3% polyacrylic acid, 5 mM EDTA, 0.05% sodium azide and 0.4% Tween-20 (pH 3.6-4.1). Then, the 13 types of oligonucleotides are each conjugated to carboxylated Luminex polystyrene beads ($5 \times 10^3$ beads per assay) and immediately added to the neutralized sample. The RNA and bead-oligonucleotide conjugates were hybridized to the target for 30 minutes at 65° C. while shaking at 1100 rpm. The samples were then filtered through the 96-well filter plate (Whatman) and the beads were resuspended in 100 µl of 1× phosphate-buffered saline (PBS), 0.05% Tween-20, 10% goat serum and 10 ng of mouse monoclonal DNA:RNA hybrid-specific antibodies labeled with phycoerythrin (PE-HC-Ab). The samples were incubated for 30 minutes at room temperature (18-25° C.) while shaking at 1100 rpm. The excess antibody was removed by vacuum filtration and the beads with target complexes were resuspended in 100 µL PBS with 0.05% Tween-20. Samples were then analyzed by Luminex flowcytometer after adjusting the gain of the photomultiplier tube to 700 volts.

The improved sensitivity of this step resulted from long RNA signal sequence probes (6500 bp, approximate length) that permit binding of multiple phycoerythrin antibodies (PE-Ab), which thereby resulted in about 500 fold amplification of signal compared to other detection techniques, such as those that use fluorophores conjugated to short hybridization probes. The RNA signal sequence probes may have a length ranging from about 500 bases to about 10 kilobases, or up to just less than 100% of the target nucleic acid length.

The results shown in Table 8 demonstrate the sensitivity of the detection of HPV 16 in the presence of all 13 HPV Type bead sets. The sensitivity of detection for plasmids was greater than 500 copies per assay as indicated by the robust signal to noise ratio. The initial sample volume was 50 µl, but may be increased to 500 µl or even the entire sample (for use in tube-based assays; not shown), which will increase the assay sensitivity to an even greater degree. The results also demonstrated the specificity for HPV 16 detection. Essentially no signal was detected on bead sets specific for HPV targets other then HPV 16. The signals of Table 8 (average, n=4 replicates, % CV between 3 and 31%) are the median fluorescent intensities (MFI) for 100 beads (events) per sample counted by the flowcytometer. The background or noise value is the MFI of samples containing no target.

Table 9 demonstrates the sensitivity and specificity of detection of all 13 HPV types. The target HPV types are listed along the x-axis and the nucleic acid probes are listed along the y-axis. The same HPV target and HPV probe for each type is highlighted diagonally across the table (positive result).

These boxes demonstrate the high level of specificity of the probe for its HPV target. This experiment confirms that the probes are specific for corresponding HPV type targets. The results in Table 9 show that, for example, HPV 16 target binds only the corresponding HPV 16 probe (positive result) and does not bind the probes for other HPV types (negative result).

TABLE 8

Sensitivity Of The Detection Of HPV 16

| Target input (copies/assay) | Average Signal/Noise Ratio for each bead set specific for the individual HPV type | | | | | | | | | | | |
|---|---|---|---|---|---|---|---|---|---|---|---|---|
| | 16 | 18 | 31 | 33 | 35 | 39 | 45 | 51 | 52 | 56 | 58 | 59 | 68 |
| $5 \times 10^2$ | 194 | 1 | 1 | 1 | 1 | 2 | 1 | 1 | 1 | 1 | 1 | 1 | 1 |
| $5 \times 10^3$ | 419 | 1 | 1 | 1 | 1 | 2 | 1 | 1 | 1 | 1 | 1 | 2 | 1 |
| $5 \times 10^4$ | 553 | 2 | 1 | 1 | 1 | 3 | 1 | 2 | 1 | 1 | 1 | 2 | 1 |

HPV 16 has a low signal to noise ratio, where the signals (average, n=4 replicates, % CV (coefficient of variation) between 3% and 31%) are the median fluorescent intensities (MFI) for 100 beads (events) per sample counted by the flow-cytometer. The noise value is the MFI of samples containing no target plasmids.

EXAMPLE 8

Detection of HPV in Clinical Samples

HPV was detected in cervical samples, where the cervical samples were collected in specimen transport media (STM; Digene Corp., Gaithersburg, Md.) and initially screened for the high-risk HPV types using the commercially available HC2 High-Risk HPV DNA TeSt™ assay (Digene Corp.). The HC2 assay results were compared with those of the HPV typing assay described in this invention.

Cervical samples were collected using a brush and kept in a storage medium (1 M Guanidine-HCl, 10 mM Tris-HCl (pH

TABLE 9

Specificity Of HPV Types

| Target | Rxn copies (ds-plasmid) | Average LMX-MFI (n = 2) for each specific HPV capture probe/bead NB 0713, pg. 68-69 (013004) | | | | | | | | | | | |
|---|---|---|---|---|---|---|---|---|---|---|---|---|---|
| | | 16 | 18 | 31 | 33 | 35 | 39 | 45 | 51 | 52 | 56 | 58 | 59 | 68 |
| 16 | 0.E+00 | 69 | 31 | 22 | 33 | 25 | 91 | 50 | 36 | 22 | 46 | 33 | 66 | 34 |
| | 1.E+02 | 3946 | 29 | 29 | 39 | 25 | 94 | 53 | 48 | 34 | 46 | 40 | 77 | 38 |
| 18 | 0.E+00 | 50 | 18 | 25 | 17 | 25 | 50 | 26 | 31 | 15 | 33 | 18 | 43 | 28 |
| | 1.E+02 | 80 | 3093 | 18 | 26 | 21 | 90 | 47 | 33 | 26 | 39 | 25 | 69 | 27 |
| 31 | 0.E+00 | 62 | 29 | 22 | 35 | 30 | 65 | 43 | 42 | 28 | 42 | 32 | 70 | 35 |
| | 1.E+02 | 76 | 25 | 4121 | 42 | 28 | 79 | 62 | 42 | 27 | 40 | 34 | 87 | 42 |
| 33 | 0.E+00 | 67 | 32 | 26 | 28 | 23 | 71 | 43 | 34 | 24 | 37 | 31 | 65 | 36 |
| | 1.E+02 | 91 | 29 | 23 | 8389 | 26 | 105 | 54 | 40 | 32 | 56 | 31 | 109 | 38 |
| 35 | 0.E+00 | 37 | 20 | 16 | 23 | 15 | 36 | 24 | 25 | 21 | 22 | 20 | 35 | 23 |
| | 1.E+02 | 62 | 31 | 16 | 29 | 3658 | 51 | 33 | 23 | 21 | 39 | 25 | 57 | 27 |
| 39 | 0.E+00 | 63 | 32 | 26 | 24 | 23 | 66 | 44 | 39 | 27 | 47 | 26 | 60 | 38 |
| | 1.E+02 | 104 | 34 | 35 | 39 | 25 | 3881 | 63 | 52 | 39 | 56 | 40 | 108 | 35 |
| 45 | 0.E+00 | 41 | 30 | 21 | 22 | 24 | 48 | 26 | 28 | 16 | 29 | 26 | 43 | 21 |
| | 1.E+02 | 46 | 24 | 23 | 18 | 27 | 53 | 4859 | 34 | 24 | 35 | 26 | 53 | 18 |
| 51 | 0.E+00 | 31 | 17 | 17 | 27 | 26 | 33 | 25 | 24 | 22 | 26 | 20 | 35 | 23 |
| | 1.E+02 | 45 | 23 | 24 | 21 | 17 | 46 | 28 | 4500 | 12 | 26 | 23 | 46 | 18 |
| 52 | 0.E+00 | 21 | 25 | 19 | 21 | 16 | 32 | 16 | 19 | 14 | 19 | 19 | 41 | 16 |
| | 1.E+02 | 44 | 38 | 14 | 25 | 23 | 42 | 36 | 24 | 3500 | 31 | 24 | 51 | 25 |
| 56 | 0.E+00 | 44 | 23 | 18 | 25 | 19 | 40 | 27 | 29 | 23 | 24 | 23 | 42 | 29 |
| | 1.E+02 | 52 | 28 | 19 | 39 | 30 | 50 | 37 | 27 | 15 | 5154 | 26 | 50 | 18 |
| 58 | 0.E+00 | 30 | 19 | 16 | 17 | 26 | 34 | 18 | 27 | 17 | 19 | 19 | 36 | 15 |
| | 1.E+02 | 47 | 26 | 11 | 22 | 11 | 30 | 26 | 22 | 14 | 30 | 8631 | 54 | 22 |
| 59 | 0.E+00 | 18 | 22 | 16 | 16 | 19 | 26 | 18 | 17 | 18 | 21 | 14 | 26 | 19 |
| | 1.E+02 | 45 | 24 | 17 | 16 | 22 | 42 | 26 | 28 | 18 | 24 | 19 | 3045 | 20 |
| 68 | 0.E+00 | 22 | 26 | 23 | 13 | 19 | 26 | 12 | 20 | 14 | 20 | 17 | 20 | 15 |
| | 1.E+02 | 37 | 23 | 18 | 19 | 18 | 34 | 30 | 21 | 19 | 22 | 20 | 28 | 5063 |

EXAMPLE 7

Detection of HPV16, HPV58 and HPV33

Cervical samples infected with multiple types of HPV were modeled by mixing three plasmids each inserted with a different type of HPV sequence (10 kb) in the sample buffer indicated in Example 6. This example demonstrates the capability of the assay to detect multiple infections, when more than one HPV type is present in the sample.

The assay of multiple target samples was performed as illustrated in Example 21. Samples consisted of $1 \times 10^2$ copies of HPV 16, $1 \times 10^4$ copies of HPV 58 and $1 \times 10^6$ copies of HPV 33. Results in Example 7 demonstrated that HPV 16 target in low abundance was detected even in the highly abundant presence of other HPV types. Example 7 demonstrates that 8.0), 10 mM EDTA, and 0.05% Sodium Azide in deionized water) until use. Aliquots (50 µl) of cervical samples were analyzed by HC2 (Digene Corp) according to the manufacturer's recommendations or by the method described in Example 6. In order to compare the sensitivity of the two assays, the positive sample was serially diluted in a cervical sample without HPV infection.

TABLE 10

Comparison Of Detection Sensitivity Of Clinical Samples

| Positive sample dilutions | HC2, Signal/CutOff | Typing Assay, S/N |
|---|---|---|
| No dilution | 187.2 | 585.1 |
| 1:10 | 21.2 | 310.4 |

TABLE 10-continued

Comparison Of Detection Sensitivity Of Clinical Samples

| Positive sample dilutions | HC2, Signal/CutOff | Typing Assay, S/N |
|---|---|---|
| 1:100 | 2.3 | 199.2 |
| 1:1000 | <1 | 113.4 |
| 1:10,000 | <1 | 43.1 |

The sensitivity of HC2 on clinical samples is reported in Table 10 and shows a Signal/Cutoff of 2.3 (100 fold diluted sample) which corresponds approximately to 10,000 HPV targets per assay. Accordingly, when compared to the sensitivity of the HPV typing assay of the invention, the invention is at least 100 fold greater and equal to 100 copies per assay with a signal to noise ratio (S/N) of about 43.

EXAMPLE 9

Detection of Circular, Linear and Integrated Forms of HPV DNA

The assay of the invention may detect DNA sequences that are linear, as well as, circular. Thus, the amplification that occurs in the inventive assay does not necessarily occur by the "rolling circle" phenomenon. Therefore, the targets of the inventive assay need not be circular. They may be linear, either because the circular pathogenic DNA is nicked by denaturation, or because the pathogenic (viral) DNA targets is integrated into the linear host (human) genome, or because the pathogenic DNA is a linear genome.

Samples including serial dilutions of HPV 16 plasmid that were either linear or circular or serial dilutions of purified DNA from CaSki cells were diluted in TE buffer. Linear plasmids were created by restriction endonuclease digestion of the circular plasmids using standard techniques. CaSki cell DNA is human genomic DNA that contains 500 copies of integrated HPV 16 viral genomes per human genome. The concentration of HPV 16 copies per assay for the CaSki cell DNA was calculated from the sizes and ratios of the two genomes, human and HPV, and the optical density measurements of the purified CaSki DNA.

Targets were heat denatured at 95° C. for 3 minutes in the presence of random primers immediately before amplification in 50 mM Tris-HCl (pH 8.0), 0.5 mM EDTA and 50 μM random hexamer primer (phosphorothioated at ultimate 3' bonds). Single-stranded targets were then amplified for 120 minutes at 30° C. in 20 μl reactions composed of 50 mM Tris-HCl (pH 7.5), 10 mM MgCl$_2$, 10 mM (NH$_4$)$_2$SO$_4$, 4 mM DTT, 0.2 mg/ml acetylated BSA, 400 μM each dNTPs, 0.13 mM random hexamers and 10 U of phi29 DNA polymerase (Epicentre, Inc).

The amplified targets were detected as described in Example 6 with the following exception. The RNA:DNA hybrid complexes were tagged first with a mouse monoclonal anti-RNA:DNA primary antibody (10 μg/assay) and then with a goat-anti-mouse IgG secondary antibody conjugated with phycoerythrin (1.6 μg/assay).

The results in Table 11 demonstrate that the assay of the invention detected circular, linear and integrated DNA with robust Signal/Noise ratios, thereby demonstrating that the effectiveness of the assay was not dependent on the "rolling-circle" mechanism. However, the "rolling circle" mechanism could have accelerated the reaction, because the circular target was amplified more efficiently than the linear target.

TABLE 11

Detection Of Circular Linear And Integrated Targets With The Proposed Method

| | Signal/Noise | | |
|---|---|---|---|
| Target (copies/assay) | Linear DNA | Circular DNA | Integrated DNA |
| $1 \times 10^2$ | 71 | 123 | 21 |
| $1 \times 10^4$ | 96 | 130 | 83 |
| $1 \times 10^6$ | 89 | 142 | 77 |

The signals were averages (n = 2) of the median fluorescent intensities (MFI) for 100 beads (events) per sample counted by the flowcytometer. The noise value is the average MFI of samples containing no target plasmids.

EXAMPLE 10

Isothermal Amplification Catalyzed by PHI29 DNA Polymerase Using Random Oligonucleotides Another embodiment of the target amplification step utilizes modified oligonucleotides optimized in the length of the random primers. The random pentamers, 5'-NpNpNpsNpsN-3' were made by IDT, Inc. For the data generated in this Example, HPV 16 plasmid was amplified in a 20 μL total reaction volume with isothermal amplification for 2 hours at 30° C. The DNA target was heat denatured for 3 minutes at 95° C. in 10 μl of 50 mM Tris-HCl, pH 8.0, 0.5 mM EDTA, 50 μM of primers. Isothermal amplification was performed in 20 μl of 50 mM Tris-HCl, pH 7.5, 10 mM MgCl$_2$, 10 mM (NH$_4$)$_2$SO$_4$, 4 mM DTT, 200 μg/ml acetylated BSA, 400 M each dNTP, 125 μM random pentamers and 1 U of phi29 DNA polymerase (New England Biolabs, Inc) for 2 hours at 30° C. Following the amplification, half the volumes (10 μL) of the amplicons were detected in the Luminex flow-cytometer system using the "Primary/Secondary" antibody detection protocol as described in Example 11.

TABLE 12

Random DNA Pentamers are the Optimal Primer Length. All primers Have Two Phosphorothioate Modifications at the 3'End.

| Copies/ assay | 5-mer | 6-mer | 7-mer | 8-mer | 9-mer | 10-mer |
|---|---|---|---|---|---|---|
| 0 | 10 | 9 | 7 | 13 | 9 | 14 |
| $1 \times 10^2$ | 5873 | 990 | 16 | 10 | 17 | 12 |
| $1 \times 10^4$ | 9864 | 5766 | 1469 | 176 | 36 | 26 |
| $1 \times 10^6$ | 12257 | 7567 | 7187 | 5444 | 2421 | 1621 |

* Values = Luminex Average MFI

TABLE 13

Comparison of Different Random Primer lengths and Modifications

| | 1-thio bond | | 2-thio bond | |
|---|---|---|---|---|
| Copies/assay | 5-mer | 6-mer | 5-mer | 6-mer |
| 0 | 11 | 10 | 12 | 7 |
| $1 \times 10^2$ | 851 | 4765 | 6972 | 922 |
| $1 \times 10^4$ | 10972 | 15250 | 15793 | 10758 |
| $1 \times 10^6$ | 22420 | 21097 | 19734 | 22313 |

* Values = Luminex Average MFI

Tables 12 and 13 show that random DNA hexamer primers were optimal with one phosphorothioate modification and primers that were random DNA pentamers were optimal with two phosphorothioate modifications.

EXAMPLE 11

Different Methods of Detecting Amplified Target

Three different protocols of detecting amplified targets were compared. One means utilized biotinylated probes which are oligodeoxynucleotides labeled with biotin at the 5' end. These oligonucleotides were prepared by the chemical synthesis by Integrated DNA Technology, Inc.; Salt Lake City, Utah. The two other approaches used labeled primary HC-Ab (Digene Corp.) and sequentially used primary HC-Ab and labeled secondary antibody (Digene Corp.), representing two embodiments of the invention. The combination of flow-cytometry detection of antibody-labeled or colored beads, and signal amplification resulted in an increased signal, and hence the sensitivity of the assay increased more then 10 fold. Signal amplification would normally increase the background of the assay as would the presence of a large complex on the beads, thus decreasing or eliminating sensitivity. However, the described inventive method provides for an increase in signal and sensitivity. The large complex on the beads could interfere with the detection mode that relies on a certain size of the beads in the Luminex flow-cytometer system. Both of these problems were overcome by the inventive method.

A. In one method, a biotinylated probe complementary to the target nucleic acid was applied to streptavidin-conjugated to phycoethithrin (SA-PE; Pierce). Amplified HPV 16 plasmid was denatured in 75 µl of 438 mM NaOH at 70° C. for 15 minutes. Two nanograms each of two 5'-biotinylated probes (5'-Biotin-TATTTTATATGACACAATGT-3' (SEQ ID NO:128); 5'-Biotin-GGTTTGTGCTAACAATAAATG-TATCCATAG-3' (SEQ ID NO:129)) were added to the denatured target nucleic acid sample in 25 µl of 0.125 M sodium citrate, 0.125 M sodium phosphate, 0.6 M triethanolamine, 0.6 BES, 0.83 M glacial acetic acid, 3% polyacrylic acid, 5 mM EDTA, 0.05% sodium azide and 0.4% Tween-20 (pH 3.6-4.1). Approximately 1000 polystyrene beads were conjugated to oligonucleotides specific for HPV 16 L- and E-regions (see Table 1) and immediately added to the neutralized sample. Hybridization was performed for 30 minutes at 50° C. while shaking at 1100 rpm. SA-PE (100 ng) in 100 µl of 438 mM NaOH, 0.125 M sodium citrate, 0.125 M sodium phosphate, 0.6 M triethanolamine, 0.6 BES, 0.83 M glacial acetic acid, 3% polyacrylic acid, 5 mM EDTA, 0.05% sodium azide and 0.4% Tween-20 was added to each reaction and incubated at room temperature for 5 minutes. The samples were then transferred to a filter plate where the unbound materials were removed by vacuum filtration. The beads were resuspended in 100 µl of PBS-0.05% Tween-20 and analyzed by Luminex flowcytometer after adjusting the gain of the photomultiplier tube to 700 volts.

B. In the second method, amplified HPV 16 plasmid was denatured in 75 µl of 438 mM NaOH at 70° C. for 15 minutes. A cocktail of 13 different types of HPV RNA (each 15 ng per assay, obtained as described in Example 6) was added to the denatured sample in 25 µl of 0.125 M sodium citrate, 0.125 M sodium phosphate, 0.6 M triethanolamine, 0.6 BES, 0.83 M glacial acetic acid, 3% polyacrylic acid, 5 mM EDTA, 0.05% sodium azide and 0.4% Tween-20 (pH 3.6-4.1). Thirteen sets of oligonucleotide-conjugated polystyrene beads ($5 \times 10^3$ beads per assay) were immediately added to the neutralized sample. Each bead set had two oligonucleotide sequences complementary to the late (L)- and early (E)-regions on the specific HPV type. Sequences of capture oligonucleotides were presented in Table 1. The RNA and bead-oligonucleotide conjugates were hybridized to the target nucleic acid for 30 minutes at 65° C. with shaking at 1100 rpm. The samples were then filtered in a 96-well filter plate (Whatman) and 1 µg of primary HC-Ab in 100 µl of PBS-0.05% Tween-20 was added. After shaking at room temperature for 5 minutes, reactions were filtered and 8 µg of PE-labeled secondary (goat-antimouse) antibody in 100 µl of PBS, 0.05% Tween-20, and 10% goat serum was added. Incubation continued for 20 minutes while shaking at room temperature. The excess antibody was removed by vacuum filtration and the beads with target complexes were resuspended in 100 µl PBS with 0.05% Tween-20. Samples were then analyzed by Luminex flow-cytometer after adjusting the gain of the photomultiplier tube to 700 volts.

C. In the third method, amplified HPV 16 plasmid was denatured in 75 µl of 438 mM NaOH at 70° C. for 15 minutes. A cocktail of 13 different types of HPV RNA (each 15 ng per assay, obtained as described in Example 6) was added to the denatured sample in 25 µl of 0.125 M sodium citrate, 0.125 M sodium phosphate, 0.6 M triethanolamine, 0.6 BES, 0.83 M glacial acetic acid, 3% polyacrylic acid, 5 mM EDTA, 0.05% sodium azide and 0.4% Tween-20 (pH 3.6-4.1). Thirteen sets of oligonucleotide-conjugated polystyrene beads ($5 \times 10^3$ beads per assay) were immediately added to the neutralized sample. Each bead set had two oligonucleotide sequences complementary to the late (L)- and early (E)-regions of the specific HPV type. Sequences of capture oligonucleotides were presented in Table 1. The RNA and bead-oligo conjugates were hybridized to the target for 30 minutes at 65° C. with shaking at 1100 rpm. The samples were then filtered through the 96-well filter plate (Whatman) and the beads were resuspended in 100 µl of PBS, 0.05% Tween-20, 10% goat serum and 10 ng of mouse monoclonal RNA:DNA specific antibodies labeled with phycoerythrin (PE-HC-Ab). The samples were then incubated for 30 minutes at room temperature (18°-25° C.) while shaking at 1100 rpm. Excess antibody was removed by vacuum filtration and the beads with target complexes were resuspended in 100 µl PBS with 0.05% Tween-20. Samples were then analyzed by Luminex flow-cytometer after adjusting the gain of the photomultiplier tube to 700 volts.

Isothermal amplification of HPV 16 target was performed as described in the Example 6. The amplified target was detected using one of three protocols as described in the above protocols A, B or C. The results are presented in Table 14. Of the three described protocols, detection with the biotinylated probes (Protocol A) involved the least amount of time to perform the method. However, this detection method also produced the lowest signal intensity. The greatest signal intensity and S/N ratio was achieved using the labeled primary antibody detection scheme (Table 14), which implemented HC-Ab signal amplification (Protocols B and C). Protocol C utilizes one fewer step than in protocol B and would be preferable.

TABLE 14

Comparison Of HPV 16 Detection After Isothermal Amplification

| Target input | Average of 3 median fluorescent intensities (MFI) | | |
|---|---|---|---|
| (copies/assay) | Protocol A | Protocol B | Protocol C |
| $5 \times 10^2$ | 174 | 4165 | 2506 |
| $5 \times 10^3$ | 517 | 7466 | 4715 |
| $5 \times 10^4$ | 776 | 9310 | 7001 |

EXAMPLE 12

HPV Typing in a 96-Well Nucleolink Plate

In an alternative embodiment, a microtiter plate may be used instead of beads as a solid support for sequence detection. Oligonucleotides specific for individual HPV types were conjugated to the bottom of the wells. The target nucleic acid hybridized to the capture oligonucleotides and then detected by chemiluminescence.

In preparation of the NucleoLink™ multi-well plate (Nalge Nunc International; New York), two oligonucleotide sequences complementary to the late (L)- and early (E)-regions on the specific HPV type were conjugated to the Nucleolink plate using the protocol described below. Sequences of capture oligonucleotides are presented in Table 1. By placing two oligonucleotides in each well, false negative results caused by the deletion of HPV L-region common in cancer cells may be eliminated. Type specific capture oligonucleotides (two per each HPV type) containing a 5'-C12-amino linker were prepared at a final concentration 100 nM (0.1 pmole/μL) in a freshly prepared solution of 10 mM 1-(3-dimethylaminopropyl)-3-ethylcarbodimide hydrochloride containing 10 mM 1-methylimidizole, pH 7. This solution was added at 100 μL per well (one type per well) to a Nucleolink 96-well plate, sealed with thermostable tape and incubated at 50° C. for 4 hours. The solution was then decanted and the wells were washed three times, soaked for 5 minutes and washed three times all with 100 mM Tris-HCl, pH 7.5, 150 mM sodium chloride, and 0.1% Tween-20 at room temperature. The wells were then washed three times, soaked for 5 minutes and washed three times with molecular biology grade water. The plates were then allowed to dry for 30 minutes at room temperature. The plates were stored at 4° C. in an ethylene bag with desiccant until needed.

The NucleoLink plate with covalently bound oligonucleotides was brought to room temperature after storage. The plate was blocked with 290 μL per well of 6% casein in 100 mM Tris-HCl, pH 7.2, 0.05% sodium azide, for 30 min at room temperature. Model samples (100 pg/mL) of dilutions of HPV plasmids (10 kb) prepared in a solution composed of 100 μg/mL Herring Sperm DNA, 1 M Guanidine-HCl, 10 mM Tris-HCl (pH 8.0), 10 mM EDTA, 0.05% Sodium Azide in deionized water. The samples (50 μl) were mixed in a 96-well microplate with 25 μL of 1.75M NaOH and incubated at 70° C. for 30 minutes. Unlabeled RNA probe (15 ng per assay) in 0.125 M sodium citrate, 0.125 M sodium phosphate, 0.6 M triethanolamine, 0.6 N,N-bis(2-hydroxyethyl)-2-aminoethane sulfonic acid, 0.83 M glacial acetic acid, 3% polyacrylic acid, 5 mM EDTA, 0.05% sodium azide and 0.4% Tween-20 (pH 3.6-4.1) was added to each well in the hybridization plate. The solution became clear or slightly yellow. The contents of each well were transferred to their respective wells in the Nucleolink plate. The plate was incubated at 65° C. while shaking at 1150 rpm for 1 hour. The plate was cooled to room temperature and the solution was decanted. A solution (100 μL/well) of alkaline phosphatase conjugated mouse monoclonal anti-RNA:DNA antibody in 0.1M mM Tris-pH 7.4, 0.6 M sodium chloride, 0.1 mM zinc chloride, 1 mM magnesium chloride 0.05% sodium azide, 0.25% tween-20, 0.2 mg/mL RNase, 4% hydroxypropyl-β-cyclodextrin, 0.05% goat IgG, 0.0008% Sulforhodamine B, with 30% blocking solution (6% casein in 100 mM Tris-HCl, pH 7.2, 0.05% sodium azide) was added to each well and the plate was incubated at 37° C. for 30 minutes. The solution was decanted and the plate was washed twice with 128 mM Tris pH 7.2; 0.6 M sodium chloride; 0.05% sodium azide; 0.24% Tween and then 250 μL of 128 mM Tris pH 7.2; 0.6 M sodium chloride; 0.05% sodium azide; 0.24% Tween was added to each well. The plate was sealed with thermostable tape and incubated at 60° C. for 10 minutes. The solution was decanted and the plate was washed twice more with 128 mM Tris pH 7.2; 0.6 M sodium chloride; 0.05% sodium azide. The plate was then washed twice with 40 mM Tris pH 8.2, 100 mM sodium chloride, 0.05% sodium azide. The solution was decanted and 100 μL of CDP-Star substrate was added to each well. The plate was incubated for 20 minutes in the dark and read on the DML luminometer. Table 15 shows the resulting signal to noise ratios of 100 pg/mL of 7 different HPV cloned targets as detected by the method described above.

TABLE 15

Typing of HPV 16, 18, 31, 33, 35, 45 and 52 on a 96 well plate

| Capture probes | HPV targets, Signal/Noise | | | | | | | |
|---|---|---|---|---|---|---|---|---|
| | 16 | 18 | 31 | 33 | 35 | 45 | 52 | No target |
| 16 | 30.6 | 1.2 | 1.1 | 0.7 | 0.3 | 0.6 | 0.8 | 1.0 |
| 18 | 0.5 | 21.9 | 1.1 | 0.5 | 1.1 | 1.5 | 0.7 | 1.0 |
| 31 | 0.6 | 0.5 | 264.4 | 0.6 | 0.6 | 1.7 | 1.8 | 1.0 |
| 33 | 0.4 | 1.2 | 1.8 | 91.7 | 0.5 | 1.2 | 0.4 | 1.0 |
| 35 | 0.4 | 0.3 | 1.7 | 0.4 | 103.6 | 0.7 | 0.4 | 1.0 |
| 45 | 1.1 | 1.9 | 0.8 | 0.8 | 1.0 | 34.3 | 0.5 | 1.0 |
| 52 | 0.7 | 0.5 | 0.5 | 0.5 | 0.7 | 0.5 | 44.4 | 1.0 |

EXAMPLE 13

Effects of Using a Mask in Conjunction with a Sub-Well Plate

A solution of alkaline phosphatase was added to CDP-Star substrate. This solution (20 μL) was added to the indicated sub-wells of a 384 well plate (Digene Corp.) and incubated for 20 minutes. The plate was then read on the 384 well plate luminometer at about 450 nm with and without the addition of a mask (Digene Corp.). Table 16 shows that a mask which covers each well/subwell increases the S/N ratio by more then 100-fold. The sub-well plate with the mask is advantageous for overcoming the previously known cross-talk between subwells. Each box of Table 16 represents a single sub-well. Only two subwells have chemiluminescent substrate, which are represented in bold face type.

TABLE 16

Cross-Talk Between Neighboring SubWells

| RELATIVE LIGHT UNITS WITHOUT MASK | | | |
|---|---|---|---|
| 1712 | 5598 | 2192 | 1210 |
| 4076 | 21986 | 5181 | 1262 |
| 1594 | 5024 | 2830 | 6046 |
| 1004 | 1051 | 4844 | 30128 |
| 1712 | 5598 | 2192 | 1210 |

| RELATIVE LIGHT UNITS WITH MASK | | | |
|---|---|---|---|
| 15 | 48 | 15 | 8 |
| 33 | 56548 | 40 | 26 |
| 18 | 24 | 12 | 16 |
| 31 | 16 | 23 | 64942 |
| 15 | 48 | 15 | 8 |

*Sub-wells with added chemiluminescent substrate are shown in bold.

EXAMPLE 14

HPV Typing in a 384-Sub-Well Plate

Detection of individual as well as multiple types of HPV in a sub-well plate format was performed. In this example, sample was added to each well and the individual targets migrated and hybridized to the corresponding capture sequence probes. The detection reagent was added to the well, where it bound to the target in the positive sub-wells. Chemiluminescence was used for detection.

Type specific capture oligonucleotides (two oligonucleotides per each HPV type) containing a 5'-C12-Amino linker were prepared at a final concentration of 5 µM (5 pmole/µL) to a solution of 500 mM sodium hydrogen phosphate, pH 8.5 containing 1 mM ethylenediaminetetraacetic acid disodium salt. This solution was added at 20 µL per well to each sub-well of the sub-well plate (one type per sub-well), sealed with thermostable tape and incubated at 42° C. for 4 hours. The solution was decanted and the wells were washed three times with TBS. The plate was then used immediately in the HPV typing assay.

The plate was blocked with 6% casein in 100 mM Tris-HCl, pH 7.2, 0.05% sodium azide (1 mL per large well), for 30 min at room temperature. Model samples (100 pg/mL) consist of dilution of HPV plasmids (10 kb) prepared in a solution composed of 100 µg/mL Herring Sperm DNA, 1 M Guanidine-HCl, 10 mM Tris-HCl (pH 8.0), 10 mM EDTA, 0.05% Sodium Azide in deionized water. The samples (500 µl) are mixed in an eppendorf tube with 250 µL of 1.75M NaOH and incubated at 70° C. for 30 min. Next, RNA Probe (15 ng per assay) in 0.125 M sodium citrate, 0.125 M sodium phosphate, 0.6 M triethanolamine, 0.6 N,N-bis(2-hydroxyethyl)-2-aminoethane sulfonic acid, 0.83 M glacial acetic acid, 3% polyacrylic acid, 5 mM EDTA, 0.05% sodium azide and 0.4% Tween-20 (pH 3.6-4.1) was added to each tube. The solution is now clear or slightly yellow. The contents of each tube (1 mL) were transferred to the respective well in the subwell plate. The plate was incubated at 65° C. with shaking at 1150 rpm for 1 hour. The plate was cooled to room temperature and the solution was decanted. A solution (1 mL per large well) of alkaline phosphatase conjugated mouse monoclonal anti RNA:DNA antibody in 100 mM Tris-pH 7.4, 0.6 M sodium chloride, 0.1 mM zinc chloride, 1 mM magnesium chloride 0.05% sodium azide, 0.25% tween-20, 0.2 mg/mL RNase, 4% hydroxypropyl-β-cyclodextrin, 0.05% goat IgG, 0.0008% Sulforhodamine B, with 30% blocking solution (6% casein in 100 mM Tris-HCl, pH 7.2, 0.05% sodium azide) was added to each well and the plate was incubated at 37° C. for 30 minutes. The solution was decanted and the plate was washed twice with 128 mM Tris pH 7.2; 0.6 M sodium chloride; 0.05% sodium azide; 0.24% Tween and then 1 mL of 128 mM Tris pH 7.2; 0.6 M sodium chloride; 0.05% sodium azide; 0.24% Tween was added to each well. The plate was sealed with thermostable tape and incubated at 60° C. for 10 minutes. The solution was decanted and the plate was washed twice more with 128 mM Tris pH 7.2; 0.6 M sodium chloride; 0.05% sodium azide; 0.24% Tween. The plate was then washed twice with 40 mM Tris pH 8.2, 100 mM sodium chloride, 0.05% sodium azide. The solution was decanted and 20 µL of CDP-Star substrate (Applera Corp.) was added to each well. The plate was incubated for 20 minutes in the dark and read on the 384-luminometer with the mask at about 450 nm as described in Example 13.

The results in Table 17 demonstrate the specificity of the detection of individual and multiple HPV types in the subwell plate. Signals shown in bold face type demonstrate the specificity of the detection. For example, HPV16 target gave a positive signal when presented with HPV16 probe only and gives no signal with probes for other HPV types. However, multiple infections give multiple signals.

TABLE 17

HPV Typing Using Passive Binding In The 384-Sub-Well Plate

| Target | Capture probes | | | | | | | |
|---|---|---|---|---|---|---|---|---|
| | 16 | 18 | 31 | 33 | 35 | 45 | 52 | 0 |
| No HPV | 1.0 | 1.0 | 1.0 | 1.0 | 1.0 | 1.0 | 1.0 | 1.0 |
| 16 | 22.3 | 1.7 | 1.0 | 0.9 | 0.7 | 1.2 | 1.1 | 1.1 |
| 18 | 1.7 | 4.9 | 0.8 | 1.0 | 1.0 | 1.0 | 0.8 | 0.9 |
| 31 | 1.5 | 1.6 | 2.6 | 0.9 | 0.9 | 0.8 | 0.9 | 0.9 |
| 33 | 2.6 | 2.2 | 1.2 | 30.7 | 0.8 | 1.1 | 0.9 | 1.3 |
| 35 | 2.2 | 2.1 | 1.0 | 1.1 | 11.0 | 1.1 | 0.8 | 1.1 |
| 45 | 1.7 | 1.8 | 0.9 | 0.9 | 1.1 | 8.4 | 0.7 | 1.2 |
| 52 | 1.9 | 2.1 | 1.1 | 1.1 | 1.0 | 1.1 | 6.8 | 1.1 |
| 16, 18, 31, 33, 35, 45, 52 | 35.7 | 8.2 | 4.4 | 28.4 | 11.1 | 9.9 | 5.1 | 1.2 |
| 16, 18, 31, 33, 35, 45 | 19.9 | 6.9 | 5.7 | 21.0 | 21.6 | 9.4 | 1.0 | 1.4 |
| 16, 18, 31, 33, 35 | 27.8 | 5.9 | 5.4 | 16.9 | 18.4 | 1.4 | 1.0 | 1.0 |
| 16, 18, 31, 33 | 25.4 | 5.7 | 6.2 | 17.9 | 0.9 | 1.0 | 1.1 | 1.5 |
| 16, 18, 31 | 27.5 | 5.3 | 4.7 | 1.3 | 1.2 | 1.2 | 1.1 | 1.6 |
| 16, 18 | 24.1 | 5.5 | 1.1 | 1.2 | 1.1 | 1.2 | 0.8 | 1.7 |
| Positive STM Sample | 78.8 | 11.3 | 5.3 | 2.0 | 2.1 | 1.4 | 1.3 | 1.9 |

EXAMPLE 15

Comparison of HPV Detection Methods Using a Microtiter Plate and Beads

Two assay formats of the invention were compared where the detection step is performed on a microtiter plate (as detected by chemiluminescence) or on Luminex carboxylated beads (as detected by fluorescence).

The target enrichment and target amplification steps were performed as described in the Example 6. The third step, involving hybridization and detection, was performed in two formats: one on Luminex carboxylated beads as described in Example 6, and the other on a microtiter plate as described in the Example 14.

The results in Table 18 show that the plate assay can detect 500 input copies in 30 minutes of amplifying with an S/N ratio of 9. At 1 hour of amplification, the plate assay is at least one order of magnitude more sensitive than the Luminex format.

TABLE 18

HPV detection using Beads and Plate detection format.

| Target Input copies/assay | 30 min amplification | | 60 min amplification | | 120 min amplification | |
|---|---|---|---|---|---|---|
| | S/N | % CV | S/N | % CV | S/N | % CV |
| Beads (fluorescence) | | | | | | |
| 0 | 1 | 20% | 1 | 21% | 1 | 16% |
| $5 \times 10^2$ | 1 | 8% | 24 | 3% | 1009 | 13% |
| $5 \times 10^3$ | 2 | 8% | 281 | 21% | 1548 | 5% |
| $5 \times 10^4$ | 18 | 14% | 1288 | 9% | 1520 | 19% |
| Plate (chemiluminescence) | | | | | | |
| 0 | 1 | 42% | 1 | 81% | 1 | 57% |
| $5 \times 10^2$ | 9 | 8% | 1046 | 29% | 12320 | 7% |
| $5 \times 10^3$ | 102 | 15% | 9054 | 6% | 11715 | 15% |
| $5 \times 10^4$ | 929 | 8% | 13019 | 5% | 12649 | 2% |

EXAMPLE 16

Effect of Nucleotide Ratio in Random Primers on the Efficiency of Isothermal Amplification Random primers were chemically synthesized using different combinations and ratios of nucleotides in the target amplification step of the method described in Example 6. The results in Table 19 show that dG and T play a major role in achieving efficient amplification. The omission of dA had a less pronounced effect and omitting dC had no effect at all. Isothermal amplification was performed for 2 hours with pentamer primers. The complete assay was performed as described in Example 6. Relative efficiency was calculated as signal to noise, where the efficiency of the standard primer composition was (1.0).

TABLE 19

Relative efficiency of target detection depending on the composition of random primers

| Primer composition | Target input (copies/assay) | Relative assay efficiency |
| --- | --- | --- |
| dA:T:dG:dC | 100 | (1.0) |
| 1:1:1:1 | 1000 | (1.0) |
| dA:T:dG | 100 | 0.95 |
| 1:1:1 | 1000 | 1.0 |
| T:dG:dC | 100 | 0.4 |
| 1:1:1 | 1000 | 0.6 |
| dA:dG:dC | 100 | 0.10 |
| 1:1:1 | 1000 | 0.12 |
| dA:T:dC | 100 | <0.1 |
| 1:1:1 | 1000 | <0.1 |
| dA:T:dG:dC | 100 | 0.7 |
| 1:1:3:1 | 1000 | 0.6 |
| dA:T:dG:dC | 100 | 0.95 |
| 2.5:2.5:4:1 | 1000 | 1.0 |
| dA:T:dG | 100 | 1.5 |
| 1:1:2 | 1000 | 1.2 |

EXAMPLE 17

HPV Typing on a Microchip Array

Detection of HPV types, individual as well as multiple types of HPV, on a microchip array format may be performed. Target nucleic acid capture and amplification are performed according to Example 6. Reagents and washing protocols are performed according to commercially available products and instructions for washing slides, membranes, chips, etc. The target detection step comprises target denaturation and hybridization to the RNA probes, or signal sequence probes, both according the Example 6.

In this example, hybridization of target to the sequence specific capture sequence oligonucleotide probe occurs on a spotted oligonucleotide array rather than on beads, as described in Example 6. The term "spotted array" refers to a 2-dimensional series of elements on the surface of a solid support, where each element is an aliquot of oligonucleotide deposited in a specific location. Solid supports for this format include: a glass slide, nylon membrane, or a microchip (glass or silicon). Further examples and description are found in "Microarrays And Cancer Research" Ed. J. Warrington, Eaton Publishing, 2002.

Type-specific capture sequence oligonucleotide probes (two oligonucleotides per each HPV type) modified with a 5'-C12-Amino linker is spotted on a solid support, such as a microarray, each spot corresponding to a specific HPV type. Oligonucleotides are attached through, for example, the primary amino group. The solid support is equilibrated with 2×SSC (sodium chloride and sodium citrate) buffer at room temperature for 10 min, followed by 30 min incubation at 37° C. in pre-hybridization buffer (2×SSC/0.05% blocking reagent/5% dextran sulfate/0.1% SDS) with 50 micrograms per mL of denatured salmon sperm DNA. Hybridization is then performed in the same pre-hybridization buffer with the addition of amplified target nucleic acids and RNA signal sequence probes. Hybridization of the target nucleic acids, RNA signal sequence probes, and type-specific capture sequence oligonucleotide probes occurs while incubating at 37° C. with shaking for 3 hours in rehybridization solution.

Detection of the spots containing amplicon may be performed in two ways: a) using HYBRID CAPTURE antibodies (HC-Ab) labeled with Cy-fluorescent dye, with subsequent scanning using commercially available scanners; or b) by using alkaline phosphatase labeled HC-Ab with subsequent application of precipitating substrate (for example, 5-bromo-4-chloro-3-indolyl-phosphate and nitroblue tetrazolium: NBT/BCIP). In the latter case, the signal is detectable without instrumental assistance.

The above description of various embodiments has been presented for purposes of illustration and description. It is not intended to be exhaustive or limiting to the precise forms disclosed. Obvious modifications or variations are possible in light of the above teachings. The embodiments discussed were chosen and described to provide illustrations and its practical application to thereby enable one of ordinary skill in the art to utilize the various embodiments and with various modifications as are suited to the particular use contemplated. All such modifications and variations are within the system as determined by the appended claims when interpreted in accordance with the breadth to which they are fairly, legally and equitably entitled.

What is claimed is:

1. A composition comprising:
   (a) a plurality of at least one probe selected from the group consisting of SEQ ID NO: 9 to 21 and a full-length complement thereof;
   (b) an HPV nucleic acid hybridized to at least a portion of the plurality of probe (a) to form an RNA:DNA hybrid;
   (c) at least one nucleic acid primer hybridized to the HPV nucleic acid;
   (d) an antibody bound to the RNA:DNA hybrid, wherein said antibody is bound to a solid support; and
   (e) a blocker probe hybridized to at least a portion of the plurality of probes from (a).

2. The composition of claim 1 further comprising at least a second nucleic acid probe selected from the group consisting of SEQ ID NO: 1 to 8, SEQ ID NO 22 to 64, and a complement thereof.

3. The composition of claim 2 wherein probe (a) and the second nucleic acid probe are capture sequence probes specific for an HPV nucleic acid.

4. The composition of claim 3 further comprising at least one nucleic acid having a sequence that is complementary to at least a portion of probe (a) or the second nucleic acid probe or both.

5. The composition of claim 3 further comprising at least one signal sequence probe.

6. A bead set formed from a composition of claim 3.

7. A bead set formed from a composition of claim 1.

8. A bead set formed from a composition of claim 2.

9. The composition of claim 1 wherein said solid support is a bead.

10. The composition of claim 1 further comprising a DNA polymerase associated with the target nucleic acid.

11. The composition of claim 10, wherein said composition is in an environment suitable for performing an isothermal amplification.

* * * * *